US011773380B1

(12) United States Patent
Cayouette et al.

(10) Patent No.: US 11,773,380 B1
(45) Date of Patent: Oct. 3, 2023

(54) POLYMERASE MUTANTS AND USE WITH 3'-OH UNBLOCKED REVERSIBLE TERMINATORS

(71) Applicant: Agilent Technologies, Inc., Santa Clara, CA (US)

(72) Inventors: Michelle Cayouette, San Diego, CA (US); Jeffrey Fox, Escondido, CA (US); Connie Hansen, San Diego, CA (US); Holly Hogrefe, San Diego, CA (US); Weidong Wu, Houston, TX (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 17/894,854

(22) Filed: Aug. 24, 2022

Related U.S. Application Data

(63) Continuation of application No. PCT/US2021/070785, filed on Jun. 29, 2021.

(51) Int. Cl.
  *C12N 9/12* (2006.01)
  *C12P 19/34* (2006.01)
  *C12Q 1/6869* (2018.01)

(52) U.S. Cl.
  CPC ............ *C12N 9/1252* (2013.01); *C12P 19/34* (2013.01); *C12Q 1/6869* (2013.01); *C12Y 207/07007* (2013.01)

(58) Field of Classification Search
  None
  See application file for complete search history.

(56) References Cited

U.S. PATENT DOCUMENTS

| | | |
|---|---|---|
| 5,789,166 A | 8/1998 | Bauer et al. |
| 5,932,419 A | 8/1999 | Bauer et al. |
| 5,948,663 A | 9/1999 | Mathur |
| 6,183,997 B1 | 2/2001 | Hogrefe |
| 6,391,548 B1 | 5/2002 | Bauer et al. |
| 6,444,428 B1 | 9/2002 | Hogrefe |
| 6,734,293 B1 | 5/2004 | Hogrefe et al. |
| 7,132,265 B2 | 11/2006 | Bauer et al. |
| 7,176,004 B2 | 2/2007 | Bauer et al. |
| 8,435,775 B2 * | 5/2013 | Holliger .............. C12P 19/34 536/23.1 |
| 8,969,535 B2 | 3/2015 | Wu et al. |
| 9,200,319 B2 | 12/2015 | Litosh et al. |
| 9,273,352 B2 | 3/2016 | Smith et al. |
| 9,677,057 B2 | 6/2017 | Bomati et al. |
| 9,677,059 B2 | 6/2017 | Reisinger et al. |
| 9,765,309 B2 | 9/2017 | Chen et al. |
| 10,041,115 B2 | 8/2018 | Stupi et al. |
| 10,752,887 B2 | 8/2020 | Champion et al. |
| 11,034,942 B1 * | 6/2021 | Naji .................. C12N 9/1252 |
| 2003/0228616 A1 | 12/2003 | Arezi et al. |
| 2016/0032377 A1 | 2/2016 | Chen et al. |
| 2020/0216841 A1 | 7/2020 | Eberwine et al. |

FOREIGN PATENT DOCUMENTS

| | | |
|---|---|---|
| WO | 2021194640 A1 | 9/2021 |

OTHER PUBLICATIONS

Agilent Technologies, et al., "PfuTurbo DNA Polymerase, Instruction Manual, Catalog #600250, #600252, #600254 and #600256, Revision G0," 17 pages.

Agilent Technologies, et al., "QuikChange Lightning Multi Site-Directed Mutagenesis Kit, Instruction Manual, Catalog # 210514 and #210516, Revision E.0," 23 pages.

Cozens, Christopher et al., "A Short Adaptive Path From DNA to RNA Polymerases," PNAS vol. 109, No. 21, Jun. 22, 2012, 8067-8072.

Eisenstein, Michael et al., "Enzymatic DNA Synthesis Enters New Phase," Nature Biotechnology, vol. 38, Oct. 5, 2020, 1113-1115.

Elshawadfy, Ashraf M. et al., "DNA Polymerase Hybrids Derived From the Family-B Enzymes of Pyrococcus Furiosus and Thermococcus Kodakarensis: Improving Performance in the Polymerase Chain Reaction," Frontiers in Microbiology, vol. 5, No. 224, May 27, 2014, 14 pages.

Gardner, Andrew F. et al., "Therminator DNA Polymerase: Modified Nucleotides and Unnatural Substrates," Frontiers in Molecular Biosciences; vol. 6, Article 28, Apr. 2019, 9 pages.

Hansen, Connie J. et al., "Engineered Split in Pfu DNA Polymerase Fingers Domain Improves Incorporation of Nucleotide C-Phosphate Derivative," Nucleic Acids Research, 2011, vol. 39, No. 5, Nov. 9, 2010, 1801-1810.

Hoff, Kendall et al., "Enzymatic Synthesis of Designer DNA Using Cyclic Reversible Termination and a Universal Template," ACS Synthetic Biology, vol. 9, Jan. 14, 2020, 283-293.

Jensen, Michael A. et al., "Template-Independent Enzymatic Oligonucleotide Synthesis (TiEOS): Its History, Prospects, and Challenges," American Chemical Society, Biochemistry, vol. 57, No. 12, Mar. 13, 2018, 1821-1832.

Mathews, Anu S. et al., "3'-O-Caged 2-Deoxynucleoside Triphosphates for Light-Mediated, Enzyme-Catalyzed, Template-Independent DNA Synthesis," Current Protocols in Nucleic Acid Chemistry, Dec. 2017, 13.17.1-13.17.38.

Palluk, Sebastian et al., "De Novo DNA Synthesis Using Polymerase-Nucleotide Conjugates," Nature Biotechnology vol. 36, No. 7, Jun. 18, 2018, 11 pages.

Ramsay, Nicola et al., "CyDNA: Synthesis and Replication of Highly Cy-Dye Substituted DNA by an Evolved Polymerase," American Chemical Society, vol. 132, No. 14, Mar. 17, 2010, 5096-5104.

Weidong Wu, et al., "Termination of DNA synthesis by N6-alkylated, not 3'-O-alkylated, photocleavable 2'-deoxyadenosine triphosphates," Nucleic Acids Research, vol. 35, Issue 19, Oct. 1, 2007, pp. 6339-6349.

(Continued)

*Primary Examiner* — Richard G Hutson

(57) ABSTRACT

Mutant polymerases are provided that have improved ability to incorporate modified nucleotides, including 3'-OH unblocked reversible terminators. The mutant polymerases may be used in a variety of applications, such as for polynucleotide sequencing, primer extension reactions, and template-independent enzymatic oligonucleotide synthesis.

22 Claims, 52 Drawing Sheets

Specification includes a Sequence Listing.

(56) References Cited

OTHER PUBLICATIONS

Litosh, Vladislav A. et al., "Improved nucleotide selectivity and termination of 3'-OH unblocked reversible terminators by molecular tuning of 2-nitrobenzyl alkylated HOMedU triphosphates," Nucleic Acids Research, vol. 39, Issue 6, Mar. 1, 2011, p. e39.

Stupi, Brian P. et al., "Stereochemistry of Benzylic Carbon Substitution Coupled with Ring Modification of 2-Nitrobenzyl Groups as Key Determinants for Fast-Cleaving Reversible Terminators", Angew. Chem. Int. Ed. 2012, 51, 1724-1727.

Gardner, Andrew F. et al., "Rapid incorporation kinetics and improved fidelity of a novel class of 3'-OH unblocked reversible terminators", Nucleic Acids Research, vol. 40, Issue 15, Aug. 1, 2012, pp. 7404-7415.

Evans, Steven J. et al., "Improving dideoxynucleotide-triphosphate utilisation by the hyper-thermophilic DNA polymerase from the archaeon Pyrococcus furiosus", Nucleic Acids Research, 28(5):1059-66 (2000).

Pinheiro, Vitor B. et al., "Synthetic genetic polymers capable of heredity and evolution," (2012) Science 336:341-4. doi: 10.1126/science.1217622. PMID: 22517858.

Kennedy, Edward M. et al., "The Mechanistic Architecture of the Thermostable Pyrococcus Furiosus Family B DNA Polymerase Motif A and its Interaction with dNTP Substrate," (2009) Biochemistry 48(47):11161-11168. doi: 10.1021/bi9010122. PMCID: PMC3097049.

Hertzog, David et al., "A high-performance, low-cost approach to next-generation sequencing", BioOptics World. 2011 Issue Nov./Dec. 2011.

* cited by examiner

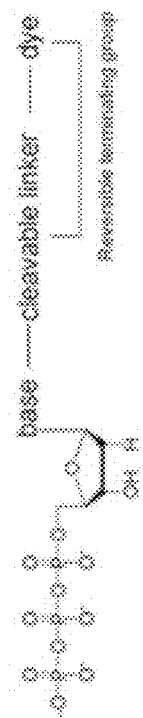
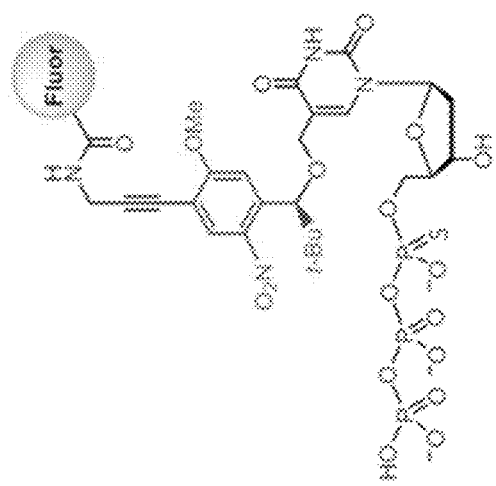
FIG. 1A
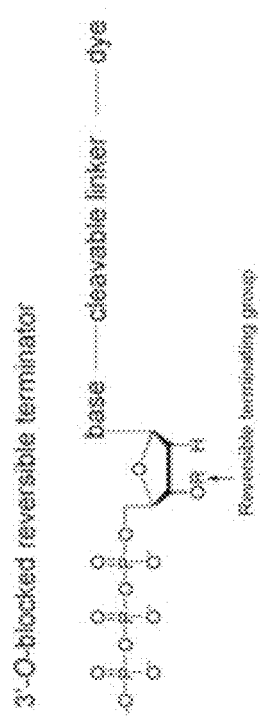
FIG. 1B
FIG. 1C

US 11,773,380 B1

POLYMERASE MUTANTS AND USE WITH 3'-OH UNBLOCKED REVERSIBLE TERMINATORS

CROSS-REFERENCE TO RELATED APPLICATIONS

This application is a continuation pursuant to 35 U.S.C. § 365 of International Application No. PCT/US2021/070785, filed on Jun. 29, 2021, which is incorporated herein by reference in its entirety.

REFERENCE TO SEQUENCE LISTING

The computer-readable Sequence Listing submitted on Sep. 28, 2022 and identified as follows: 22792 bytes ST.26 XML file named "20200132-02 Sequence Listing 2022-09-28.xml" created Sep. 28, 2022, is incorporated herein by reference in its entirety.

FIELD OF THE INVENTION

The present invention relates to mutant polymerases and methods of using such mutant polymerase for polynucleotide sequencing, primer extension reactions, and other applications.

BACKGROUND OF THE INVENTION

Polymerases naturally occur in organisms to replicate and maintain their genomes. Polymerases have been harnessed in the biotechnology field for a wide variety of applications, including PCR and sequencing. Polymerases enable the replication of DNA or RNA by detecting complementarity between nucleotide bases and/or recognizing structural features of an oligonucleotide strand, and acting as an enzyme for a reaction between a nucleotide and the 3'-end of the strand. There remains a need for polymerases for various biotech applications with improved incorporation of nucleotides, in particular nucleotides which are modified to act as reversible terminators in polymerization of nucleic acids.

The Terminator DNA polymerase is a derivative of the Family B *Thermococcus* sp. 9° N-7 DNA polymerase. Therminator is commercially available from New England Biolabs, Inc. (Ipswich, Mass.), and its properties and applications were recently reviewed in Gardner, et al., "Therminator DNA Polymerase: Modified Nucleotides and Unnatural Substrates", Front. Mol. Biosci., 24 Apr. 2019 (doi.org/10.3389/fmolb.2019.00028).

*Pyrococcus furiosus* (Pfu) is a hyperthermophilic species of archaea originally isolated from geothermally heated marine sediments with temperatures between 90° C. and 100° C. *Pyrococcus furiosus* possesses a Family B DNA polymerase which has been used for polymerase chain reaction (PCR) and other biotechnology applications. See PfuTurbo DNA Polymerase Instruction Manual, Revision G0, ©Agilent Technologies, Inc. 2015, 2020; Elshawadfy, et al., "DNA polymerase hybrids derived from the family-B enzymes of *Pyrococcus furiosus* and *Thermococcus kodakarensis*: improving performance in the polymerase chain reaction." Front Microbiol. 2014 May 27; 5:224. doi: 10.3389/fmicb.2014.00224.

Many wild-type and mutant DNA polymerases have been used, or have the potential to be used, in a variety of biotechnology applications, especially if they have the capability to incorporate modified nucleotides. Such DNA polymerases may be useful for polynucleotide sequencing, cloning, PCR or other amplification, single nucleotide polymorphism (SNP) detection, whole genome amplification (WGA), synthetic biology, molecular diagnostics, and other applications.

One potential application for DNA polymerases is for enzyme-mediated oligonucleotide synthesis (TiEOS, Template-Independent Enzymatic Oligo Synthesis). TiEOS is an approach to generating long nucleic acid polymers from both natural and modified nucleotides. See Jensen, et al., "Template-Independent Enzymatic Oligonucleotide Synthesis (TiEOS): Its History, Prospects, and Challenges", (2018) Biochemistry 57:1821-32. Current approaches combine template-independent DNA polymerases with reversibly-modified terminators to control oligonucleotide elongation to a single-base addition per cycle. A preferred enzyme for TiEOS is terminal deoxynucleotidyl transferase (TdT). Classified as a Family X DNA polymerase, TdT adds nucleotides in a template-independent manner in vivo to increase antigen receptor diversity in mammals. TdT incorporates reversible terminators with less than 100% efficiency, which limits the length and fidelity of the resulting synthetic oligonucleotides. To date, the longest oligo synthesized enzymatically was reported by DNA Script (280mer @99.4% stepwise yield) using an engineered Family X DNA polymerase. See Eisenstein (2020) Nature Biotechnology 38:1113-1115; and U.S. Pat. No. 10,752,887. In addition, many of the reversible terminators developed for use in sequencing-by-synthesis leave behind a scar or modification after the terminating group is removed from the nucleotide's sugar (3'-OH blocked) or base (3'-OH unblocked).

There is a need for polymerases for polynucleotide sequencing and other biotechnology applications with improved capability to incorporate modified nucleotides, including nucleotides modified to function as reversible terminators. There is also a need for enzymes that incorporate scarless reversible terminators in a template-independent fashion with high incorporation and termination efficiencies.

SUMMARY OF THE INVENTION

As one aspect of the present invention, mutant polymerases are provided. The mutant polymerases comprise an amino acid sequence that is at least 80% identical to SEQ ID NO:1, and also comprises at least one amino acid substitution at one or more positions functionally equivalent to amino acid positions in Pfu polymerase which are identified herein. In some embodiments, the polymerase comprises a mutation at a position functionally equivalent to position 486 in Pfu polymerase, and/or comprises a mutation at a position functionally equivalent to position 546 in Pfu polymerase, and/or comprises a mutation at a position functionally equivalent to position 477 in Pfu polymerase. Exemplary mutant polymerases include those comprising the amino acid sequences of SEQ ID NO:2, SEQ ID NO:9, SEQ ID NO:10, SEQ ID NO:4, or SEQ ID NO:5.

As another aspect of the present invention, compositions are provided which comprise a reversible terminator and a mutant polymerase as described herein. In some embodiments, the reversible terminator is a 3'-OH-unmodified reversible terminator (such as a Lightning Terminator). See, e.g., Weidong Wu, et al., "Termination of DNA synthesis by N6-alkylated, not 3'-O-alkylated, photocleavable 2'-deoxyadenosine triphosphates," Nucleic Acids Research, Volume 35, Issue 19, 1 Oct. 2007, Pages 6339-6349; Vladislav A. Litosh, et al., "Improved nucleotide selectivity and termination of 3'-OH unblocked reversible terminators by molecular tuning of 2-nitrobenzyl alkylated HOMedU triphosphates," Nucleic Acids Research, Volume 39, Issue 6, 1 Mar. 2011, Page e39; and Brian P. Stupi, et al., "Stereochemistry of Benzylic Carbon Substitution Coupled with Ring Modification of 2-Nitrobenzyl Groups as Key Determinants for Fast-Cleaving Reversible Terminators", Angew. Chem. Int. Ed. 2012, 51, 1724-1727; Andrew F. Gardner, et al., "Rapid incorporation kinetics and improved fidelity of a novel class of 3'-OH unblocked reversible terminators", Nucleic Acids Research, Volume 40, Issue 15, 1 Aug. 2012, Pages 7404-7415.

As another aspect, a composition comprising a 3'-OH unblocked reversible terminator and a mutant polymerase is provided. The mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

As another aspect, a method is provided for incorporating a nucleotide to a priming strand comprising a nucleic acid. The method comprises contacting the priming strand with a nucleotide and a mutant polymerase under conditions sufficient for an incorporation reaction. The mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

Another aspect of the present invention relates to a method of polynucleotide sequencing. The method comprises (a) forming a duplex comprising a template and a priming strand, wherein the template comprises a target nucleic acid to be sequenced and a primer binding site complementary to at least a portion of the priming strand; (b) combining the priming strand with a reversible terminator nucleotide and a mutant polymerase, wherein said mutant polymerase comprises an amino acid sequence that is at least 96% identical to SEQ ID NO:2 and comprises amino acid mutations at positions functionally equivalent to amino acid positions at K477, A486 and Y546 in Pfu polymerase; (c) incorporating the reversible terminator at a 3'-end of the priming strand in a template-dependent reaction; and (d) identifying the incorporated reversible terminator nucleotide, thereby determining the sequence of the template.

As another aspect of the present invention, a composition comprising a priming strand, a 3'-OH unblocked reversible terminator, and a mutant polymerase is provided. The mutant polymerase comprises an amino acid sequence that is at least 80% (alternatively, at least 85%, 90%, or 95%) identical to SEQ ID NO:1. The mutant polymerase further comprises one or more mutations at positions functionally equivalent to positions L270, E330, Q332, L333, L409, P451, L453, L457, E476, L489, L490, N492, F494, Y497, and E581 in Pfu polymerase. The mutant polymerase has an incorporation activity at least 4-fold higher than an incorporation activity of the DNA polymerase of SEQ ID NO:11.

As yet another aspect, a method of incorporating 3'-OH-unmodified reversible terminators into a priming strand is provided. The method comprises contacting a priming strand with a 3'-OH-unmodified reversible terminator and a mutant polymerase under conditions sufficient for an incorporation reaction. The mutant polymerase comprises an amino acid sequence that is at least 80% identical to SEQ ID NO:1 and one or more mutations at positions functionally equivalent to positions L270, E330, Q332, L333, L409, P451, L453, L457, E476, L489, L490, N492, F494, Y497, and E581 in Pfu polymerase. The method also comprises incorporating the 3'-OH-unmodified reversible terminator at a 3'-end of the priming strand.

As another aspect, a composition comprising a priming strand, an 3'-OH-unmodified reversible terminator, and a mutant polymerase is provided. The mutant polymerase is at least 96% identical to SEQ ID NO:2 and comprises: a Y546H mutation at a position functionally equivalent to position 546 in Pfu polymerase; a L409Y, L409H or L409F mutation at a position functionally equivalent to position 409 in Pfu polymerase; and a A486X mutation at a position functionally equivalent to position 486 in Pfu polymerase, wherein X is any amino acid except alanine.

As another aspect of the present invention, a method is provided for incorporating a single nucleotide into a priming strand in a template-independent reaction. The method comprises combining a priming strand with a 3'-OH-unmodified reversible terminator and a mutant polymerase. The mutant polymerase is at least 96% identical to SEQ ID NO:2 and comprises: a Y546H mutation at a position functionally equivalent to position 546 in Pfu polymerase; a L409Y, L409H or L409F mutation at a position functionally equivalent to position 409 in Pfu polymerase; and a A486X mutation at a position functionally equivalent to position 486 in Pfu polymerase, wherein X is any amino acid except alanine. Incorporation of the terminator is at least 2-fold (alternatively, 4-fold or 10-fold) higher than for the mutant DNA polymerase of SEQ ID NO:11.

As another aspect, a method is provided for 3'-OH template-independent oligonucleotide synthesis. The method comprises combining a priming strand, an 3'-OH-unmodified reversible terminator, and a mutant DNA polymerase. The mutant DNA polymerase comprises: an amino acid sequences that is at least 96% identical to SEQ ID NO:2; a Y546H mutation to histidine at a position functionally equivalent to position 546 in Pfu polymerase; a L409Y, L409H, or L409F mutation at a position functionally equivalent to position 409 in Pfu polymerase; and a A486X mutation at a position functionally equivalent to position 486 in Pfu polymerase, wherein X is any amino acid except alanine. The method also comprises incorporating the 3'-OH unblocked unmodified reversible terminator to the priming strand.

These and other features and advantages of the present methods and compositions will be apparent from the following detailed description, in conjunction with the appended claims.

BRIEF DESCRIPTION OF THE DRAWINGS

FIG. 1A illustrates a reversible (3'-OH unblocked) Lightning Terminator with 5-hydroxylmethyluracil base and attached dye, used for DNA Sequencing. FIGS. 1B and 1C show the difference in concept between a 3-OH blocked terminator and an unmodified-3-OH terminator (used in this disclosure). FIG. 1E ("LTA-1") is modified at the N6 position of adenosine with a nitrobenzyl moiety. FIG. 1F ("LTA-2") is modified with α-tert-butyl nitrobenzul moiety on the 7-hydroxylmethyl-7-deaza-deoxyadenosine, and optionally with an α-thio modification on triphosphate moiety.

449; and D-(4 segments of 20-40 amino acids spanning 500-599). For domain D, ARL and L+L is expressed as the mean value exhibited by the 4 sub-chimeric polymerases.

Figure 3:
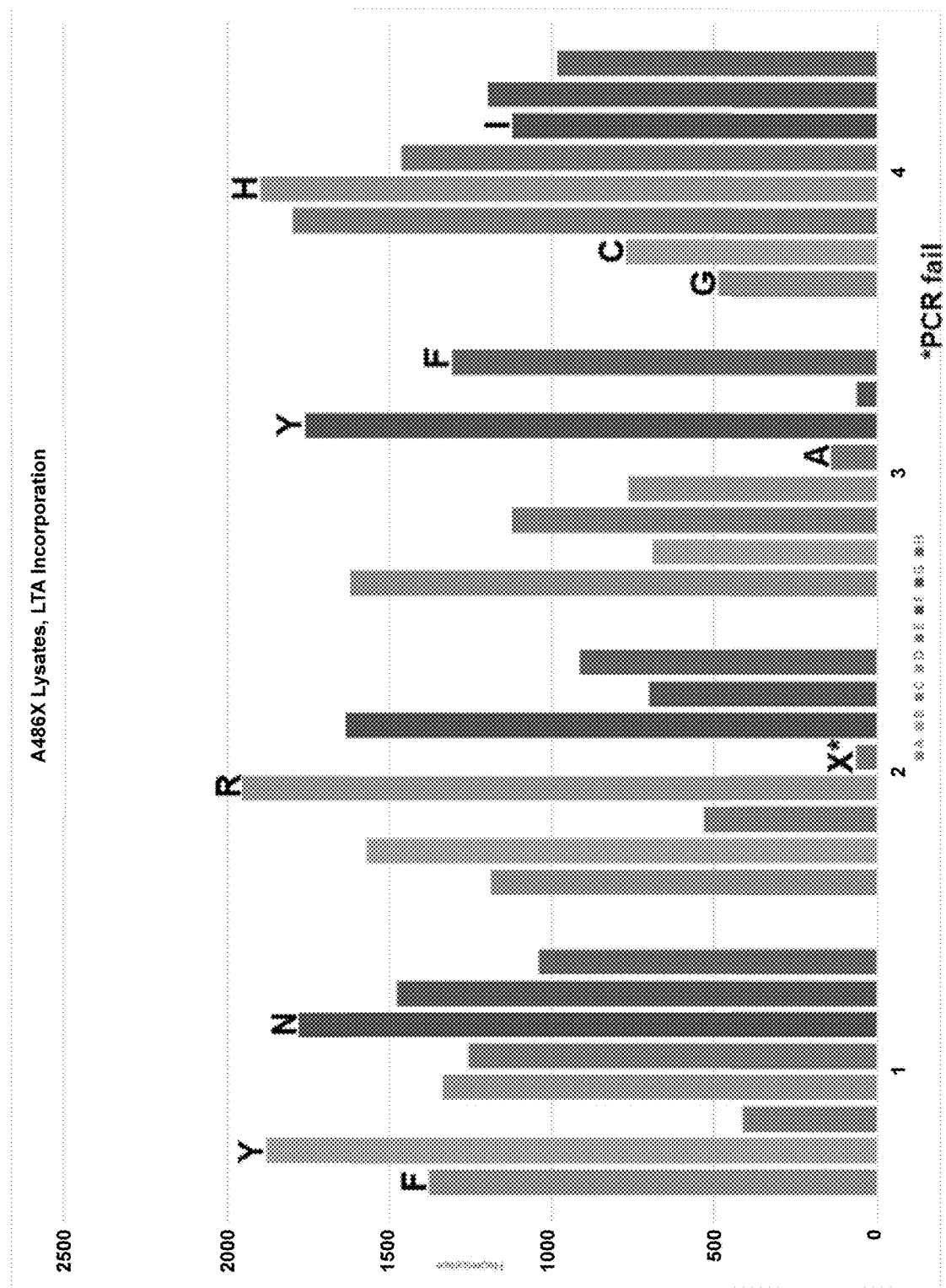

FIG. 3 shows activity of mutant polymerases having mutations at position 486 of Pfu polymerase for incorporation of a reversible terminator (LTA).

Figure 4A:
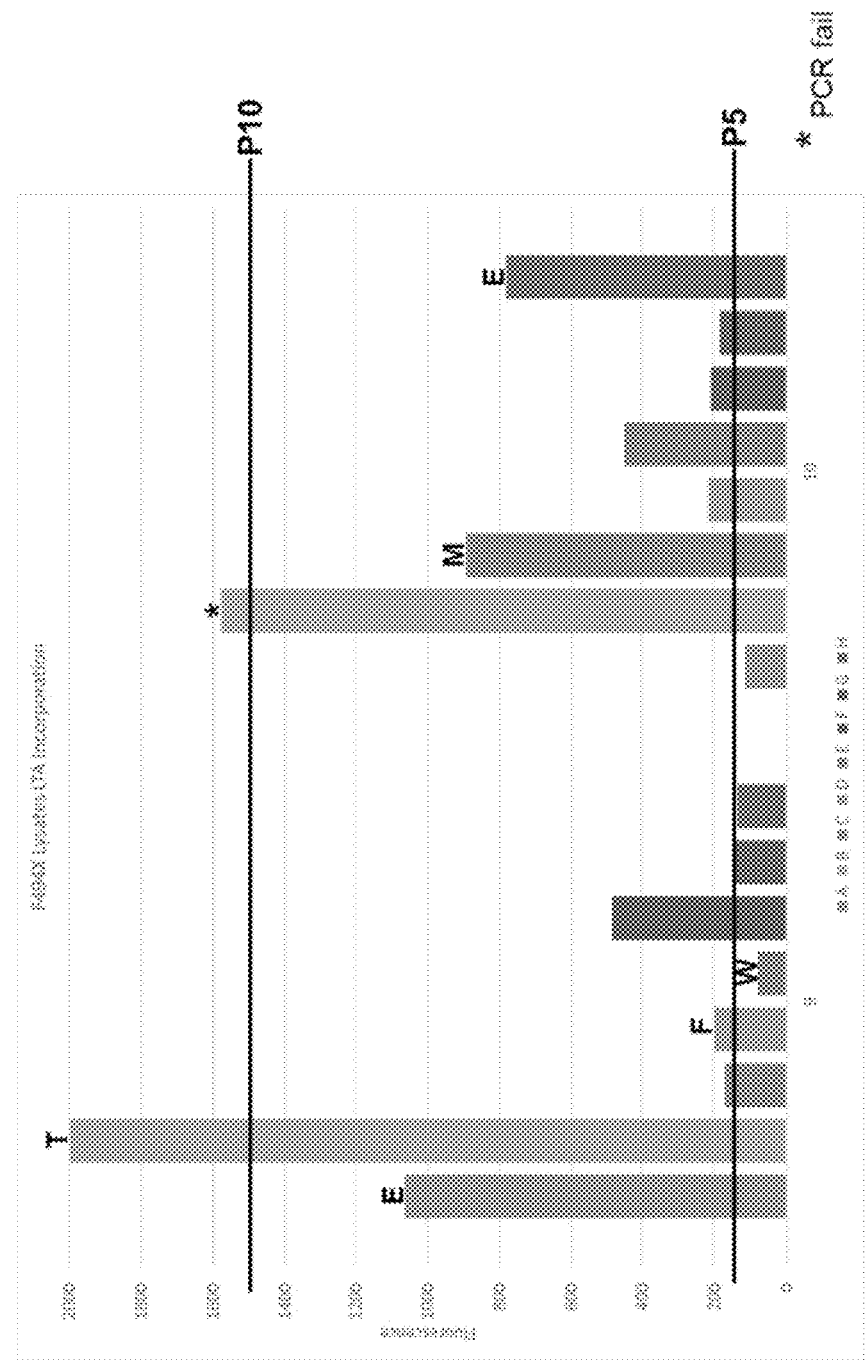
Figure 4B:
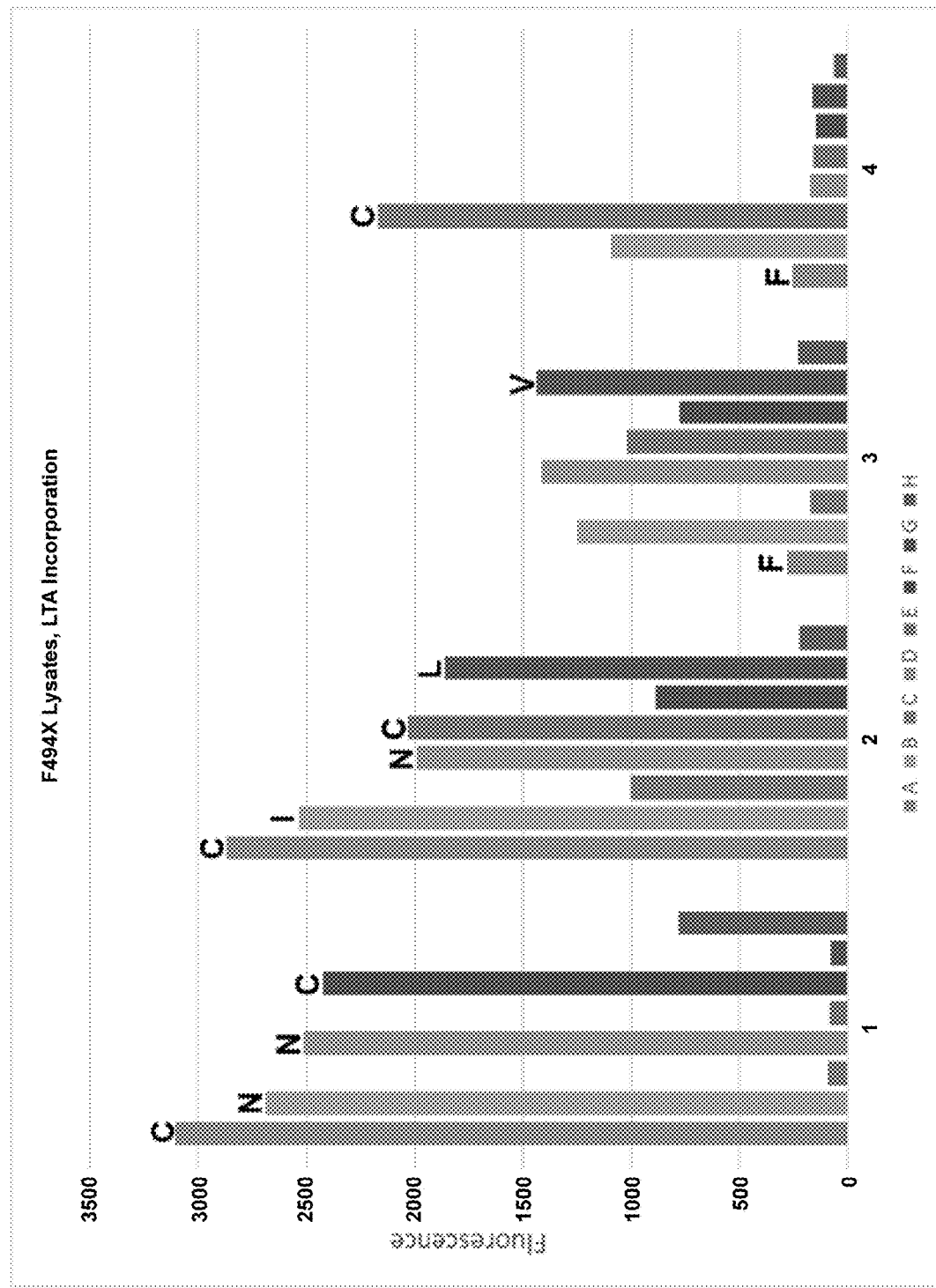

FIGS. 4A and 4B shows activity of various F494X mutant polymerases tested in Example 5 for incorporation of a reversible terminator (LTA).

Figure 5:
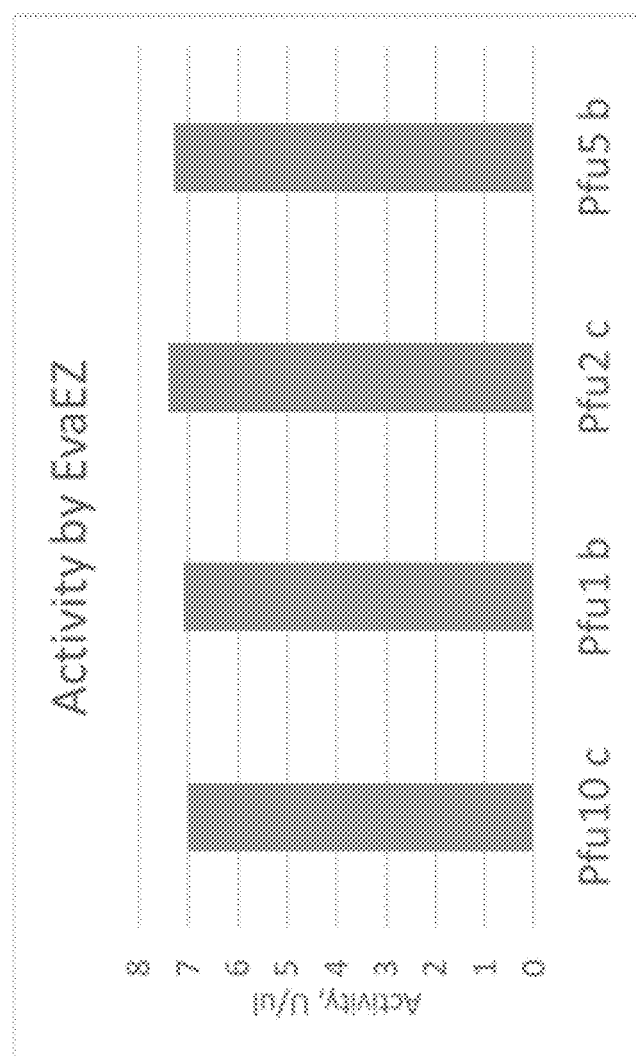

FIG. 5 shows activity of various mutant polymerases tested with natural nucleotides in Example 6.

Figure 6:
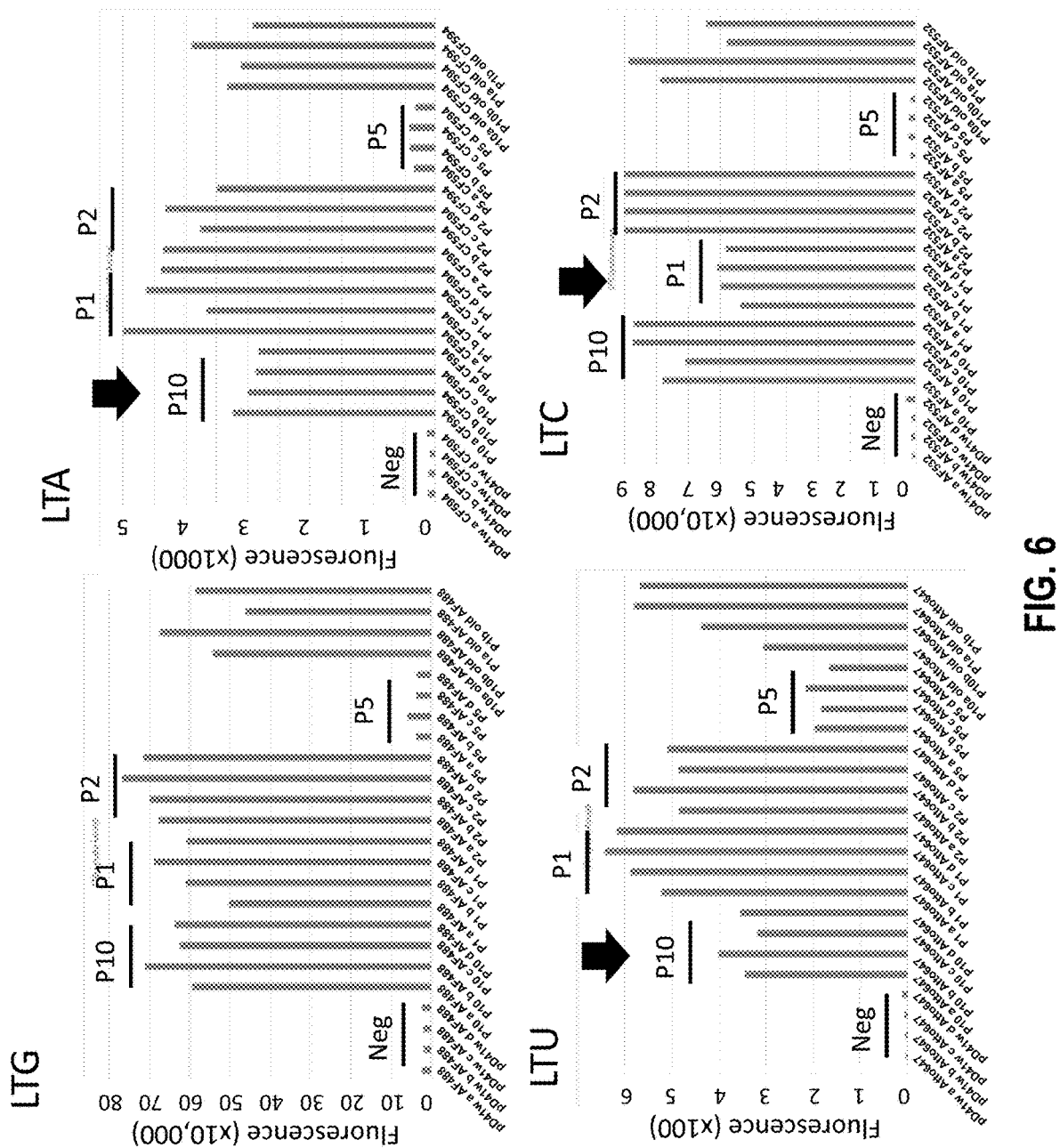

FIG. 6 shows relative incorporation of reversible terminators by various mutant polymerases tested in Example 6.

Figure 7A:
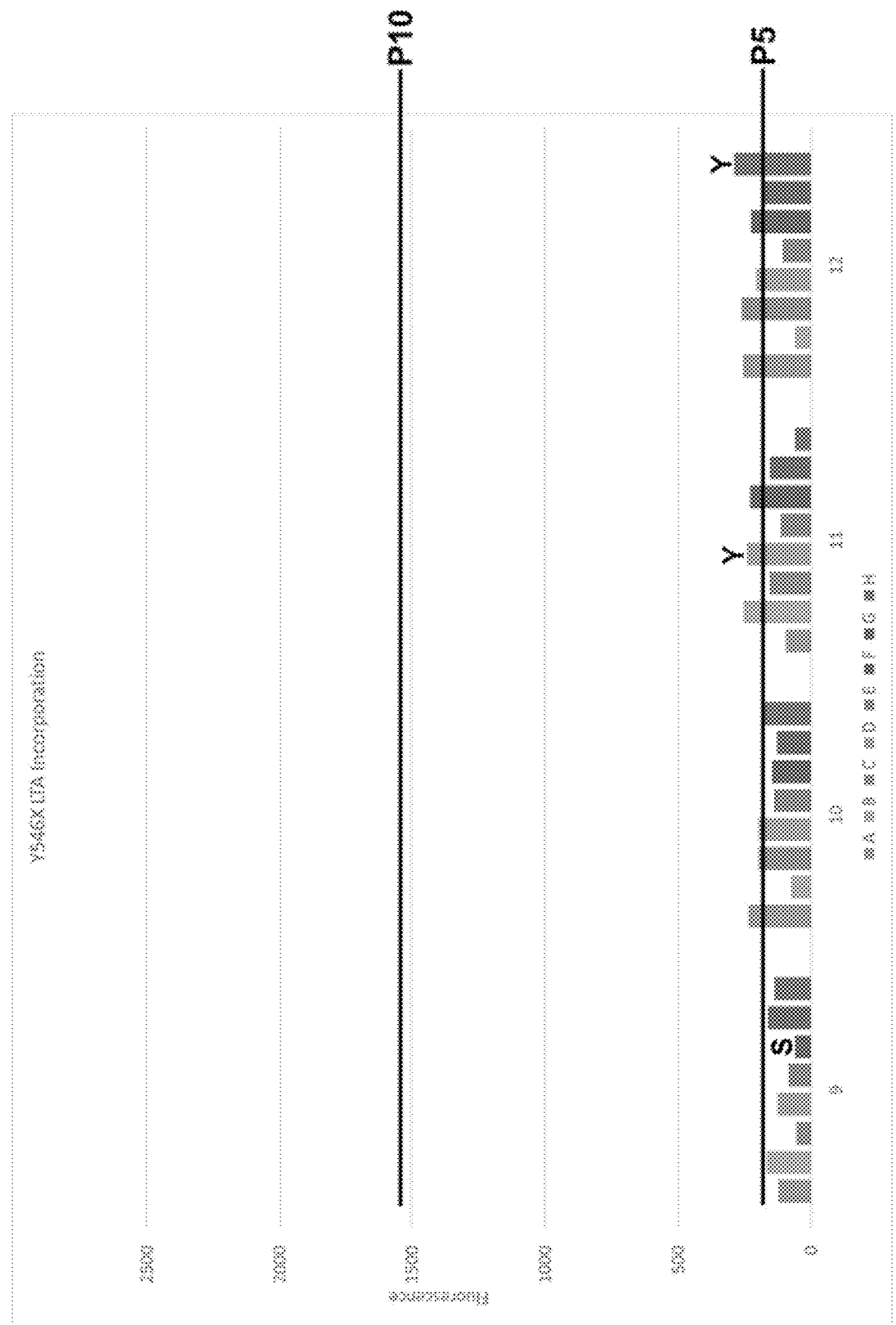
Figure 7B:
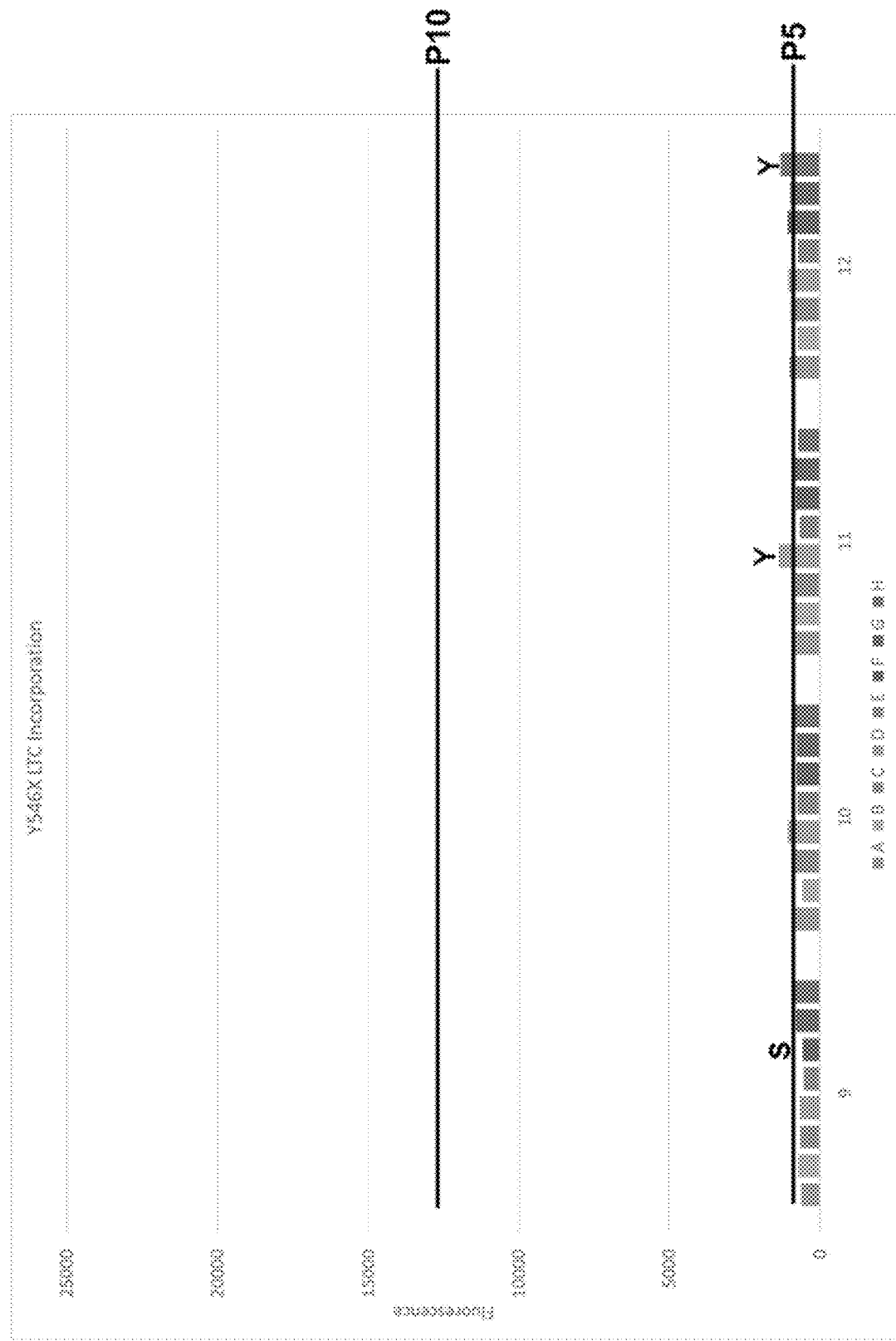

FIGS. 7A-7B show the lack of incorporation of reversible terminators by Y546X mutants (without A486L) tested in Example 6.

Figure 8:
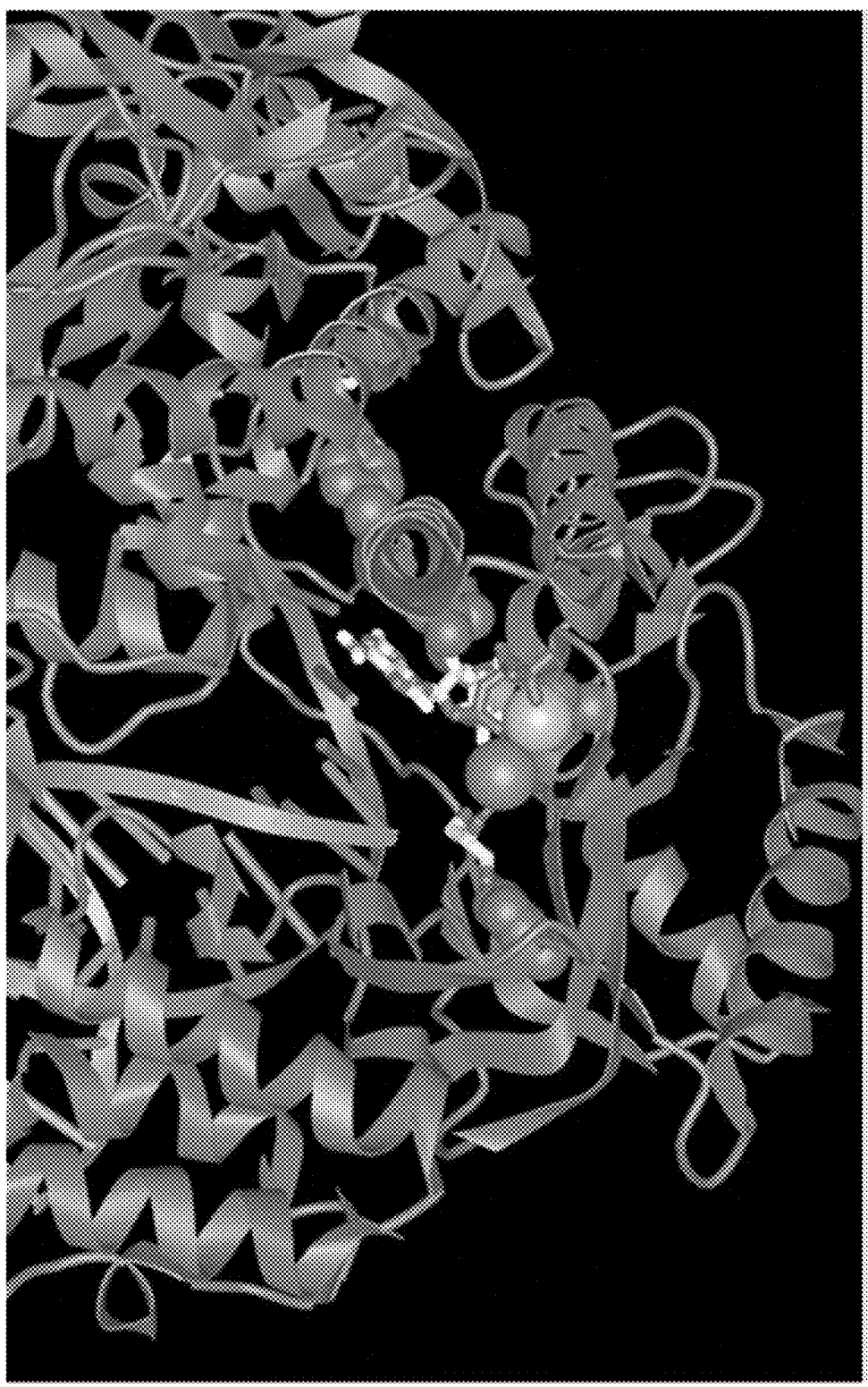

FIG. 8 illustrates a model of interaction between a mutant polymerase and a modified nucleotide.

Figure 9A:
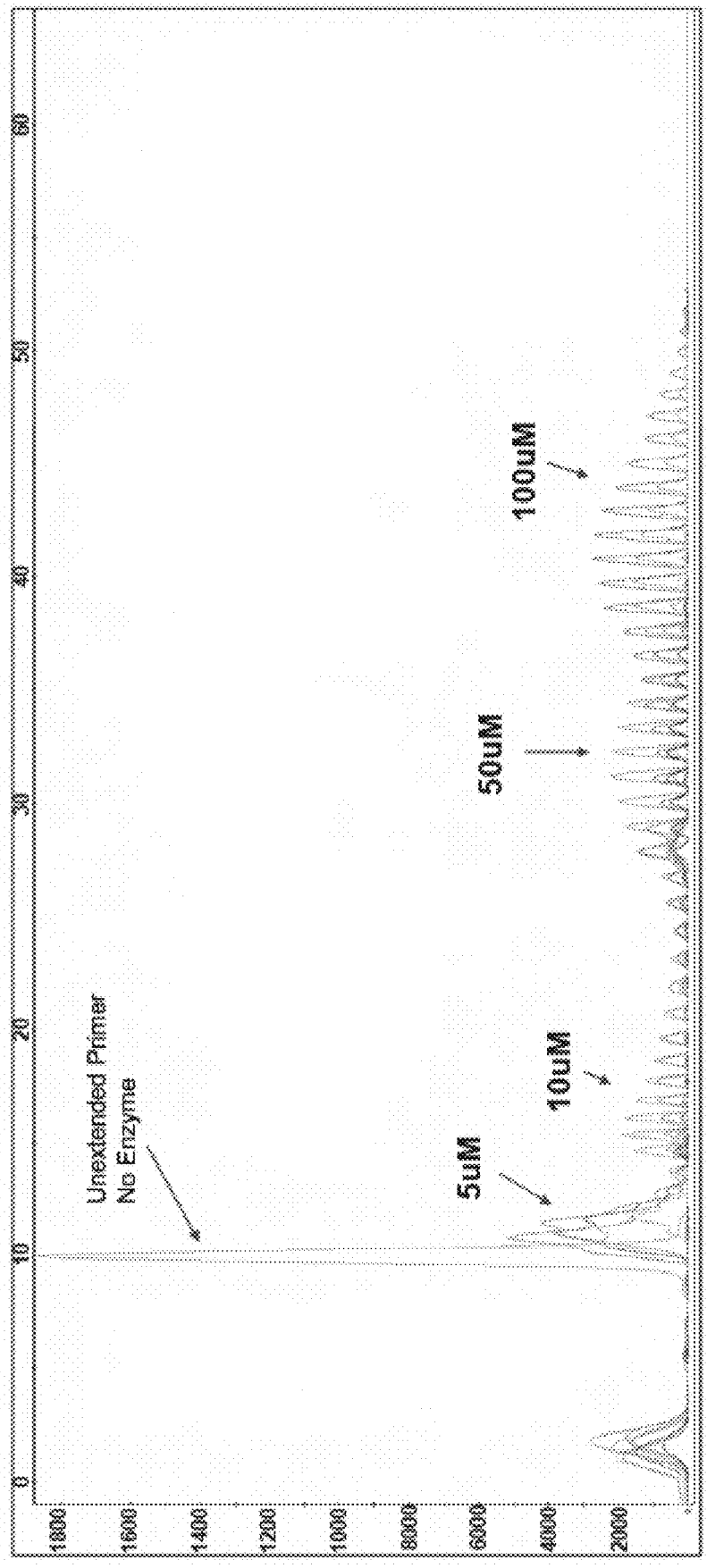
Figure 9B:
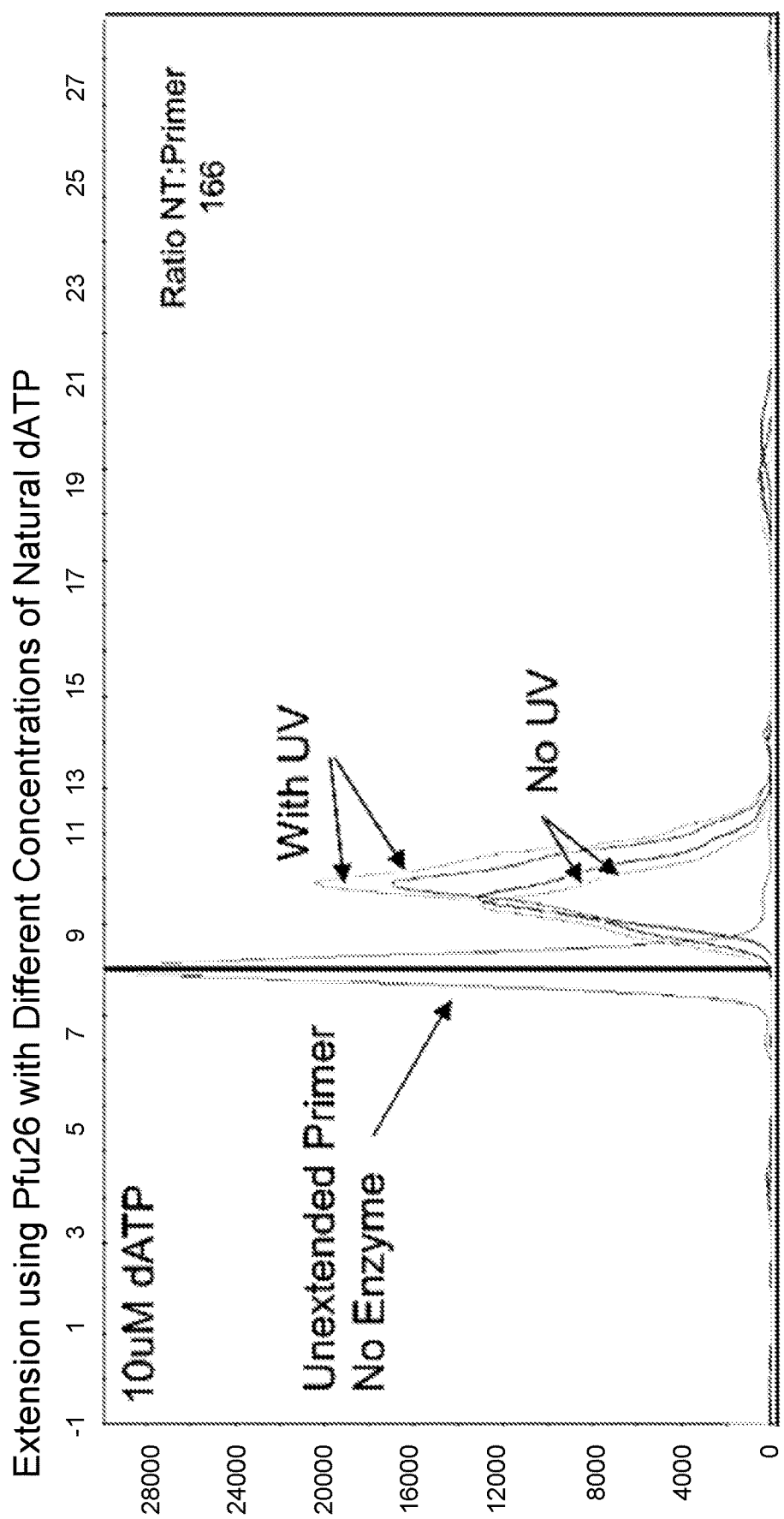
Figure 9B:
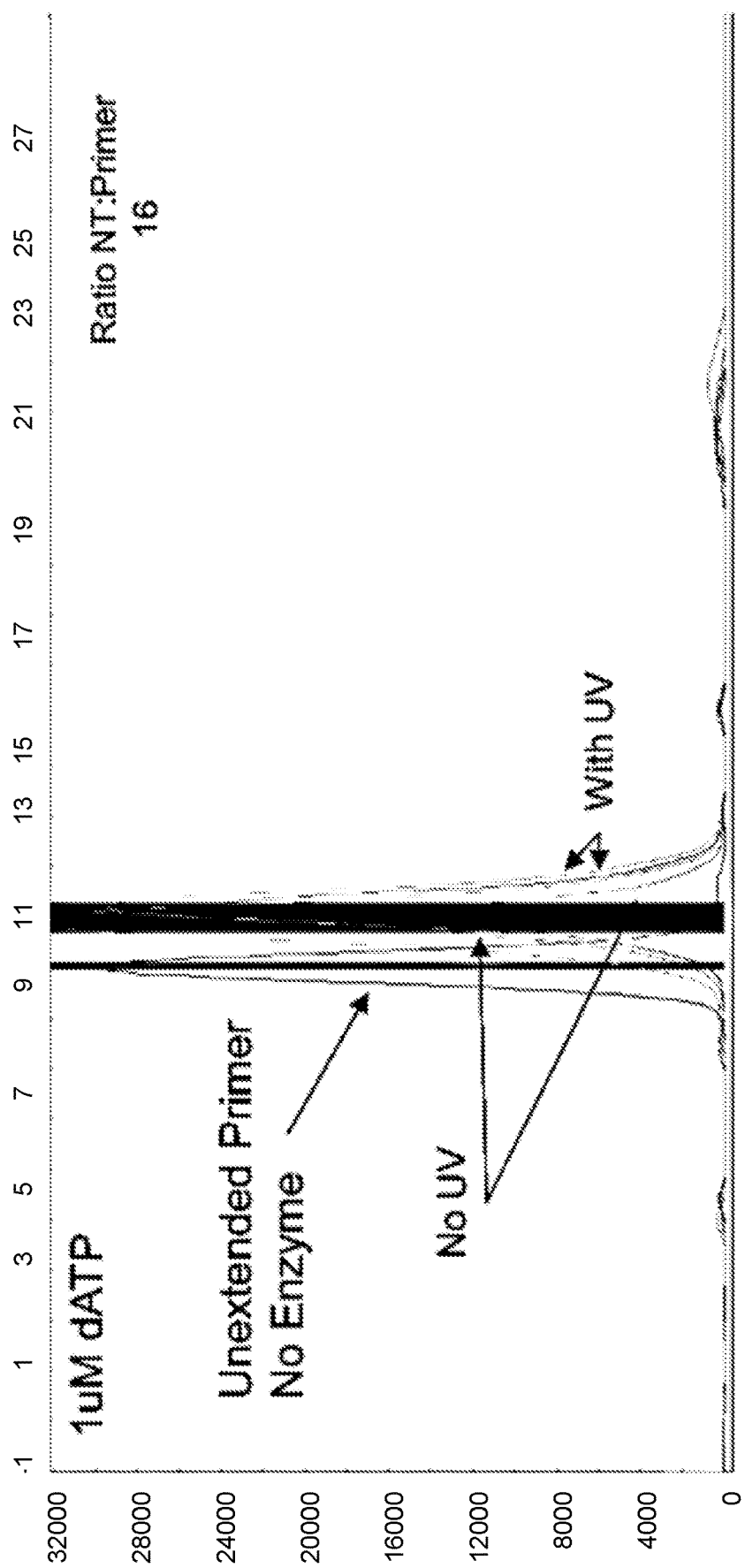
Figure 9B:
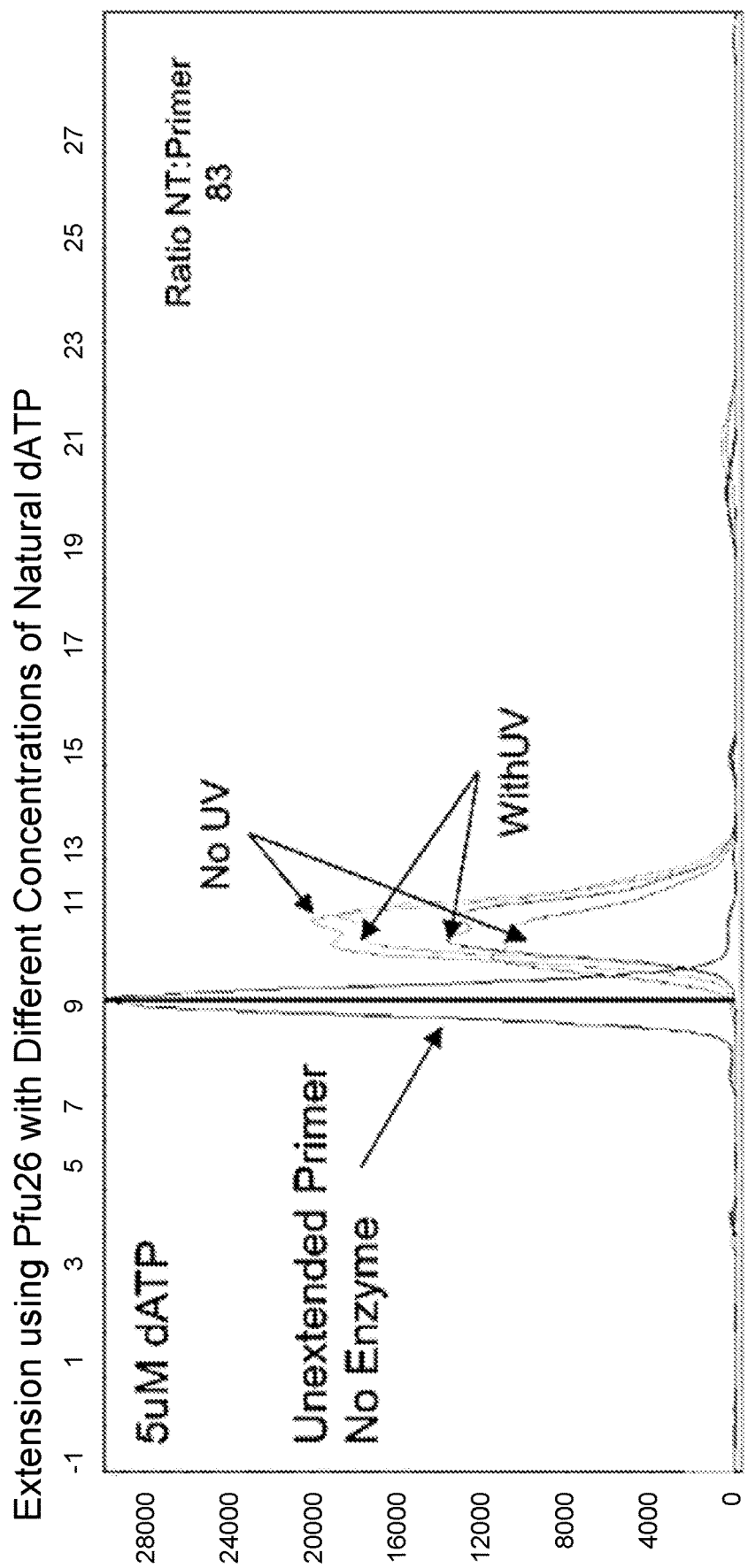
Figure 9C:
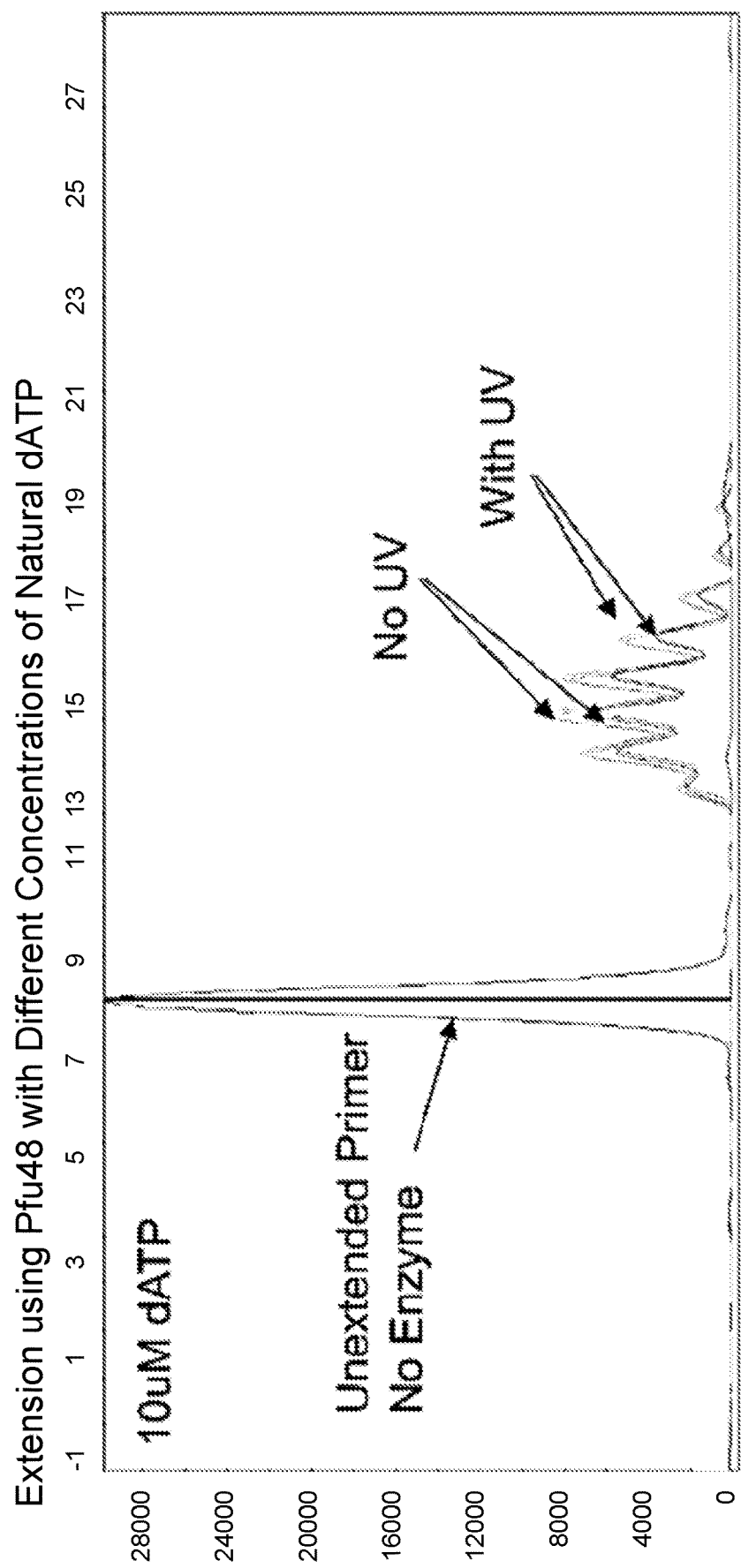
Figure 9C:
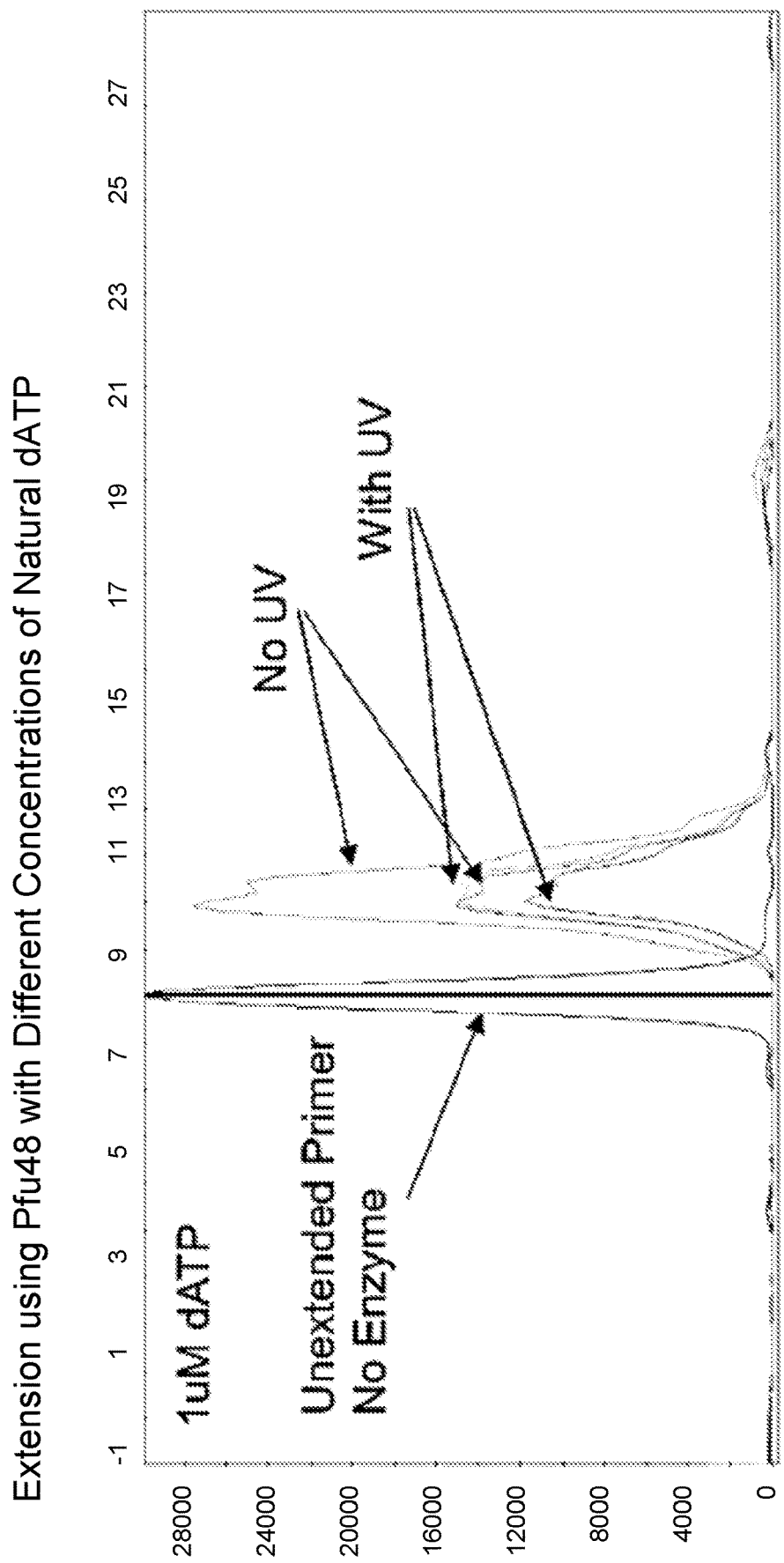
Figure 9C:
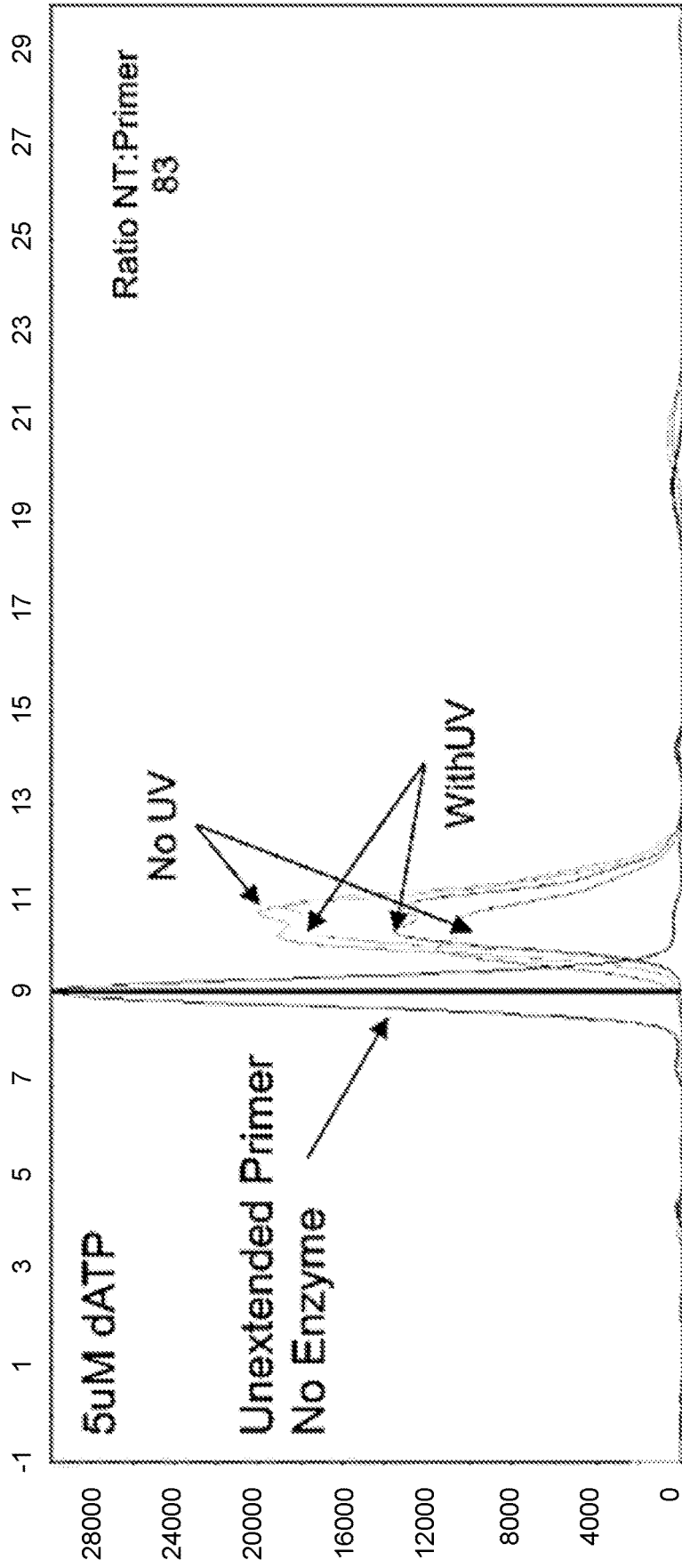

FIGS. 9A to 9C show measurements of template-independent incorporation of natural dATP by a commercially available preparation of TdT (Promega) and various mutant polymerases in Example 7.

FIGS. 10A to 10E show measurements of template-independent incorporation of reversible terminators to priming strands by a commercially available preparation of TdT (Promega) and various mutant polymerases in Example 8.

FIGS. 11A to 11F show measurements of template-independent incorporation of a reversible terminator by a commercially available preparation of TdT (Promega) in Example 9.

Figure 12A:
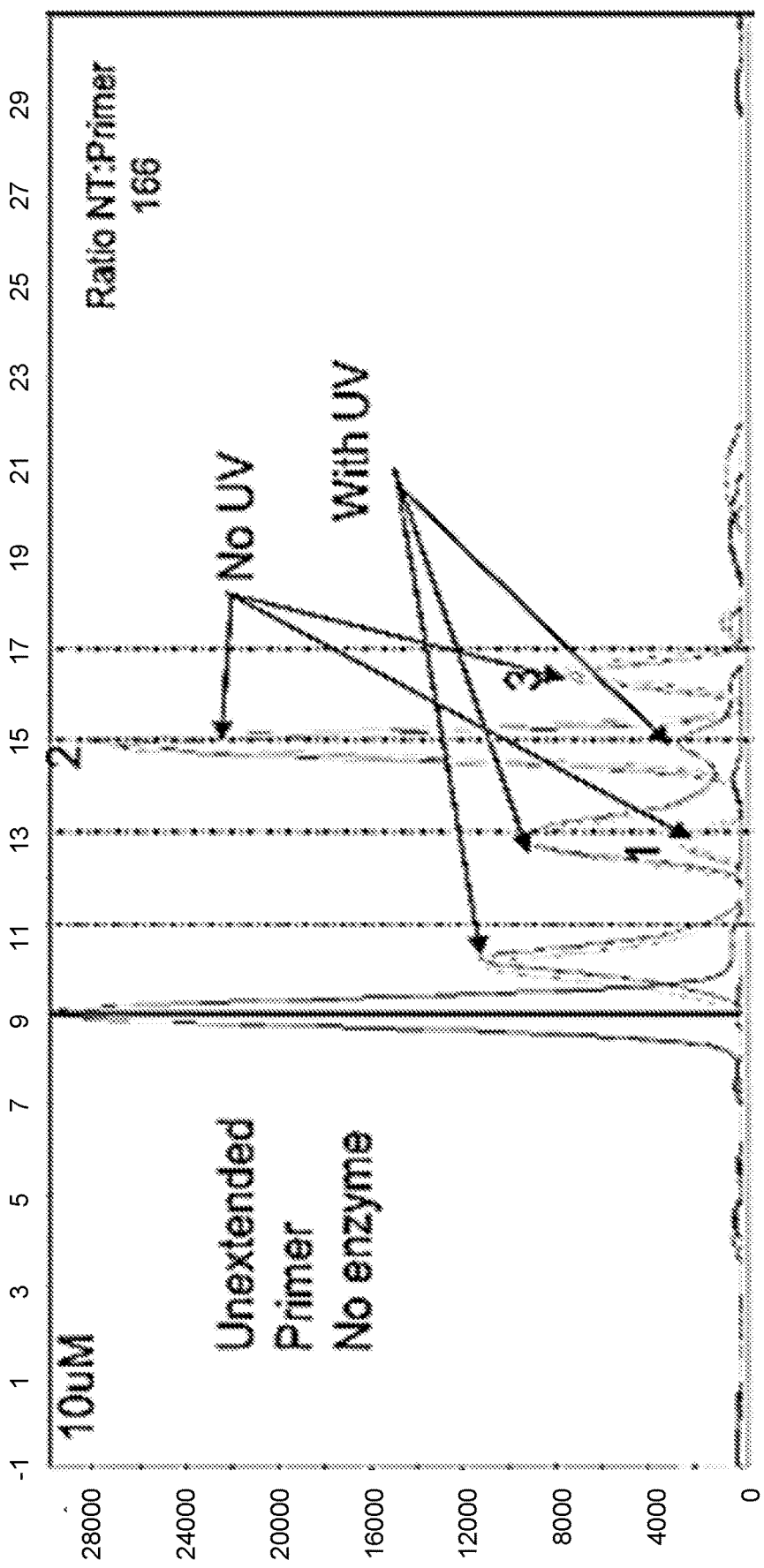
Figure 12A:
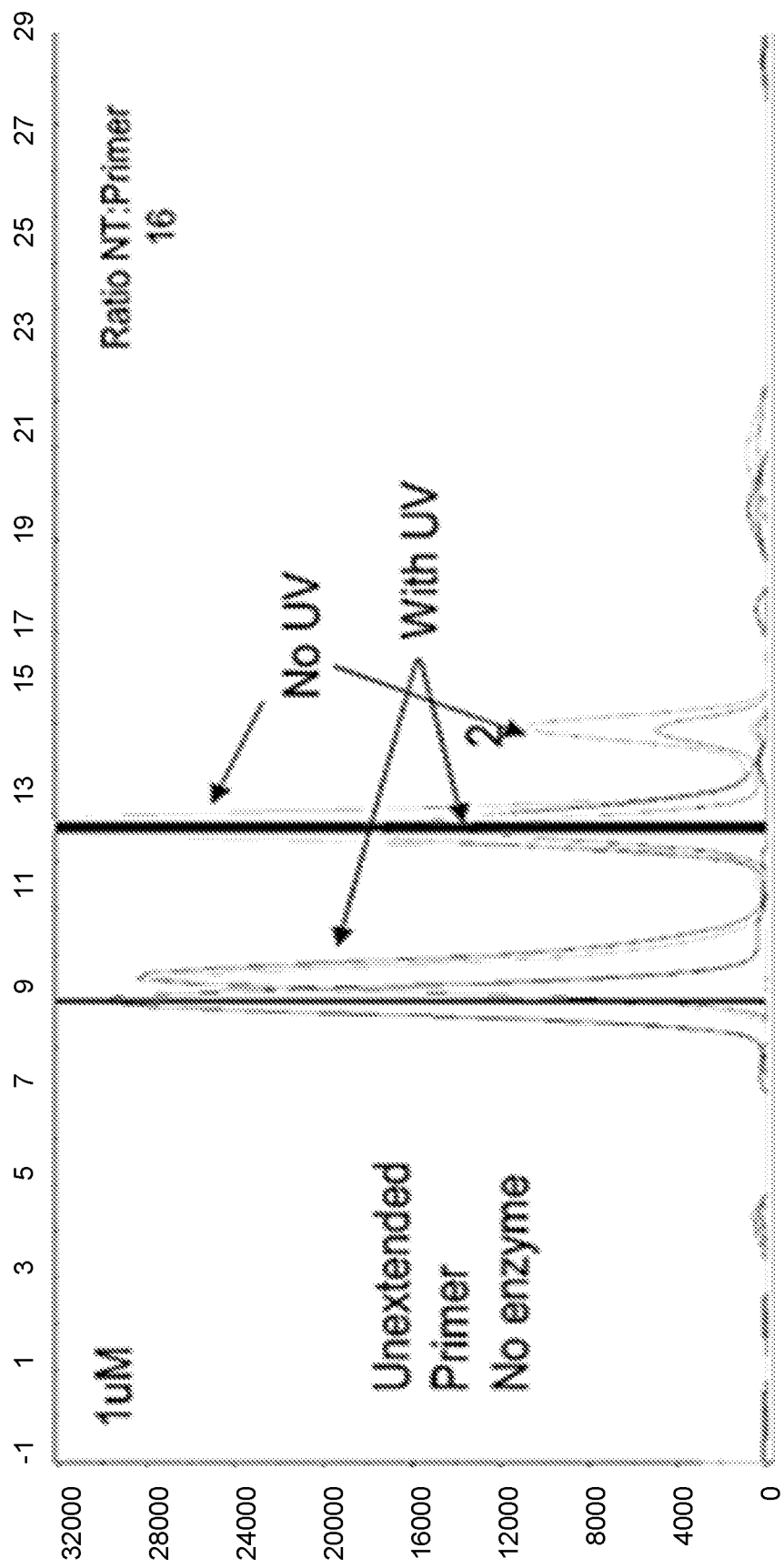
Figure 12A:
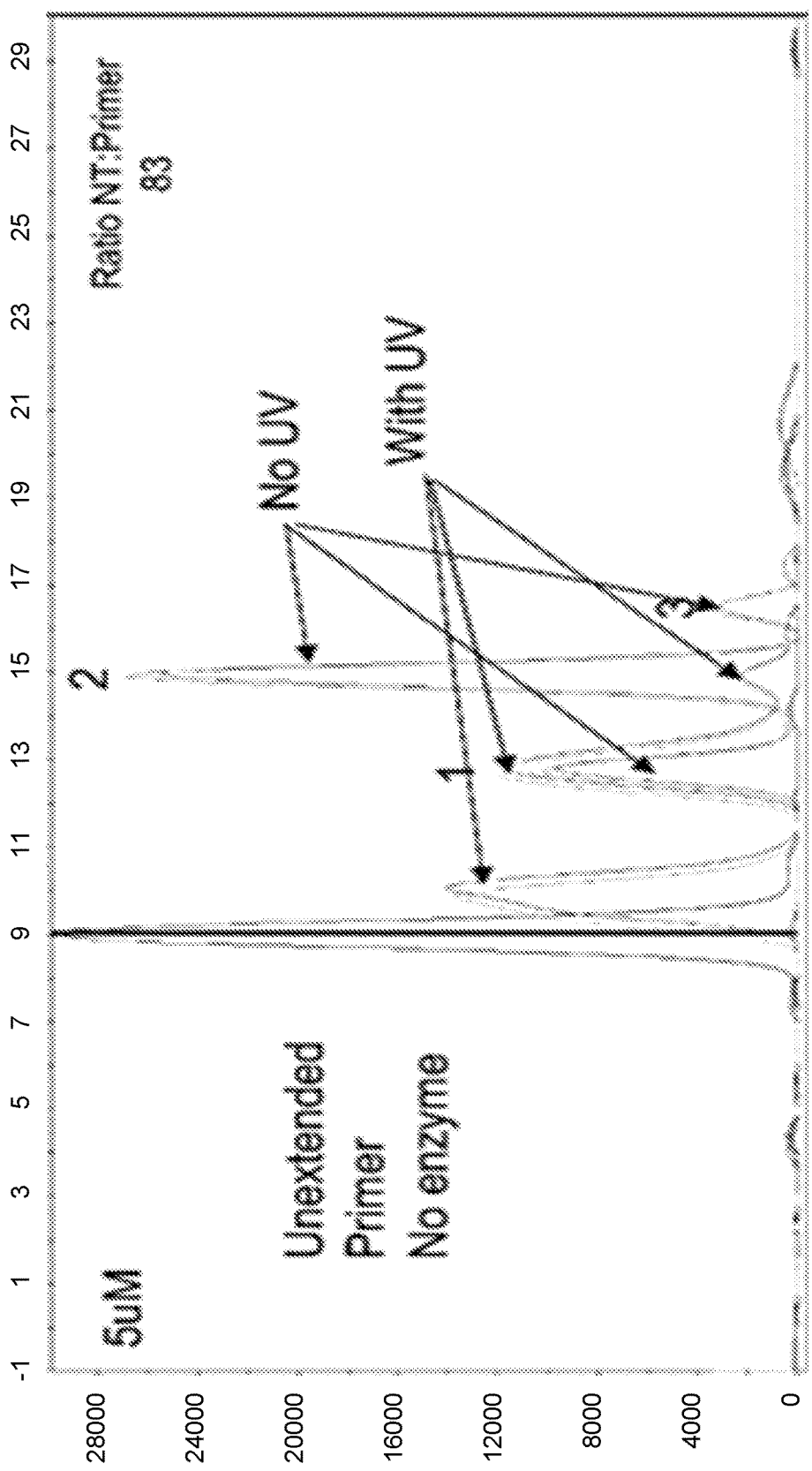
Figure 12B:
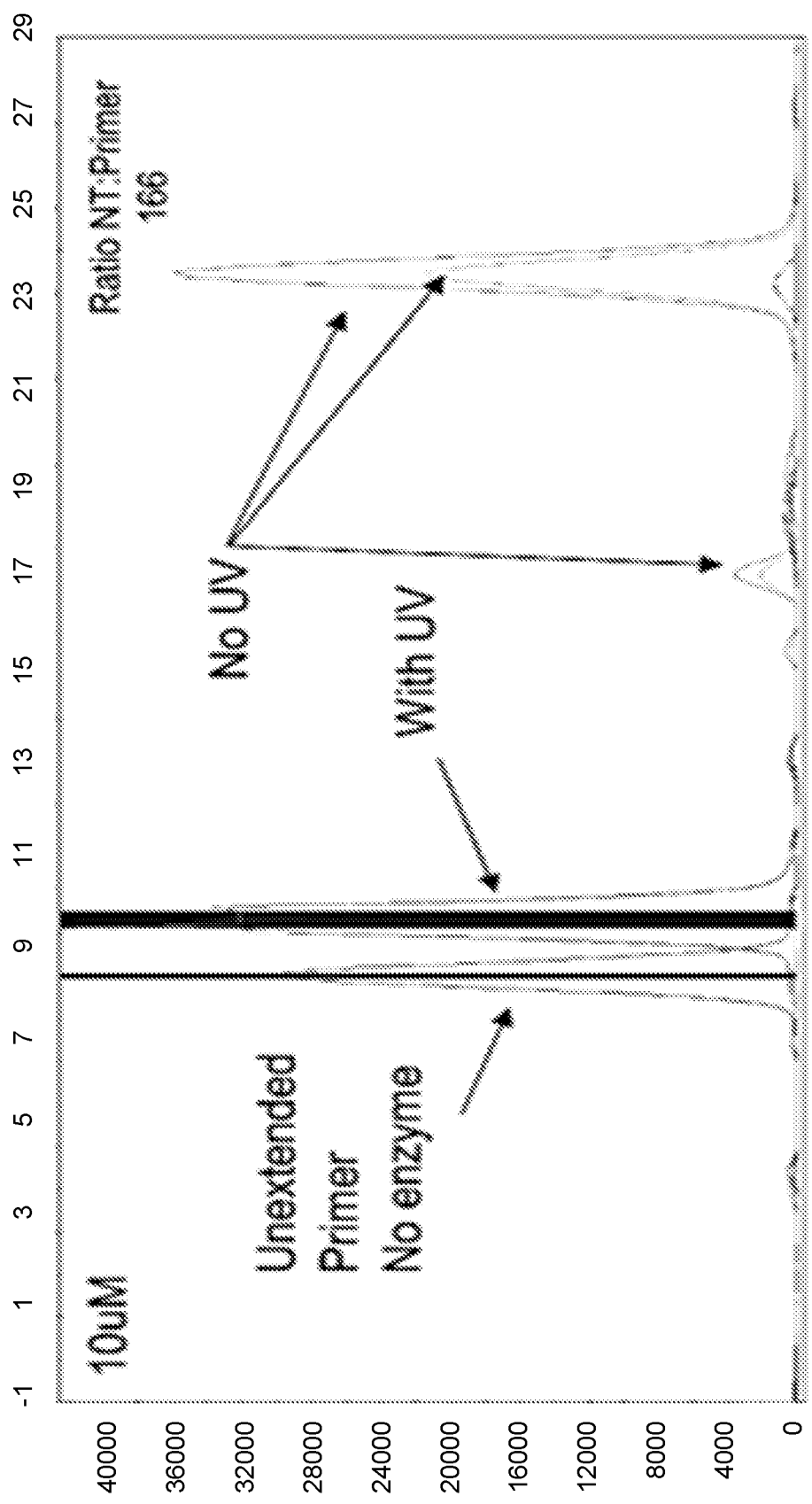
Figure 12B:
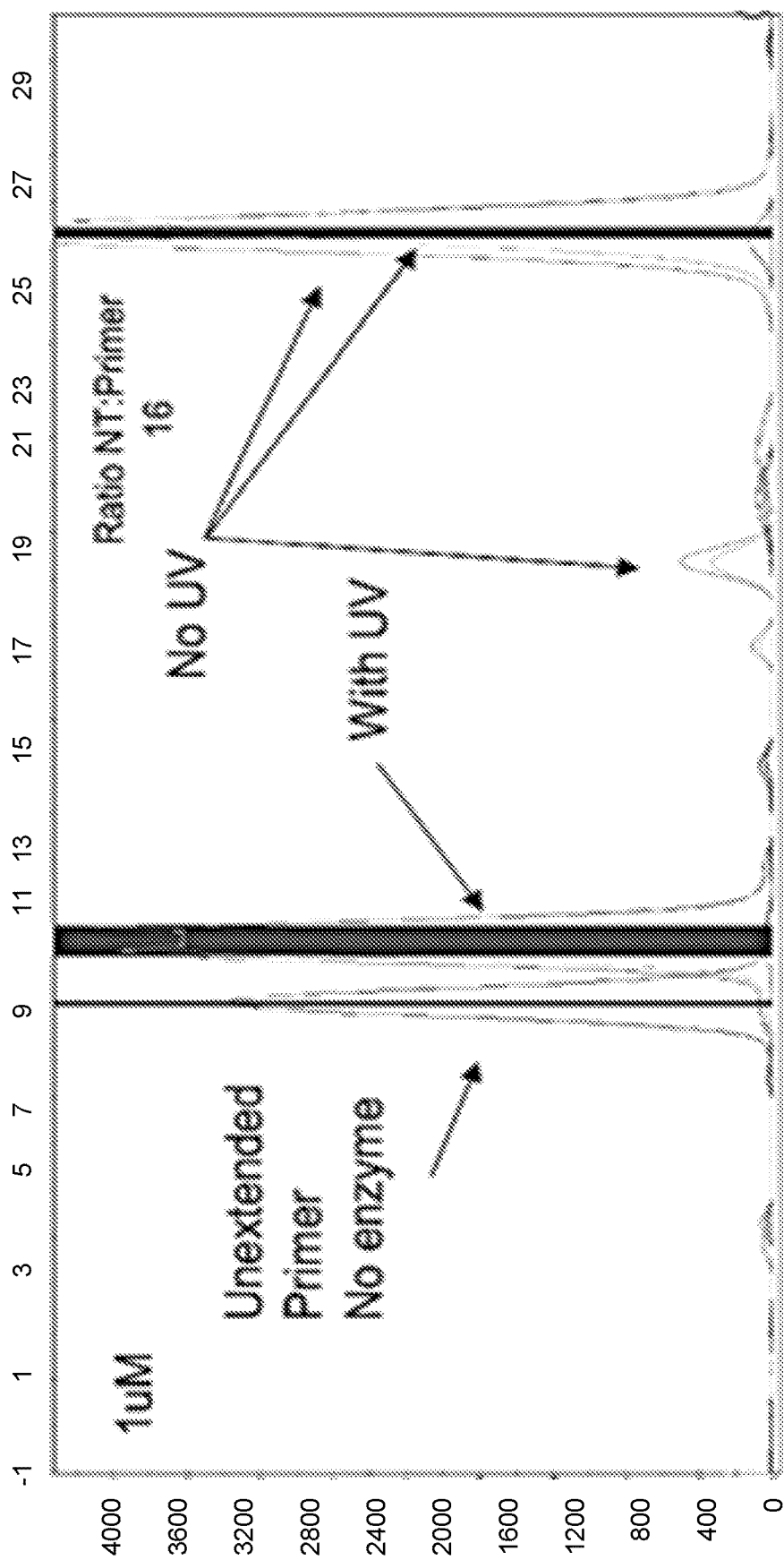
Figure 12B:
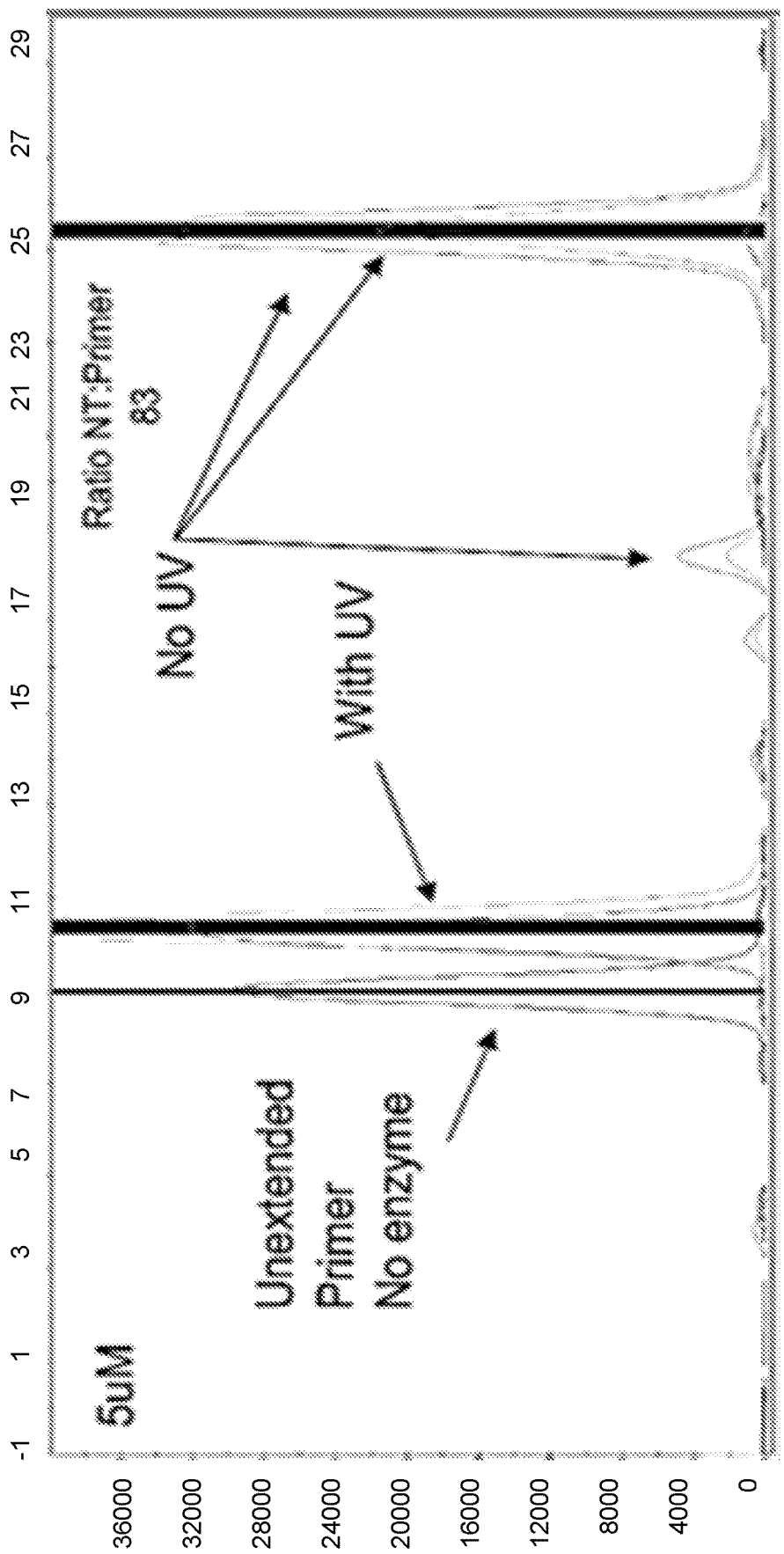

FIGS. 12A and 12B show measurements of template-independent incorporation of reversible terminators to priming strands by a mutant polymerase (Pfu26) in Example 9.

Figure 13A:
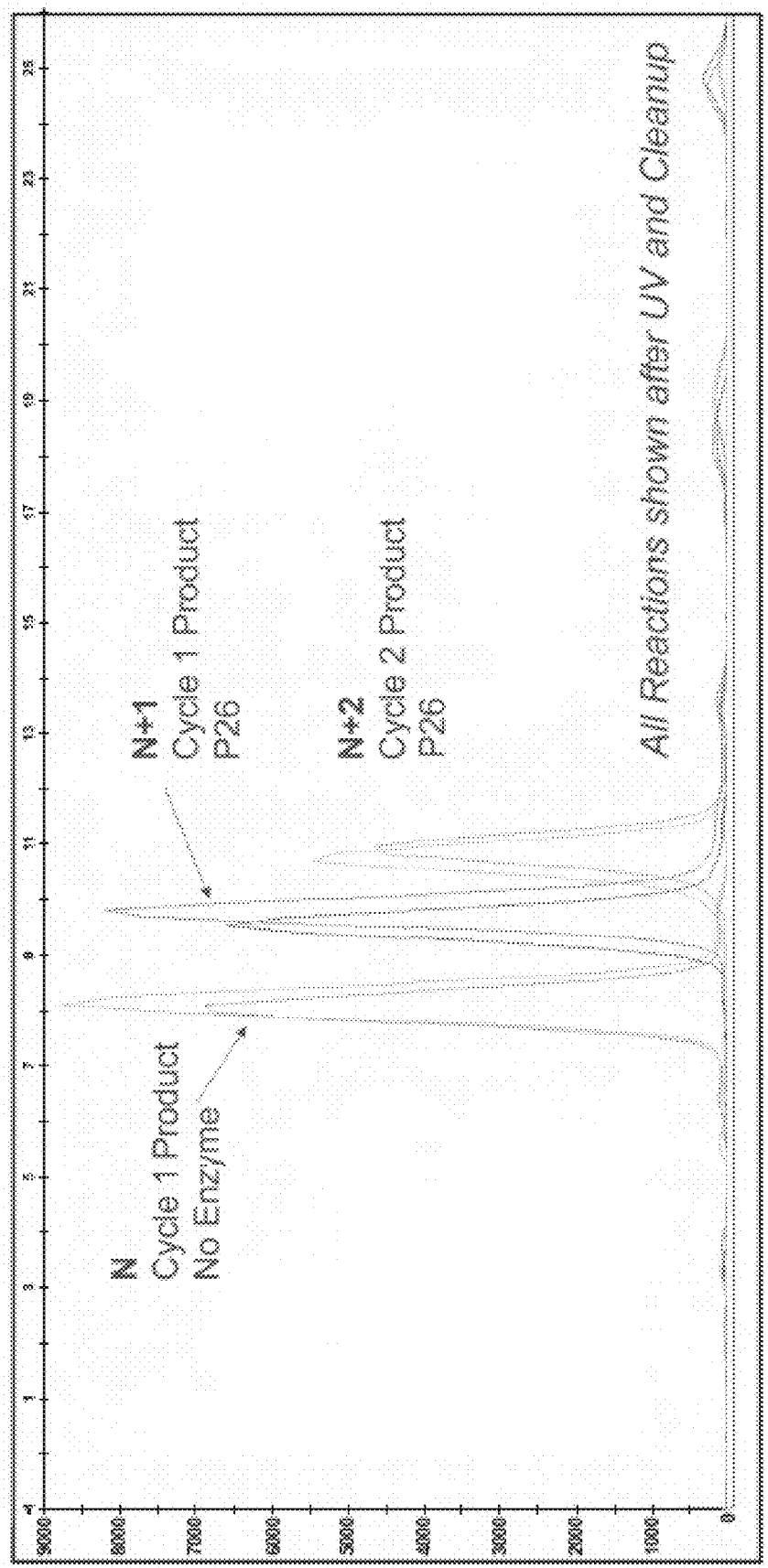
Figure 13B:
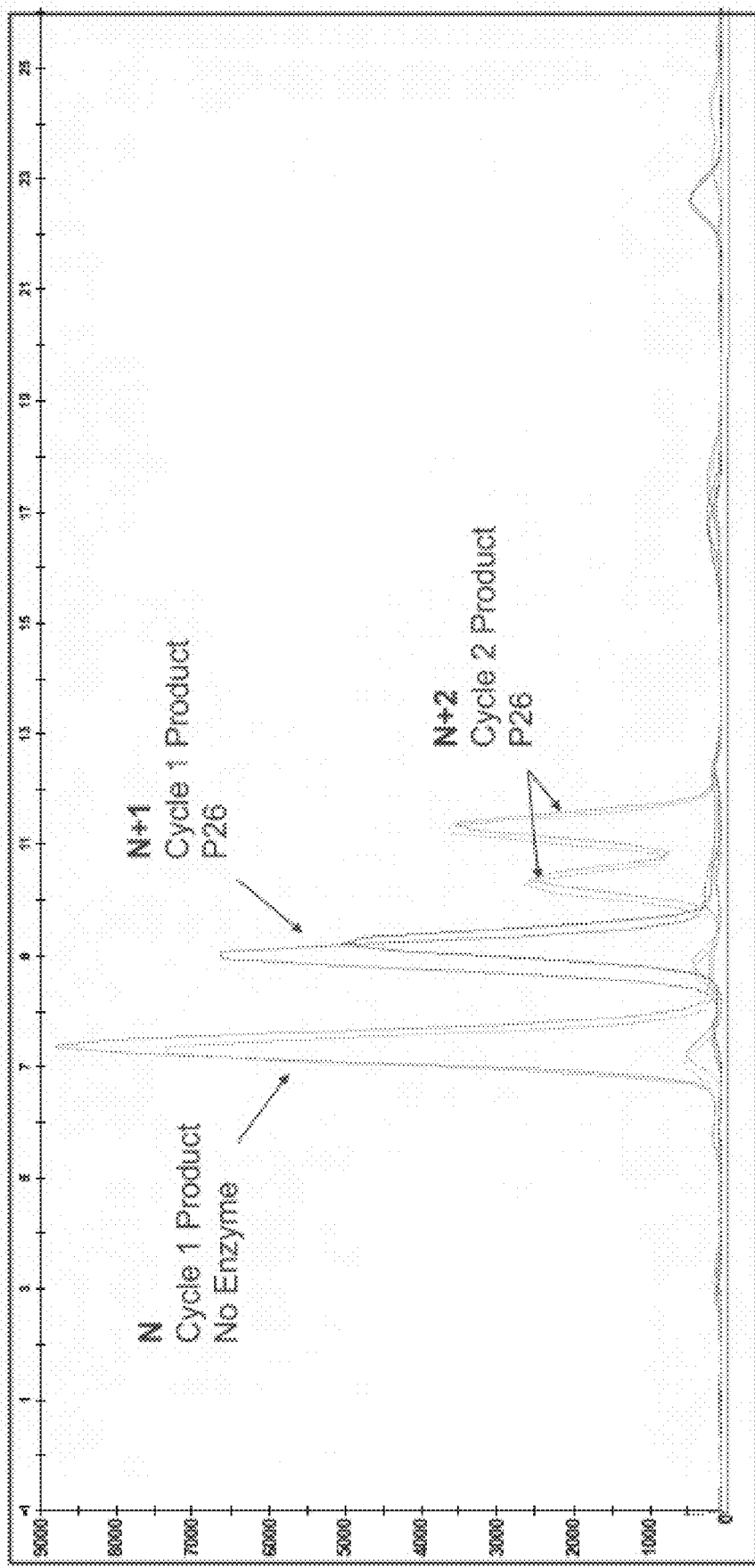
Figure 13C:
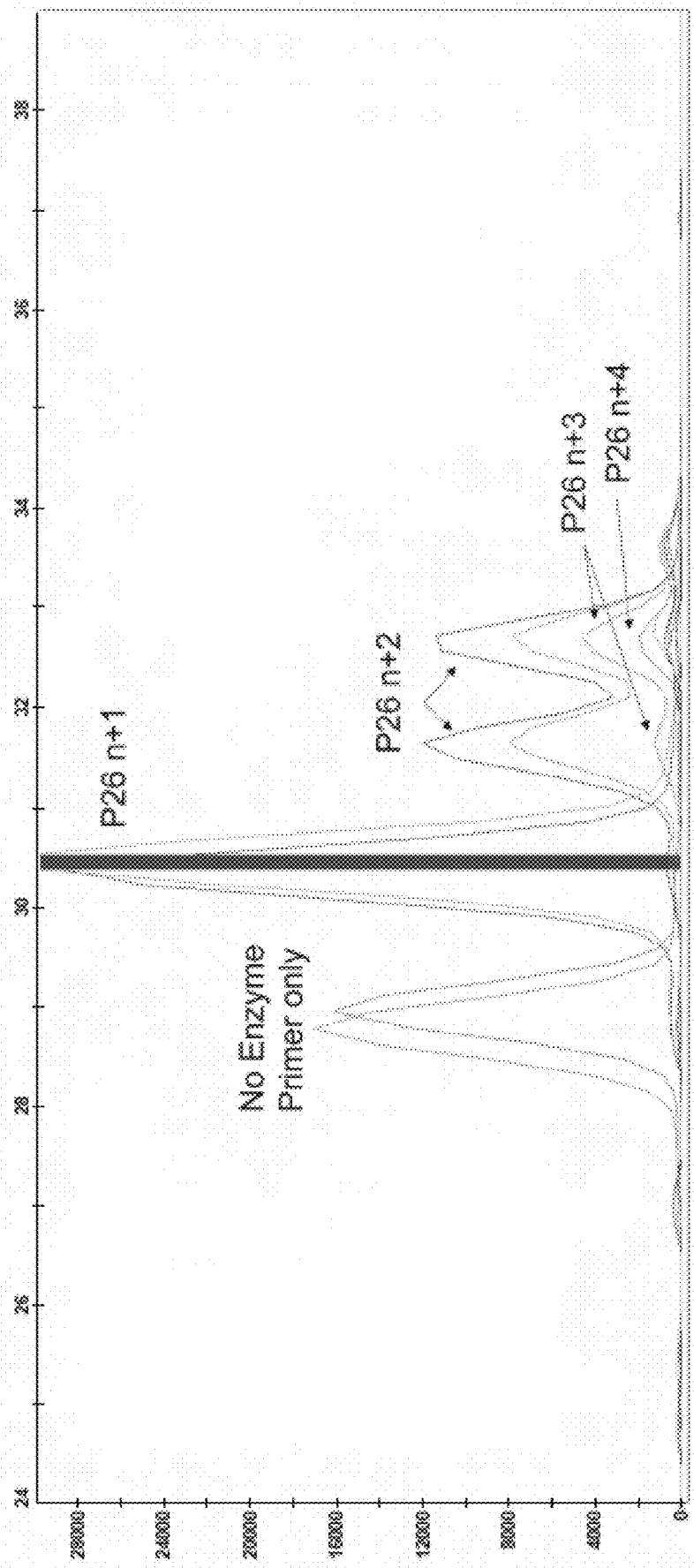

FIGS. 13A to 13C show measurements of the multi-cycle addition of a 3'-OH unblocked reversible terminator (LTA-2) by a mutant polymerase (Pfu26) in Example 10.

The present teachings are best understood from the following detailed description when read with the accompanying drawing figures. The features are not necessarily drawn to scale.

DETAILED DESCRIPTION

The present disclosure provides mutant polymerases for improved incorporation of 3'-OH unblocked reversible terminator nucleotides, such as Lightning Terminators. The present inventors have surprisingly identified certain mutant polymerases which exhibit improved incorporation of the reversible terminator and have a number of other associated advantages, such as improved sequencing performance and lower DNA binding affinity.

The present disclosure also provides nucleic acid molecules encoding the mutant polymerases described herein. Such nucleic acid molecules can be readily envisioned based upon the amino acid sequences disclosed herein based on the known correspondence between codons and amino acids. The present disclosure also provides expression vectors comprising such nucleic acid molecules. The present disclosure also provides host cells comprising such expression vectors.

The present disclosure also provides methods for incorporating one or more reversible terminator nucleotides into a priming strand capable of acting as a point of incorporation of a nucleotide and being extended from its 3' end. The methods comprise allowing the following components to interact: (i) a mutant polymerase as described herein, (ii) a priming strand; and (iii) a nucleotide solution comprising a reversible terminator, such as a Lightning Terminator.

The present disclosure also provides a kit for performing a nucleotide incorporation reaction comprising a mutant polymerase as described herein and a nucleotide solution. In some embodiments, the nucleotide solution comprises 3'-OH unblocked reversible terminators.

The mutant polymerases described herein are improved for incorporation of modified nucleotides, especially 3'-OH unblocked reversible terminators. The present inventors have identified certain mutant polymerases which exhibit improved incorporation of the reversible terminators and have a number of other associated advantages, including lower DNA binding affinity and improved sequencing metrics in sequencing-by-synthesis reactions. Lower binding affinity will allow the mutant polymerases to rapidly cycle between extended and unextended primary strands, which is expected to produce higher incorporation efficiency compared to polymerases with higher affinity.

As described in greater detail hereinbelow, it has been found that one or more mutations to one or more residues in the polymerase result in profound increases in turnover rate and reduction in pyrophosphorolysis. These mutant polymerases have improved performance in DNA sequencing by synthesis (SBS) and result in reduced phasing and/or pre-phasing, and overall improved quality metrics in sequencing by synthesis reactions. "Phasing" refers to a loss of synchronicity within a cluster during SBS due to failure to incorporate a nucleotide in some strands within that cluster during a sequencing cycle. "Pre-phasing" refers to a situation in an SBS cluster where nucleotides without effective 3' terminators are incorporated in some strands, causing them to advance 1 cycle ahead of the result of the cluster.

In some embodiments, the mutant polymerase comprises an amino acid sequence that is at least 60%, 70%, 80%, 85%, 90%, 95%, 96%, 97%, 98%, or 99% identical to SEQ ID NO: 1, which recombinant DNA polymerase comprises at least one amino acid mutation at one or more positions functionally equivalent to certain positions in the Pfu DNA polymerase amino acid sequence. The wild type Pfu DNA polymerase amino acid sequence is set forth in SEQ ID NO: 1.

In some embodiments, the present mutant polymerases comprise an amino acid sequence that is at least 80%, 85%, 90%, 95%, 96%, 97%, 98%, or 99% identical to SEQ ID NO:1, and also comprises at least one amino acid mutation at one or more positions functionally equivalent to amino acid positions residues at 409, 477, 486 or 546 in Pfu polymerase. In some embodiments, the polymerase comprises a mutation at a position functionally equivalent to position 486 in Pfu polymerase, and may further comprises a mutation at a position functionally equivalent to position 546 in Pfu polymerase, and still further may comprises a mutation at a position functionally equivalent to position 477 in Pfu polymerase. In some embodiments, the mutant polymerases are at least 96% identical to SEQ ID NO:2 and comprise mutation A486X, where X can be any amino acid except alanine. For instance, the mutant polymerase may comprise the amino acid sequence of SEQ ID NO:1 with mutations Y546H, K477W, and A486X, where X can be any amino acid except alanine. In some embodiments, the mutant polymerase also comprises mutations D141A and E143A.

In some embodiments, the mutant polymerase further comprises one or more mutations at positions functionally equivalent to positions 270, 330, 332, 333, 409, 451, 453, 457, 476, 489, 490, 492, 494, 497, and 581 in Pfu polymerase. In some embodiments, the mutant polymerase does not comprise a mutation at any position functionally equivalent to positions 266, 267, 268, 269, 329, 336, 399, 400, 403, 404, 407, 408, 410, 411, 450, 452, 455, 456, 458, 459, 460, 461, 462, 463, 464, 465, 466, 475, 477, 478, 479, 480, 481, 482, 483, 485, 487, 488, 491, 493, 495, 496, 498, 499, 500, 515, 522, 545, 546, 577, 579, 580, 582, 584, 591, 595, 603, 606, 607, 608, 612, 613, 614, 664, 665, 666, 668, 669, 674, 675, and 676 in Pfu polymerase.

The mutant polymerases described hereinabove can comprise additional mutations that are known to enhance one or more aspects of polymerase activity in the presence of 3' blocked nucleotides and/or in DNA sequencing applications.

In some embodiments, the mutant polymerase comprises reduced exonuclease activity as compared to a wild type polymerase. For example, the mutant polymerase may comprise mutations at positions functionally equivalent to Asp141 and/or Glu143 in the amino acid sequence of the 9° N DNA polymerase.

In some embodiments, the mutant polymerase can comprise an additional mutation to remove an internal methionine. For example, in some embodiments, the mutant polymerase comprises a mutation to a different amino acid at the position functionally equivalent to Met129 in the Pfu and 9° N DNA polymerase amino acid sequences. In some embodiments, the mutant polymerase comprises a mutation functionally equivalent to Met129Ala the amino acid sequence of the Pfu and 9° N DNA polymerases.

In some embodiments, the mutation comprises a mutation to a residue having a non-polar side chain. Amino acids having non-polar side chains are well-known in the art and include, for example: alanine, cysteine, glycine, isoleucine, leucine, methionine, phenylalanine, proline, tryptophan, tyrosine and valine.

In some embodiments, the mutation comprises a mutation to a residue having a polar side chain. Amino acids having polar side chains are well-known in the art and include, for example: arginine, asparagine, aspartic acid, glutamine, glutamic acid, histidine, lysine, serine and threonine.

In some embodiments, the mutation comprises a mutation to a residue having a hydrophobic side chain. Amino acids having hydrophobic side chains are well-known in the art and include, for example: glycine, alanine, valine, leucine, isoleucine, proline, phenylalanine, methionine, and tryptophan.

In some embodiments, the mutation comprises a mutation to a residue having an uncharged side chain. Amino acids having uncharged side chains are well-known in the art and include, for example: glycine, serine, cysteine, asparagine, glutamine, tyrosine, and threonine.

In some embodiments, the mutant polymerase is a derivative of a DNA polymerase. In some embodiments, the DNA polymerase is an archaeal DNA polymerase. In some embodiments, the DNA polymerase is a family B DNA polymerase. Family B archaeal DNA polymerases are known in the art as exemplified by the disclosure of Arezi et al., U.S. Pat. App. Pub. No. 20030228616. In some embodiments the archael DNA polymerase is from hyperthermophilic archea, which means that the polymerases are often thermostable. Accordingly, in a further preferred embodiment the mutant polymerase is derived from a DNA polymerase selected from Vent, Deep Vent, 9° N and Pfu polymerase. Vent and Deep Vent are commercial names used for family B DNA polymerases isolated from the hyperthermophilic archaea *Thermococcus litoralis* and *Pyrococcus* sp. GB-D, respectively. 9° N polymerase was also isolated from a unique *Thermococcus* species (T sp. 9° N). As discussed above, Pfu polymerase was isolated from *Pyrococcus furiosus*. In some embodiments, the present mutant polymerase is a derivative of a *Pyrococcus* polymerase or a *Thermococcus* polymerase.

In some embodiments, the family B archaeal DNA polymerase is from a genus such as, for example those of the genuses *Thermococcus*, *Pyrococcus* or *Methanococcus*. Members of the genus *Thermococcus* include, but are not limited to *Thermococcus* 4557, *Thermococcus barophilus*, *Thermococcus gammatolerans*, *Thermococcus onnurineus*, *Thermococcus sibiricus*, *Thermococcus kodakarensis*, *Thermococcus gorgonarius*. Members of the genus *Pyrococcus* include, but are not limited to *Pyrococcus* NA2, *Pyrococcus abyssi*, *Pyrococcus furiosus*, *Pyrococcus horikoshii*, *Pyrococcus yayanosii*, *Pyrococcus endeavori*, *Pyrococcus glycovorans*, *Pyrococcus woesei*. Members of the genus *Methanococcus* include, but are not limited to *Methanococcus aeolicus*, *Methanococcus maripaludis*, *Methanococcus vannielii*, *Methanococcus voltae*, *Methanococcus thermolithotrophicus* and *Methanococcus jannaschii*.

For example, the polymerase can be selected from the group consisting of Vent, Deep Vent, 9° N, and Pfu polymerase. In some embodiments, the family B archaeal DNA polymerase is Pfu polymerase. Additional information regarding Pfu polymerases may be found in U.S. Pat. Nos. 5,789,166; 5,932,419; 5,948,663; 6,183,997; 6,391,548; 6,444,428; 6,734,293; 7,132,265; and 7,176,004. Other polymerases from *Pyrococcus* strains such as "Deep Vent" (Q51334) from strain GB-D and Pwo DNA polymerase may also be used.

Terminology

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The term "nucleic acid" and "polynucleotide" are used interchangeably herein to describe a polymer of any length, e.g., greater than about 10 bases, greater than about 100 bases, greater than about 500 bases, greater than 1000 bases, up to about 10,000 or more bases, composed of nucleotides, e.g., deoxyribonucleotides or ribonucleotides, or compounds produced synthetically which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine and uracil (G, C, A, T, and U respectively).

The term "nucleoside" as defined herein is a compound including a purine, deazapurine, or pyrimidine base linked to a sugar or a sugar substitute, such as a carbocyclic or acyclic linker at the 1' position or equivalent position and includes 2'-deoxy and 2'-hydroxyl, 2',3'-dideoxy forms, as well as other substitutions.

The term "nucleoside polyphosphate" as used herein refers to a phosphate ester of a nucleoside, with two or more phosphate groups. Deoxyadenosine triphosphate is an example of a nucleoside polyphosphate. Nucleoside polyphosphates may contain chemical groups attached to the terminal phosphate or to internal phosphates. For example, nucleoside polyphosphates may include molecules with an electrochemical label, mass tag, charge blockade label, or a chromogenic label, chemiluminescent label, fluorescent dye, or fluorescence quenching label attached to the terminal phosphate or to an internal phosphate in a polyphosphate chain. Further examples of chemical groups that may be used as labels include chromophores, enzymes, antigens, heavy metals, magnetic probes, phosphorescent groups, radioactive materials, scattering or fluorescent nanoparticles, Raman signal generating moieties, and electrochemical detection moieties. Additionally, the term "nucleoside polyphosphate" as used herein refers to a phosphate ester of a nucleoside, which may comprise sulfur atoms, imido groups or other modifications to the phosphate chain.

The term "nucleotide" as used herein refers to a phosphate ester of a nucleoside, wherein the esterification site typically corresponds to the hydroxyl group attached to the C-5 position of a pentose sugar or sugar substitute. In some cases nucleotides comprise nucleoside polyphosphates. However, the terms "added nucleotide," "incorporated nucleotide," "nucleotide added" and "nucleotide after incorporation" all refer to a nucleotide residue that is part of a oligonucleotide or polynucleotide chain.

The terms "nucleoside", "nucleotide", "deoxynucleoside", and "deoxynucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the "nucleoside", "nucleotide", "deoxynucleoside", and "deoxynucleotide" include those moieties that contain not only conventional ribose and deoxyribose sugars, but other sugars as well. Modified nucleosides, nucleotides, deoxynucleosides or deoxynucleotides also include modifications on the sugar moiety, e.g., wherein one or more of the hydroxyl groups are replaced with halogen atoms or aliphatic groups, or are functionalized as ethers, amines, or the like.

Naturally occurring nucleotides or nucleosides are defined herein as adenosine (A), thymidine (T), guanosine (G), cytidine (C), and uridine (U). It is recognized that certain modifications of these nucleotides or nucleosides occur in nature. However, modifications of A, T, G, and C that occur in nature that affect hydrogen bonded base pairing are considered to be non-naturally occurring. For example, 2-aminoadenosine is found in nature, but is not a "naturally occurring" nucleotide or nucleoside as that term is used herein. Other non-limiting examples of modified nucleotides or nucleosides that occur in nature that do not affect base pairing and are considered to be naturally occurring are 5-methylcytosine, 3-methyladenine, O(6)-methylguanine, and 8-oxoguanine, etc. Nucleotides include any nucleotide or nucleotide analog, whether naturally-occurring or synthetic.

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can hybridize to the sequence of the other in an anti-parallel sense wherein the 3'-end of each sequence hybridizes to the 5'-end of the other sequence and each A, T, G, and C of one sequence is then aligned with a T, A, C, and G, respectively, of the other sequence.

The term "duplex" means at least two sequences that are fully or partially complementary undergo Watson-Crick type base pairing among all or most of their nucleotides so that a stable complex is formed. The terms "annealing" and "hybridization" are used interchangeably to mean the formation of a stable duplex.

The terms "hybridization", and "hybridizing", in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the hybridization of the two sequences. Increased stringency can be achieved by elevating the temperature, increasing the ratio of co-solvents, lowering the salt concentration, and the like.

The term "priming strand" means a nucleic acid, either enzymatically made or synthetic, that is capable of acting as a point of incorporation of a nucleotide and being extended from its 3' end. In some embodiments, a priming strand is a primer that forms a duplex with a template, and it is extended from its 3' end along the template by incorporation of nucleotides complementary to the template; the sequence of nucleotides added during the extension process is determined by the sequence of the template polynucleotide. In some embodiments, a priming strand is a nucleic acid capable of acting as a point of incorporation for a single-base extension reaction or assay, or for template-independent oligonucleotide synthesis. A priming stand serves as an initiation point for nucleotide incorporation catalyzed by either DNA polymerase, RNA polymerase or reverse transcriptase. A piming strand may be 2-1000 bases or more in length, e.g., 10-500 bases.

The term "template" denotes a nucleic acid molecule that can be used by a nucleic acid polymerase to direct the synthesis of a nucleic acid molecule that is complementary to the template according to the rules of Watson-Crick base pairing. For example, DNA polymerases utilized DNA to synthesize another DNA molecule having a sequence complementary to a strand of the template DNA. RNA polymerases utilize DNA as a template to direct the synthesis of RNA having a sequence complementary to a strand of the DNA template. DNA reverse transcriptases utilize RNA to direct the synthesis of DNA having a sequence complementary to a strand of the RNA template.

The phrase "primer extension conditions" denotes conditions that permit for polymerase mediated primer extension by addition of nucleotides to the end of the primer molecule using the template strand as a template.

The phrase "single-base extension" refers to a procedure in which a single reversible terminator nucleotide is incorporated into a priming strand. The present methods and compositions can be employed for single-base extension assays, which can be used to determine the identity of a nucleotide base at a specific position along a nucleic acid. For instance, a single-base extension assay can be used to identify a single-nucleotide polymorphism (SNP) or to measure DNA methylation levels.

If a primer "corresponds to" or is "for" a certain nucleic acid template, the primer base pairs with, i.e., specifically hybridizes to, that nucleic acid template. As will be discussed in greater detail below, a primer for a particular nucleic acid template and the particular nucleic acid template, or complement thereof, usually contain at least one region of contiguous nucleotides that is identical in sequence.

The terms "terminator" and "terminator nucleotide" are used interchangeably and refers to a nucleotide that cannot serve as a substrate for a nucleotide addition by a polymerase, or is otherwise resistant to extension. Dideoxynucleotides, 3' azido nucleotides, and 3' amino nucleotides are examples of terminator nucleotides, although many others are known. Other non-limiting examples include 3'-phosphate labeled nucleotides, or virtual terminator nucleotides.

The term "reversible terminator" refers to a terminator nucleotide whose inability to serve as a substrate for a nucleotide addition, or resistance to extension, is configured to be reversed. For instance, a reversible terminator may have a blocking moiety that can be removed so that the nucleotide becomes available as a substrate for a polymerase. In some cases, the blocking moiety is on the 3'-OH position of the nucleotide's sugar, and the nucleotide is referred to as a "3'-OH blocked nucleotide," and removal of the blocking moiety yields a 3'-OH.

Figure 1D:
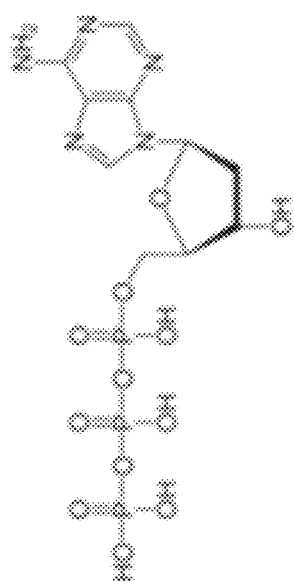
FIG. 1D shows natural dATP.
Figure 1F:
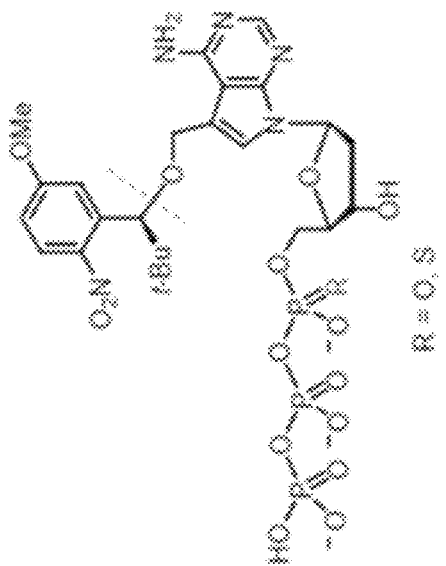
FIGS. 1E and 1F show reversible dATP terminators used for TiEOS with a 3'-OH unblocked reversible terminator.
Figure 1E:
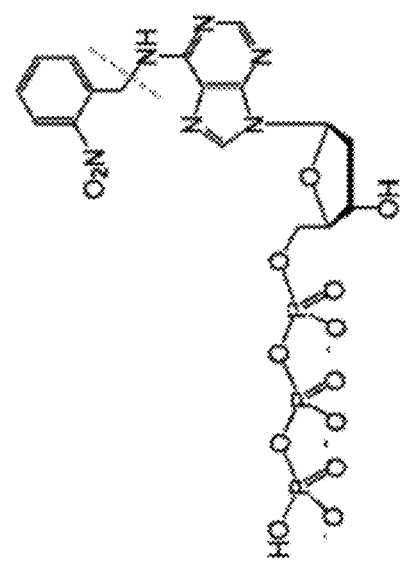

Alternatively, some reversible terminators do not have a blocking moiety on the 3'-OH position of the sugar, and such terminators are referred herein to as 3 '-OH unblocked reversible terminators. Lightning Terminators are an example of 3'-OH unblocked reversible terminators, in which the nucleotides are characterized by a free 3 '-OH on the ribose moiety and a photocleavable blocking group attached to purine (C7) or pyrimidine (C5) bases. FIGS. 1A, 1E and 1F provide illustrations of examples of Lightning Terminators. In some embodiments, the 3'-OH unblocked reversible terminators comprise a photocleavable blocking group. These reversible terminators can be incorporated into a strand but are blocked from extension during a period. After they are unblocked, they become capable of extension in a primer extension reaction. The 3'-OH unblocked reversible terminators comprise a photocleavable blocking group are substantially inactive with respect to PCR amplification until they are unblocked and activated by exposure to ultraviolet light or other photocleavage techniques. A wide variety of photocleavable blocking groups can be included in the later stage primers, such as those described in U.S. Pat. Nos. 8,969,535; 9,200,319; and 10,041,115. In some embodiments, the photocleavable blocking group has a blocking efficiency from about 90% to about 100%.

The photocleavable blocking groups are designed to reversibly block and terminate DNA synthesis, and then be cleaved efficiently by exposure to ultraviolet light, thereby actuating the primer. In some embodiments, the photocleavable blocking groups are in the form of nucleotide compounds containing the bases adenine, cytosine, guanine, thymine, uracil, or modified pyrimidine and purine derivatives thereof such as 7-hydroxyl-7-deaza-adenine/guanine. In other embodiments, the cleavable groups can be derivatized to include a reporter such as a dye. In some embodiments, the bases adenine, cytosine, guanine, thymine, uracil, or modified pyrimidine and purine derivatives thereof, can be covalently attached to a photocleavable protecting group such as a 2-nitrobenzyl group. In some embodiments, the 2-nitrobenzyl group is derivatized to enhance its termination of DNA synthesis. The photocleavable protecting group, such as the 2-nitrobenzyl group, also can be derivatized, in some embodiments, with a fluorescent dye by covalent linkage to the photocleavable protecting group.

In some embodiments, the photocleavable blocking groups comprise the base of the nucleoside covalently attached with a 2-nitrobenzyl group, and the alpha carbon position of the 2-nitrobenzyl group is optionally substituted with one alkyl or aryl group. In other embodiments, the 2-nitrobenzyl group is functionalized to enhance the termination and blocking properties as well as the light catalyzed deprotection rate. In other embodiments, the termination and blocking properties of the 2-nitrobenzyl and alpha carbon substituted 2-nitrobenzyl group attached to the base occur even when the 3'-OH group on the ribose sugar is unblocked. In some embodiments, the alpha carbon substituted 2-nitrobenzyl group also can be derivatized to include a selected fluorescent dye or other reporter.

The term "reporter" refers to a chemical moiety that is able to produce a detectable signal directly or indirectly. Examples of reporters include fluorescent dye groups, radioactive labels or groups effecting a signal through chemiluminescent or bioluminescent means. Examples of fluorescent dye groups include xanthene, fluorescein, rhodamine, BODIPY, cyanine, coumarin, pyrene, phthalocyanine, phycobiliprotein, ALEXA FLUOR 350, ALEXA FLUOR 405, ALEXA FLUOR 430, ALEXA FLUOR 488, ALEXA FLUOR 514, ALEXA FLUOR 532, ALEXA FLUOR 546, ALEXA FLUOR 555, ALEXA FLUOR 568, ALEXA FLUOR 568, ALEXA FLUOR 594, ALEXA FLUOR 610, ALEXA FLUOR 633, ALEXA FLUOR 647, ALEXA FLUOR 660, ALEXA FLUOR 680, ALEXA FLUOR 700, ALEXA FLUOR 750, and a squaraine dye. Examples of radioactive labels that may be used as reporters in some embodiments of the present invention, which are well known in the art such as 35S, 3H, 32P, or 33P.

The term "primer extension reagents" refers to any reagents that are required or suitable for performing a primer extension reaction (such as a polymerase chain reaction (PCR)) on a polynucleotide molecule such as a polynucleotide target. Primer extension reagents generally include primers, a thermostable polymerase or reverse transcriptase, and nucleotides in a mixture with an appropriate buffer such as Tris-HCl or other buffer. In some embodiments, the primer extension reagents can also include salts or ions, detergents, organic solvents, polymers and/or other additives. For example, the primer extension reagents may include ions (e.g., Mg2+, Mn2+ or K+) or salts thereof, a detergent such as Triton X-100, Tween 20, or NP40, serum or serum protein components such as bovine serum albumin (BSA), a polyol such as glycerol, mannitol or sorbitol, and/or a reducing agent (for example, dithiothreitol (DTT) or tris(2-carboxyethyl)phosphine (TCEP)). cDNA synthesis is primed by a reverse primer, annealed to the 3' polyA tail of an RNA transcript (oligo(dT)), or to multiple sequence-specific sites within the RNA (randomers, target specific primers).

The term "functionally equivalent" in the context of comparing two or more polymerases, means a polymerase contains an amino acid that is considered to occur at the amino acid position in the other polymerase that has the same functional role in the polymerase. As an example, the mutation at position 412 from Tyrosine to Valine (Y412V) in the Vent DNA polymerase would be functionally equivalent to a substitution at position 409 from Tyrosine to Valine (Y409V) in the 9° N polymerase. Generally, functionally equivalent mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different polymerases on the basis of sequence alignment and/or molecular modelling.

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using a suitable sequence comparison algorithms or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, or at least about 70%, or at least about 80%, or at least about 90%, or at least about 95%, or at least about 98%, or at least about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Polypeptides such as polymerases and/or amino acid sequences are "homologous" when they are derived, naturally or artificially, from a common ancestral protein or protein sequence. Similarly, polynucleotides and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages are readily available. An example of an algorithm that is suitable for determining percent sequence identity and sequence similarity is the BLAST algorithm, and a software-based interface for performing BLAST analyses is publicly available through the National Center for Biotechnology Information.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same.

In the present disclosure, numeric ranges are inclusive of the numbers defining the range. It should be recognized that chemical structures and formula may be elongated or enlarged for illustrative purposes.

Unless defined otherwise, all technical and scientific terms used herein have the same meaning as commonly understood by those working in the fields to which this disclosure pertain.

It is to be understood that the terminology used herein is for the purpose of describing particular embodiments only, and is not intended to be limiting, since the scope of the present teachings will be limited only by the appended claims.

As disclosed herein, a number of ranges of values are provided. It is understood that each intervening value, to the tenth of the unit of the lower limit, unless the context clearly dictates otherwise, between the upper and lower limits of that range is also specifically disclosed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

All patents and publications referred to herein are expressly incorporated by reference.

As used in the specification and appended claims, the terms "a," "an," and "the" include both singular and plural referents, unless the context clearly dictates otherwise. Thus, for example, "a moiety" includes one moiety and plural moieties.

Methods of Use and Applications

The mutant polymerases presented herein can be used for polynucleatide sequencing, such as a sequencing-by-synthesis (SBS) technique. Briefly, SBS can be performed by using a target nucleic acid as a template for synthesis of a complementary stand. A primer binds to the template and is extended with one or more labeled nucleotides by the activity of a DNA polymerase. The primary strand (i.e., the primer hybridized to the template) is extended using the target nucleic acid as template and incorporates a labeled nucleotide that can be detected. Optionally, the labeled nucleotides can be reversible terminators that terminates further primer extension once a nucleotide has been added to a primer. For example, reversible terminator can be added to a primer such that subsequent extension cannot occur until a deblocking agent is delivered to reverse the termination. Thus, for embodiments that use reversible terminators, a deblocking reagent can be delivered to the sequencing instrument (before or after detection of the label occurs).

Some reversible terminators (for example, Lightning Terminators) have photocleavable blocking groups that are designed to terminate DNA synthesis as well as cleave rapidly. Lightning Terminators are combined with and incorporated at the 3' end of a primary strand, such as by a single-base extension of the strand annealed to a template, or alternatively by a single base extension of the primary strand in a template-independent manner with a terminal deoxynucleotide transferase (TdT).

In some embodiments, the present mutant polymerases are used for Template-Independent Enzymatic Oligo Synthesis (TiEOS). In some embodiments, the present methods comprise contacting a priming strand with a mutant polymerase (such as Pfu26 or Pfu48) and one or more 3'-OH unblocked reversible terminators. The present methods can comprise elongating a 3' end of the priming strand by a single-base addition per cycle. In some embodiments, the present mutant polymerases incorporate reversible terminators to a priming strand in a template-independent fashion with high incorporation and termination efficiencies Nucleic Acids Encoding Mutant Polymerases Further presented herein are nucleic acids encoding the mutant polymerase enzymes presented herein. For any given mutant polymerase disclosed or taught by the present disclosure, it is possible to obtain a nucleotide sequence encoding that mutant polymerase according to known principles of molecular biology. Accordingly, the present disclosure provides a description of nucleic acids encoding the mutant polymerases, as well as the mutant polymerases themselves.

Nucleic acids encoding the recombinant polymerases of disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases presented herein.

Given that the wild type nucleotide sequence encoding 9° N polymerase is known, it is possible to deduce a nucleotide sequence encoding any given mutant version of 9° N having one or more amino acid substitutions using the standard genetic code. Similarly, nucleotide sequences can readily be derived for mutant versions of other polymerases such as, for example, Vent, Pfu, T. sp. JDF-3, Taq, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimized by including an enhancer sequence in the vector. Enhancers are cis-acting elements of DNA that act on a promoter to increase the level of transcription. Vectors will also generally include origins of replication in addition to the selectable markers.

In view of the present disclosure, various methods can be implemented in keeping with the present teachings. Further, the various components, materials, structures and parameters are included by way of illustration and example only and not in any limiting sense. In view of the present disclosure, the present teachings can be implemented in other applications and components, materials, structures and equipment to implement these applications can be determined, while remaining within the scope of the appended claims.

EXAMPLES

General Methods and Conditions For Examples

The experimental procedures and conditions used in the Examples are generally described below.

A. Creation & Production of Mutant Polymerases

This section generally describes how the present mutant polymerases were created by generating mutant gene sequences, and the mutant genes were expressed to obtain the various mutant polymerases used in the Examples below. The mutant DNA polymerases were made using the reagents and protocols from Agilent's QuikChange Lightning Multi Site-Directed Mutagenesis Kit. Mutant plasmids were sequence confirmed then transformed into the expression host BL21-Gold (DE3) (Agilent). The cells were grown to exponential phase ($OD_{600}$~0.4) and induced with 1 mM IPTG. Heat-treated bacterial lysates and purified Pfu mutants were prepared as described in Hansen et al (2011) NAR 39: 1801-1810.

B. Sequencing with Mutant Polymerases and Sequencing Metrics

This section generally describes how the present mutant polymerases were used for sequencing-by-synthesis, and how their performance in sequencing was measured. Sequencing was performed on a breadboard instrument, essentially as described in Hertzog D, et al., "A high-performance, low-cost approach to next-generation sequencing", BioOptics World. 2011 Issue November/December 2011.

Example 1

In this example, mutations were introduced into the DNA polymerase of SEQ ID NO: 12 (Therminator) in an attempt to improve its capability in sequencing with 3'-OH unblocked terminators. Such mutations to *Thermococcus* sp. 9° N DNA polymerase are disclosed in U.S. Pat. Nos. 9,273,352; 9,677,059; 9,765,309; US Pat. App. Publication No. 20160032377. The following table summarizes sequencing metrics with Lightning Terminators.

| Expt. # | Therminator mutation# (9°N DNA pol numbering) | ARL (87 cycles) | Lead + Lag | % reads > 85 bp |
|---|---|---|---|---|
| 1-1 | None | 72.3 | 1.6 | 35.4 |
| 1-2 | R743A | 55.0 | 2.4 | 8.6 |
| 1-3 | T514S | 72.0 | 1.1 | 38.3 |
| 1-4 | I521L | 53.9 | 2.8 | 2.8 |
| 1-5 | K477M | 68.8 | 1.6 | 27.7 |
| 1-6 | T144G | 70.5 | 1.4 | 31.8 |
| 1-7 | G153D | 66.7 | 1.8 | 21.5 |
| 1-8 | K476W | 70.2 | 1.4 | 31.8 |
| 1-9 | L478S | 65.8 | 1.6 | 19.6 |
| 1-10 | T590I | 68.1 | 1.3 | 32.2 |
| 1-11 | A639F | 58.5 | 2.3 | 6.9 |
| 1-12 | D718N | 65.6 | 1.8 | 17.9 |

Purified mutants were compared at the same unit concentrations (0.08 U/ul in cycle 1 and 0.008 U/ul in cycles 2-n). The "none" control was produced and screened alongside Therminator mutants.

As used in this example and those that follow, "Lead+ Lag" refers to dephasing errors in Sequencing by Synthesis technology caused by either reading the next base signal (Lead) or reading the previous base signal (Lag) relative to current base signals. Such errors may arise because of imperfect incorporation of reversible terminators by the polymerase. These mutations to the polymerase were found to be ineffective in improving sequencing performance by the Therminator polymerase, in that there was no increase in Average Read Length (ARL) relative to Therminator, for incorporating Lightning Terminators. These results indicate the difficulty and unpredictability in identifying alternative polymerases and/or mutations for base-modified reversible terminators.

Example 2

In this example, mutant polymerases were created by introducing certain mutations (D141A/E143A/A485L) which are present in Therminator. The three mutations were introduced at the equivalent positions in JDF3 (*Thermococcus* sp. JDF3) and Pfu (*Pyrococcus furiosus*) DNA polymerases. The new mutant polymerases were then evaluated for their performance in sequencing with Lightning Terminators, as described above. Table 2 summarizes the results which show the influence of natural variation on sequencing metrics. The resulting ARLs were more than 20 bp lower compared to Therminator, indicating that variation between different polymerases can have a significant impact on sequencing with 3'-OH unblocked reversible terminators.

Figure 2:
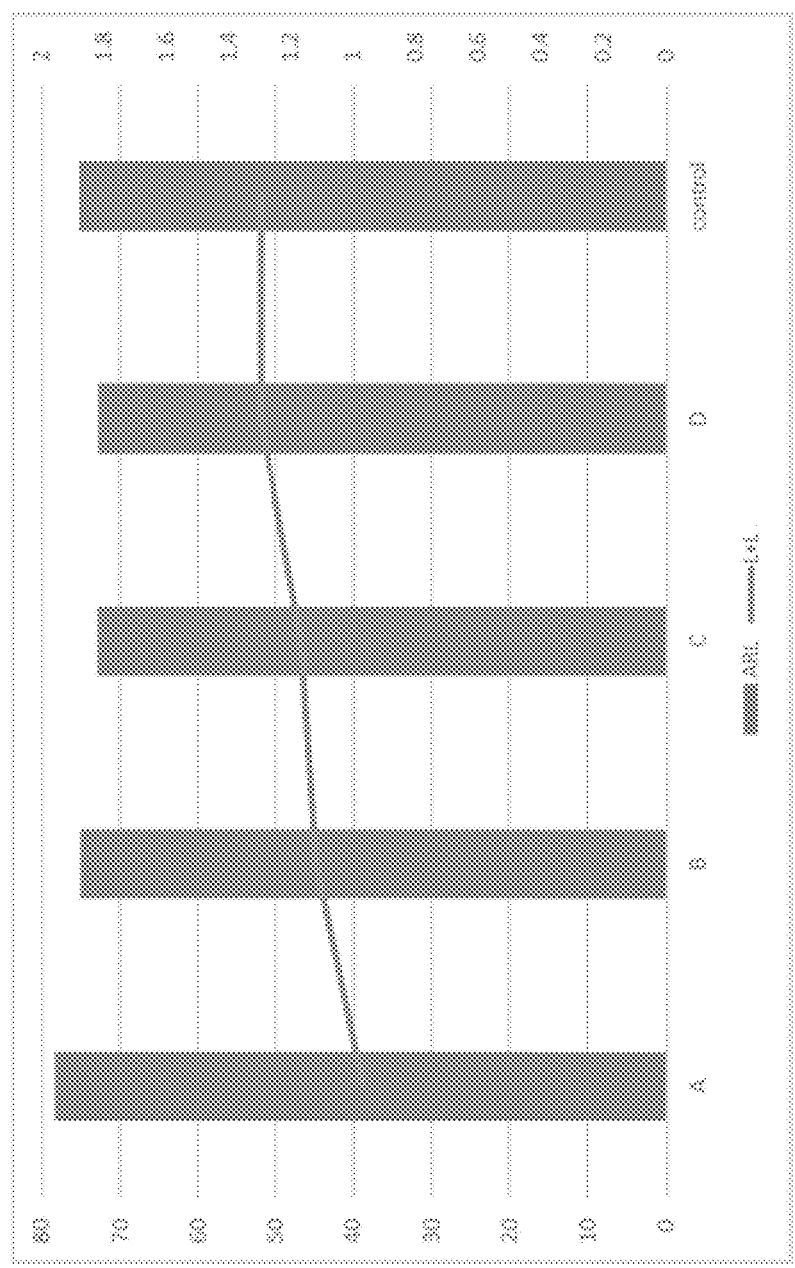
FIG. 2 shows sequencing metrics from sequencing with mutant chimeric polymerases in Example 4. The following domains of Pfu A486L/Y546H DNA polymerase ("control"; Pfu 2) were substituted with the corresponding segments from 9° N DNA polymerase: A-1-99; B-100-199; C-400-

Additionally, a series of chimeric polymerases and single-point mutants were constructed to identify the amino acid differences between 9° N, JDF3, and Pfu DNA polymerases that influence sequencing with 3'-OH unblocked reversible terminators. The following table indicates the mutations made to those polymerases and the sequencing metrics from their use in sequencing with Lightning Terminators. Results from evaluation of the mutant polymerases in sequencing are also illustrated in FIG. 2.

| Expt. # | Polymerase (D141A/E143A) | ARL (87 cycles) | Lead + Lag | % reads > 85 | Equivalent Position in Pfu |
|---|---|---|---|---|---|
| 2-1 | Therminator (9°N polB A485L) | 76.0 | 1.3 | 49.6 | A486L |
| 2-2 | JDF3 polB A485L | 47.4 | 2.2 | 0.7 | A486L |
| 2-3 | JDF3 polB A485L/Y493F | 64.5 | 1.8 | 15.1 | A486L/Y494F |
| 2-4 | Pfu polB A486L | 54.9 | 2.1 | 9.9 | — |
| 2-5 | Pfu polB A486L/Y546H | 75.3 | 1.3 | 49.7 | — |

Alternative polymerases were compared at the same protein concentrations (0.02 ug/uL in cycle 1 and 0.002 ug/uL in cycles 2-n)

Natural variation among those three polymerases at 494 and 546 (Pfu numbering) was found to have a significant impact on sequencing metrics. ARLs improved by 17 bp when phenylalanine (F; naturally occurring in 9° N and Pfu) was introduced in JDF3 at the position equivalent to 494 in Pfu (JDF3 A485L/Y493F; Experiment #2-3). An even greater improvement was noted when histidine (H; naturally occurring in 9° N and JDF3) was introduced at codon 546 in Pfu (Expt. #2-5). In fact, sequencing metrics with Pfu A486L/Y546H (Experiment #2-5) were nearly identical to Therminator, except that Pfu A486L/Y546H exhibited lower leading and higher lagging values compared to Therminator (shown in the table below).

Example 3

In this example, mutant DNA polymerases were derived from Pfu polymerase by making various mutations identified for archaeal polymerases. Mutations were selected from those described in research and patent literature (shown below). The mutations were introduced into a Pfu polymerase which also had the mutations A486L and Y546H. The mutations are shown in the following Table, along with literature in which such mutations are discussed for various polymerases.

| Mutations Tested | Literature Citation |
|---|---|
| E399D, N400D, R407I, L479S, K477W, T591I | Ramsay, N. et al (2010) CyDNA: *Synthesis and Replication of Highly Cy-Dye Substituted DNA by an Evolved Polymerase.* J. AM. CHEM. SOC. 2010, 132, 5096-5104. Bomati, E. et al. *Modified Polymerases for Improved Incorporation of Nucleotide Analogues.* US 9,677,057 |
| T515S | Chen, C-Y et al. *Modified Polymerases for Improved Incorporation of Nucleotide Analogues.* US 20160032377 |
| Y410G | Cozens et al (2012) A short adaptive path from DNA to RNA polymerases. Proc. Natl. Acad. Sci. 109:8067-72. |
| L409Y, P411L | Arezi et al (2002) *Efficient and High Fidelity Incorporation of Dye-terminators by a Novel Archaeal DNA Polymerase Mutant.* J. Mol. Biol. (2002) 322, 719-729; also US 20030228616. |

The mutant polymerases were used for sequencing as described above. Of these mutations added to the Pfu polymerases, only K477W had a significant impact on sequence metrics, most notably in a higher percentage of full-length reads (Expt. #2-6). This mutant (Pfu D141A/E143A/K477W/A486L/Y546H) was given the arbitrary name Pfu10. The amino acid sequence of Pfu10 is set forth in SEQ ID NO:2. This example shows that Pfu10 is an improved sequencing enzyme for use in sequencing-by-synthesis using 3'-OH unblocked reversible terminators.

| Expt. # | Polymerase | # runs | ARL (87 cycles) | FracQ30 | Leading | Lagging | % reads > 85 bp |
|---|---|---|---|---|---|---|---|
| 2-1 | Therminator (NEB) | 110 | 76.0 | 0.58 | 0.70 | 0.61 | 49.6 |
| 2-6 | Pfu10 | 12 | 80.4 | 0.62 | 0.24 | 0.66 | 69.5 |

As used in this and other examples, "FracQ30" refers to percentage of sequencing base reads having a Q score of 30 (Q30) in total sequencing reads. The discovery that K477W improves Pfu was unexpected since the equivalent mutation in Therminator failed to improve sequencing with Lightning Terminators (see Expt. #1-8; K476W), even though Therminator contains L, F, and H, at positions equivalent to positions 486, 494, and 546, respectively, in Pfu10. These results suggest that, with 3'-OH unblocked reversible terminators, the benefits of K477W may be realized with sequencing polymerases that are more closely related to Pfu than to Therminator. A BLASTP alignment indicates that the percent amino acid sequence identity between Pfu10 and 9°N DNA polymerase (parent of Therminator) is 79.9%.

Example 4

In this example, a variety of mutations were introduced into Pfu10 by multi-site mutagenesis or into Pfu A486L/Y546H by domain substitutions to explore an acceptable degree of reduced identity and identify other mutant Pfu polymerases containing L486, F494, H546, and W477. SEQ ID NO:3 shows the amino acid sequence of a Pfu10 variant (called "PFU10-N12") with 15 conservative mutations appearing in archaeal DNA polymerases, plus a M129A substitution that eliminates a potential translational start site (97.9% identity to Pfu10). Pfu10 and Pfu10-N12 were evaluated for performance in sequencing with Lightning Terminators, as described above.

The following table summarizes results showing the sequencing performance of the Pfu10 variant. This variant (Pfu10-N12) performs comparably if not slightly better than Pfu10 in sequencing with Lightning Terminators.

| Expt. # | Enzyme | DNA library sequenced | # enzyme lots/# sequencing runs | ARL (120 cycles) | FracQ30 | Lead + Lag | % reads > 85 |
|---|---|---|---|---|---|---|---|
| 3-1 | Pfu10 | Human | 4/44 | 109.7 | 0.65 | 1.1 | 92.0 |
| 3-2 | Pfu10-N12 | Human | 2/6 | 111.6 | 0.68 | 1.0 | 93.3 |
| 3-3 | Pfu10 | E. coli | 4/27 | 92.3 | 0.63 | 0.8 | 79.9 |
| 3-4 | Pfu10-N12 | E. coli | 2/8 | 93.8 | 0.65 | 0.9 | 82.6 |

In addition, arbitrary domain substitutions can be used to increase diversity while retaining the desired level of activity. The effect of domain substitutions on sequencing metrics is illustrated by FIG. 2. For example, replacing amino acid segments 1-99, 100-199, 400-449, and 500-599 in Pfu L486L/Y546H with the corresponding polypeptide sequence in Therminator had minimal impact on sequencing metrics, demonstrating that Pfu10 can accommodate at least 16-29 additional mutations (96.3-97.9% variation) without compromising its ability to incorporate 3'-OH unblocked reversible terminators.

Example 5

This example used saturation mutagenesis at positions 486 and 494 in Pfu D141A/E143A to create additional mutant polymerases. Bacterial extracts were screened in a plate-based single-base extension assay employing Lightning Terminator-A (LTA). Positive clones producing the highest fluorescent signals were sequenced to identify the amino acid replacement. As shown in FIGS. 3 and 4, A486 and F494 are highly mutable and multiple substitutions improve incorporation of Lightning Terminators, including A486F, A486Y, A486N, A486R, A486H, F494C, F494I, F494N, and F494T. Selected lysates, based on screening results, were submitted for sequencing, and an amino acid identification was made based on the selections.

FIG. 3 illustrates the saturation of position 486 in a Pfu polymerase. The QuikChange kit was used with degenerate NDT codon primers to create a library of Pfu A486 mutants. A NDT codon comprises an A, C, G, or T at the first position, an A, G, or T at the second position, and a T at the third position, thereby introducing variability into the primer. The 12 possible NDT codons represent 12 amino acids (Phe, Leu, Ile, Val, Tyr, His, Asn, Asp, Cys, Arg, Ser, and Gly). Heat-clarified extracts were prepared from 32 randomly selected colonies. Extracts were screened for incorporation of LTA in a microtiter plate assay employing an immobilized dsDNA substrate. Fluorescent signal for the "A" mutant corresponds to background for wild-type Pfu (wild-type alanine at codon 486).

FIGS. 4A and 4B illustrate the saturation of position 494 in a Pfu polymerase. The QuikChange kit was used with 2 pools of degenerate codon primers (A, B) to create a library of Pfu F494 mutants. Heat-clarified extracts were prepared from 32 randomly selected colonies. Extracts were screened for incorporation of LTA in a microtiter plate assay employing an immobilized DNA substrate. Fluorescent signals for the "F" mutants correspond to background for wild-type Pfu (wild-type phenylalanine at position 494).

Example 6

In this example, additional mutant polymerases were derived from Pfu polymerase. To generate the mutants, eighty-seven codons in the Pfu pol B gene were saturated using the QuikChange Lightning Mutagenesis kit and oligonucleotides containing "NDT" codons to create R, N, D, C, G, H, I, L, F, S, Y, and V substitutions with equal frequency. In some cases, mutants missing from NDT libraries were prepared in a separate QuikChange reaction with an equimolar mixture of mutagenic oligos encoding the remaining mutations (A, T, K, Q, E, P, K, W). Thirty-two clones were randomly selected from each QuikChange library (with the exception of T267, Y403, Y410, 1475, G499 and K675 libraries which generated fewer transformants). Bacterial lysates were prepared and screened for incorporation of LTA and LTC using a plate-based assay with immobilized primer-templates. A limited number of mutants were also screened for utilization of LTG and LTU (similar trends; data not shown). After washing and UV cleavage (to minimize dye quenching effects), plates were read and fluorescent signals compared to Pfu controls. The following table identifies four mutant Pfu polymerases that served as controls, which were given the arbitrary names Pfu5, Pfu1, and Pfu2, along with Pfu10 (which is discussed above).

|  | D141A/E143A | A486L | Y546H | K477W |
|---|---|---|---|---|
| Pfu5 | + | − | − | − |
| Pfu1 | + | + | − | − |
| Pfu2 | + | + | + | − |
| Pfu10 | + | + | + | + |

Selected lysates, based on screening results, were submitted for sequencing, and an amino acid identification was made based on the selections. Control extracts show similar activity (U/ul) with natural nucleotides (FIG. 5), but only A486L-containing mutant polymerases (Pfu1, Pfu2, Pfu10) could utilize Lightning Terminators (FIG. 6). Y546H on its own does not allow Lightning Terminator incorporation (FIGS. 7A-7B). However, the combination of A486L and Y546H (in Pfu2 and Pfu10) was found to maximize incorporation of LTC (FIG. 6), which suggests a disfavorable interaction between LTC and Y546, that can be overcome by substituting tyrosine for histidine. As shown in Example 3, K477W benefits sequencing by increasing the fraction of full-length reads. The mechanism, however, appears unrelated to incorporation efficiency, as K477W (in Pfu10) has a negative impact on LTA and LTU incorporation, or alternatively, on final fluorescence due to tryptophan (W) quenching of the attached fluorophores.

The following codons were subject to saturation: 266, 267, 268, 269, 270, 329, 330, 332, 333, 336, 399, 400, 403, 404, 407, 408, 409, 410, 411, 450, 451, 452, 453, 455, 456, 457, 458, 459, 460, 461, 462, 463, 464, 465, 466, 475, 476, 477, 478, 479, 480, 481, 482, 483, 485, 486, 487, 488, 489, 490, 491, 492, 493, 494, 495, 496, 497, 498, 499, 500, 515, 522, 545, 546, 577, 579, 580, 581, 582, 584, 591, 595, 603, 606, 607, 608, 612, 613, 614, 664, 665, 666, 668, 669, 674, 675, 676. Sixteen of the 87 positions screened could be mutated to effect a significant (>4X wild-type Pfu) improvement in incorporating LTA and/or LTC. The following table shows mutations conferring improved incorporation of LTA and LTC. Four positions appear to be highly substitutable (L409, A486, F494, Y497), and certain amino acid replacements (L409H, L409F, A486Y, A486R, A486H, A486N, F494C, F494N, F494I, F494T) produce superior incorporation signals compared to the Pfu A486L control (Pfu10).

| Codon | LTA | | LTC | |
|---|---|---|---|---|
| Relative increase: | >4X Pfu5 (wild type) | >Pfu10 (A486L) | >4X Pfu5 (wild type) | >Pfu10 (A486L) |
| L270 | X* | | | |
| E330 | GV | | G | |
| Q332 | L | | | |
| L333 | HC | | H | |
| L409 | DCVNHF | HF | DCVNHF | F |
| P451 | LYIW | | | |
| L453 | F | | | |
| L457 | FVP | | FVP | |
| E476 | R | | R | |
| A486 | YRFIHN | YRHN | YRFIHN | R |
| L489 | RQ | | RA | |
| L490 | NFY | | NFY | |
| N492 | — | — | IVP | |
| F494 | QCNIVLEMAT | CNIT | T | |
| Y497 | HCIFMEQ | | HCIE | |
| E581 | R | | | |

*not sequenced

It was observed that mutations at N492 (N492I/V/P) were shown to benefit LTC incorporation exclusively. In addition, certain substitutions at L409 (L409D/C/V/H/F), A486 (A486Y/R/F/I/H/N), and Y497 (Y497H/I) appear to have a greater impact on LTC uptake than LTA. These results suggest that substitutions at Y546 and N492 (which forms H-bonds with the triphosphate portion of the nucleotide) alter the orientation of LTC in the binding pocket to better accommodate its unique base, linker, and/or dye moiety. FIG. 8 shows the location of beneficial mutations in the 9° N DNA polymerase (5OMV) structure, visualized using the iCn3D web-based structure viewer. Mutations that benefit LTC exclusively are located at N492 and Y546. Mutations that provide relatively higher incorporation of LTC over LTA are located at L409, A486, and Y497.

Example 7

This example evaluates the performance of embodiments of the present mutant Pfu polymerases in template-independent enzymatic oligonucleotides synthesis. In this example, the polymerases TdT and Pfu26 (Pfu10+L409Y) (SEQ ID NO:4) and Pfu48 (Pfu26 but with A486R instead of A486L) (SEQ ID NO:5) were compared in template-independent DNA synthesis assays. The assays were carried out with dATP (FIG. 1D), LTA-1 (FIG. 1E), or LTA-2 (FIG. 1F). LTA-1 and LTA-2 did not include any dye or other reporter linked to the molecule.

The template-independent DNA synthesis reactions employed 7.5U TdT (Promega) or 180 nM (3X over primer) Pfu26 (D141A/E143A/A486L/Y546H/K477W/L409Y) or Pfu48 (D141A/E143A/A486R/Y546H/K477W/L409Y). Varying concentrations of dATP were added to 204 (TdT) or 60 nM (Pfu) T7 FOR primer (6'Fam TAATACGACTCAC-TATAGGG) (SEQ ID NO:6) in duplicate reactions containing 1×TdT buffer with $CoCl_2$ (Promega) or 1X ThermoPol buffer (NEB). Reactions were incubated for 30 min. at 37° C. (TdT) or 60° C. (Pfu), and then inactivated with heat (TdT; 10 min. at 70° C.) or EDTA (1 ul 500 uM EDTA). Reaction products were exposed to UV using a Stratalinker (15-watt bulbs, 365 nM, 10 min). Reactions were diluted in water (TdT, 1:333; Pfu, 1:10) and 1 μl (TdT) or 0.5 μl (Pfu) aliquots were brought up to 10 μl with HiDI/LIZ 120 Size Standard. Products were heated at 95° C. for 5 min., cooled on ice for 2 min., and then analyzed on an ABI 3500 capillary electrophoresis system (50 cM capillary, filter set #5, assay=GE5 LIZ120).

Terminal transferase activity was measured by the number of template-independent dATP additions. Results are shown for TdT in FIG. 9A, for Pfu26 in FIG. 9B and for Pfu48 in FIG. 9C. It was found that terminal transferase activity increases or decreases respectively as a function of dATP or primer concentration. These results demonstrate that the L409Y mutation confers terminal transferase activity, as Pfu mutants lacking L409Y (e.g., Pfu10) fail to perform nontemplated dA-addition (See FIG. 10C below).

Example 8

Figure 10A:
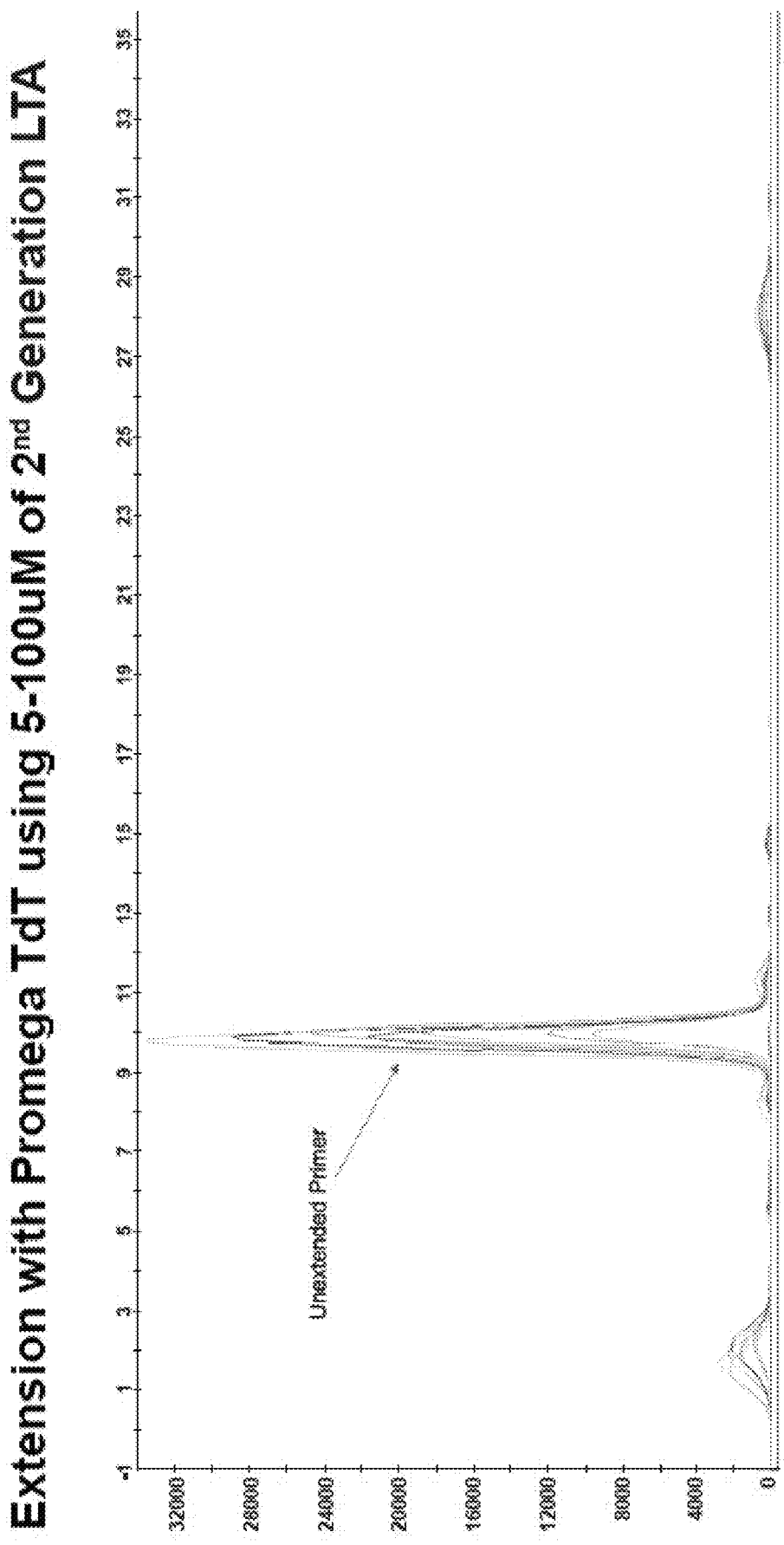

In this example, primer extension was carried out with LTA-2 (FIG. 1F) as a Rp+Sp racemic mixture of α-thiotriphosphate, using the conditions described in Example 7. FIG. 10A shows results at four different concentrations of LTA-2 (5 μM, 10 μM, 5004, and 10004). Comparing FIGS. 9A to 10A shows that TdT did not incorporate the LTA-2 terminator as efficiently as dATP, even at the highest 100 μM concentration.

In further experiments, single-base extension reactions (10 ul) were performed with an equimolar mixture (3 uM each) of two single-stranded oligonucleotides:
CE2: 6Fam-TAATACGACTCACTATAGGGCAG-GAAACAGCTATGACCAGGGGATCAGC (SEQ ID NO:7) and
T7: 6Fam-TAATACGACTCACTATAGGG (SEQ ID NO:8)
Both were labeled with Fam but distinguishable by their lengths using capillary electrophoresis. Primer extension reactions were performed using the following three Pfu mutants at a concentration of 18 nM polymerase:
Pfu10: Pfu polymerase with D141A/E143A/A486L/Y546H/K477W mutations (SEQ ID NO:2)
Pfu26: Pfu polymerase with D141A/E143A/A486L/Y546H/K477W/L409Y mutations (SEQ ID NO:4)
Pfu48: Pfu polymerase with D141A/E143A/A486R/Y546H/K477W/L409Y mutations (SEQ ID NO:5)
The extension reactions also employed individual αS-modified LTs in Rp+Sp racemic mixture (namely, LTA-2, LTU-2, LTG-2, and LTC-2) at final concentrations of 5 uM. LTU-2, LTG-2, and LTC-2 are all C7 or C5-hydroxymethyl-α-tert-butyl-2-nitrobenzyl modified reversible terminators like LTA-2, with uracil, guanine, and cytosine in place of adenine. In these experiments, the reversible terminators did not include a dye. Reactions were incubated, stopped, UV-treated, and analyzed as described in Example 7.

Figure 10B:
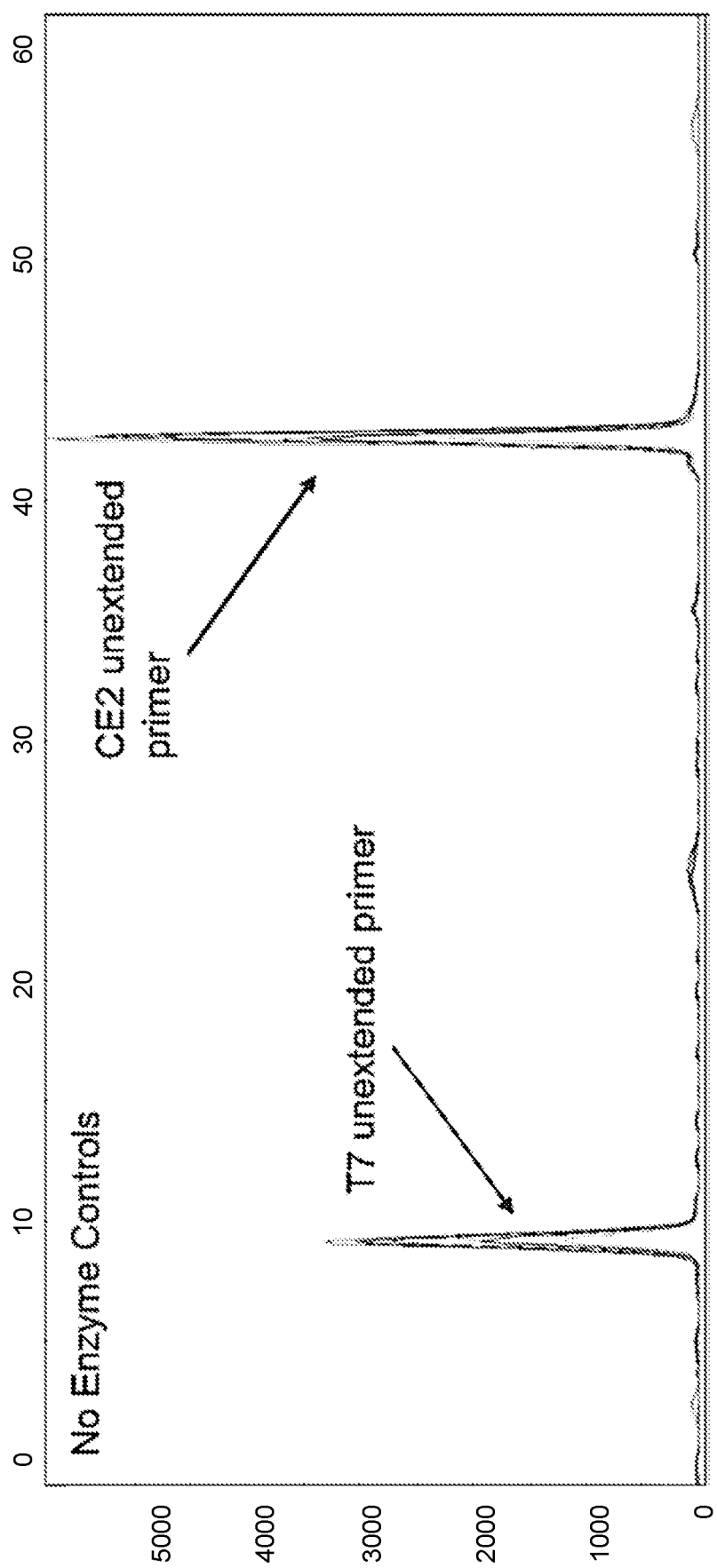
Figure 10C:
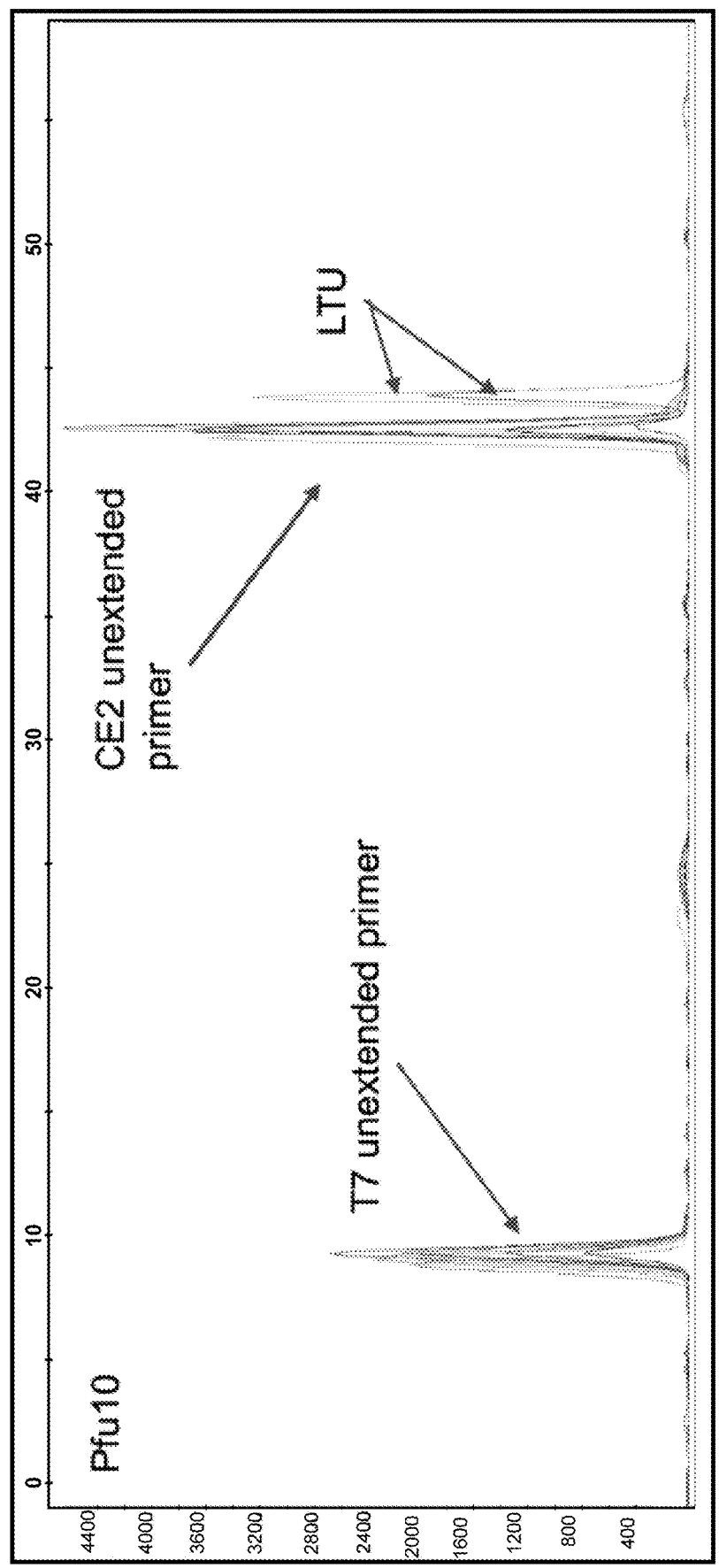
Figure 10D:
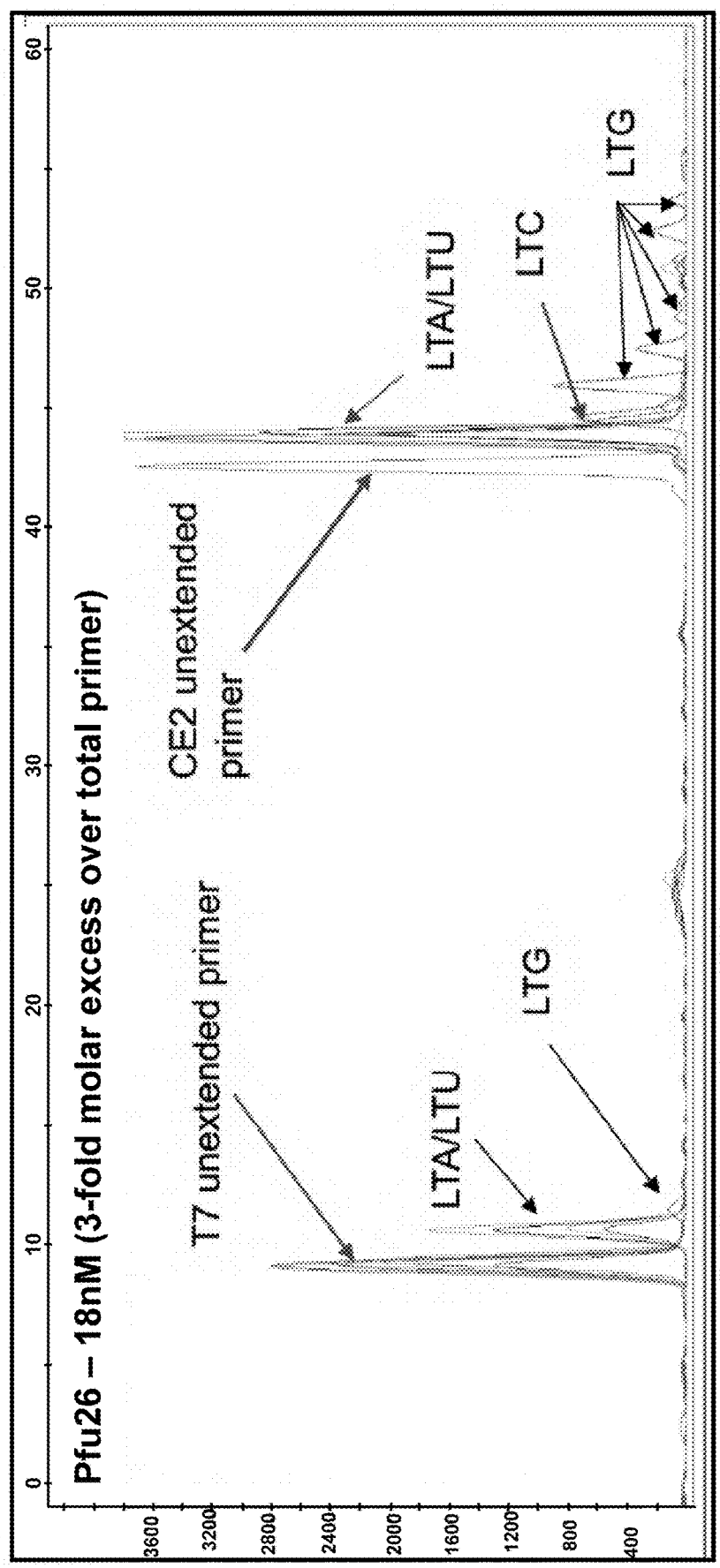
Figure 10E:
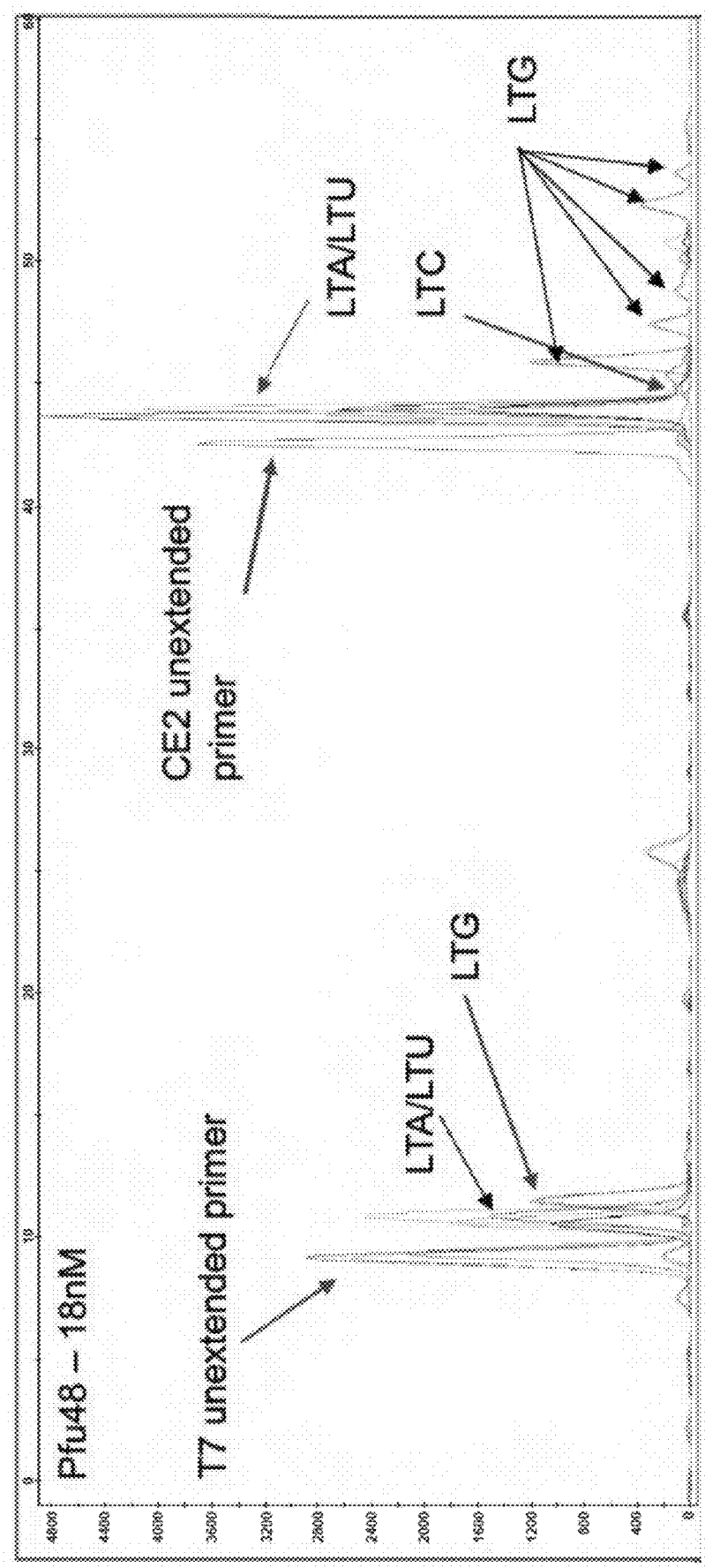

FIG. 10B shows the results of the control extension reactions set up that did not include any polymerase. FIG. 10C shows results of extension reactions when the Pfu10 polymerase was used, and FIGS. 10D and 10E show results using the Pfu26 polymerase and the Pfu48 polymerase, respectively. Comparing FIG. 10A to FIG. 10C to 10E shows that L409Y-containing Pfu mutants (Pfu26, Pfu48) are superior to Calf thymus Terminal Transferase (TdT) in incorporating 3'-OH unblocked reversible terminators LTA-2, LTU-2, LTG-2, and LTC-2. In addition, preliminary data shows that primer extension efficiency is influenced by the primer sequence (CE2>T7) and base (LTA, LTU>LTG>LTC).

Pfu26 can also be used to directly end-label certain oligonucleotides (e.g., for in situ hybridization applications such as disclosed in US Pat. App. Publication No. 20200216841), which avoids the use (and subsequent removal) of complementary templates with 5' overhangs.

Example 9

This example tested the addition of a 3'-OH unblocked reversible terminator (LTA-1, shown in FIG. 1E, or LTA-2, shown in FIG. 1F) to the 3' end of a single-stranded priming strand. The extension reaction was performed with 2 uM or 80 nM of a priming strand and varying concentrations (100/50/10/5/1 μM) of the reversible terminator. The performance of the Pfu26 polymerase was compared to TdT polymerase.

Primer extensions were carried out in duplicate 25 ul reactions containing 7.5 U calf thymus TdT, 1× Promega TdT buffer (with CoCl$_2$), varying concentrations of LTA-1 (100 uM, 50 uM, 10 uM, 5 uM, or 1 uM), and either 2 uM (FIG. 11A to 11C) or 80 nM (FIG. 11D to 11F) of a priming strand (Fam-labeled T7 F primer (6Fam TAATACGACT-CACTATAGGG), SEQ ID NO:8). Controls were performed without the addition of a polymerase. Primer extensions were also carried out in reactions containing the Pfu26 mutant polymerase, 60 nM of the priming strand, and various concentrations (10 μM or 5 μM or 1 μM) of LTA-1 or LTA-2.

Reactions were incubated at 37° C. for 30 min., and then heat-killed for 10 min. at 70° C. Reaction products were split in half, and one-half was treated with UV as described in Example 7. Reactions were then diluted 1:333 (2 uM primer) or 1:13 (80 nM primer) in water, and 0.5 ul portions were analyzed by capillary electrophoresis using the conditions provided in Example 7.

Results from the reactions using the TdT polymerase are shown in FIGS. 11A to 11F. Results from the reactions using the Pfu26 polymerase are shown in FIGS. 12A and 12B.

Figure 11A:
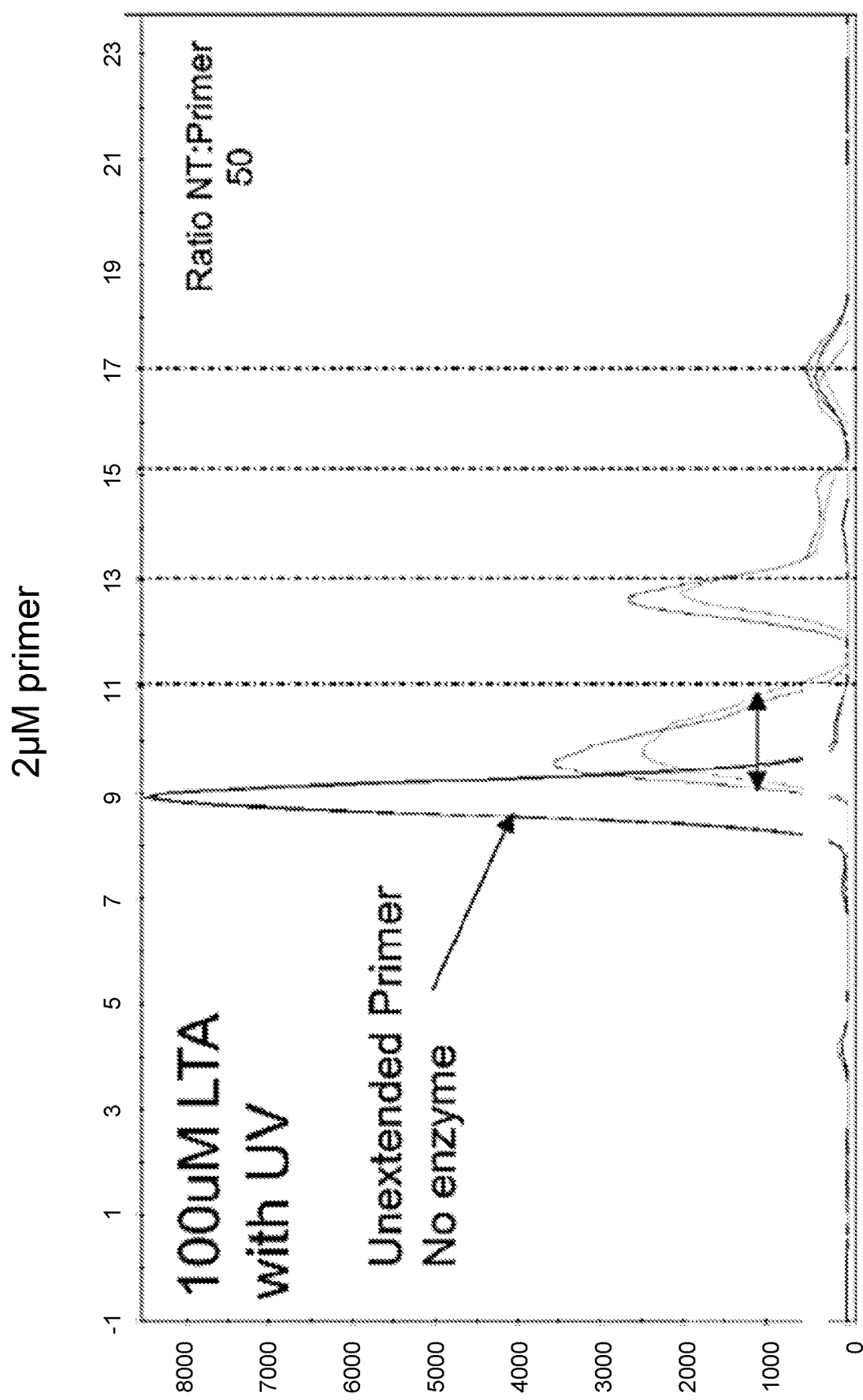
Figure 11A:
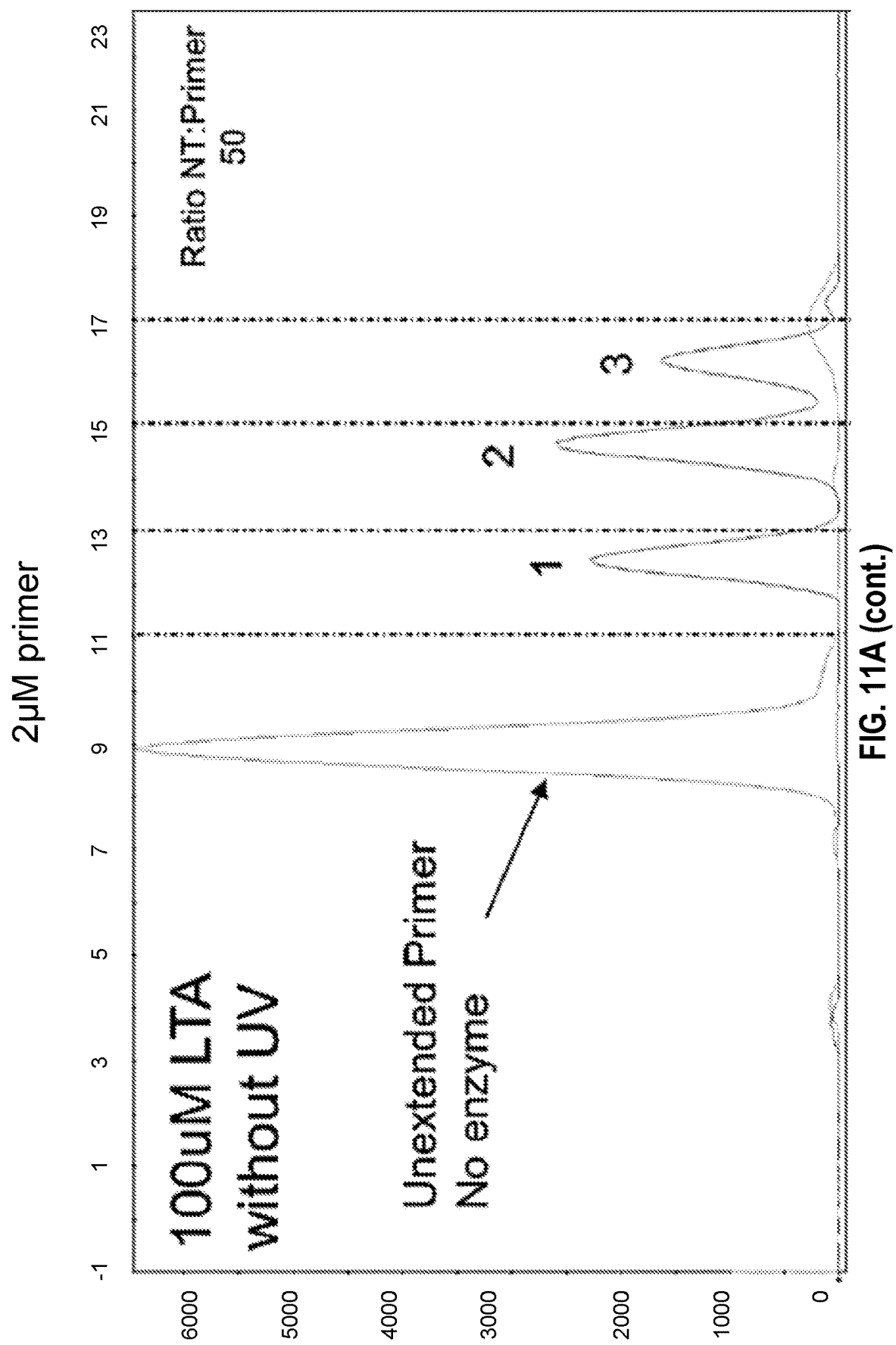
Figure 11A:
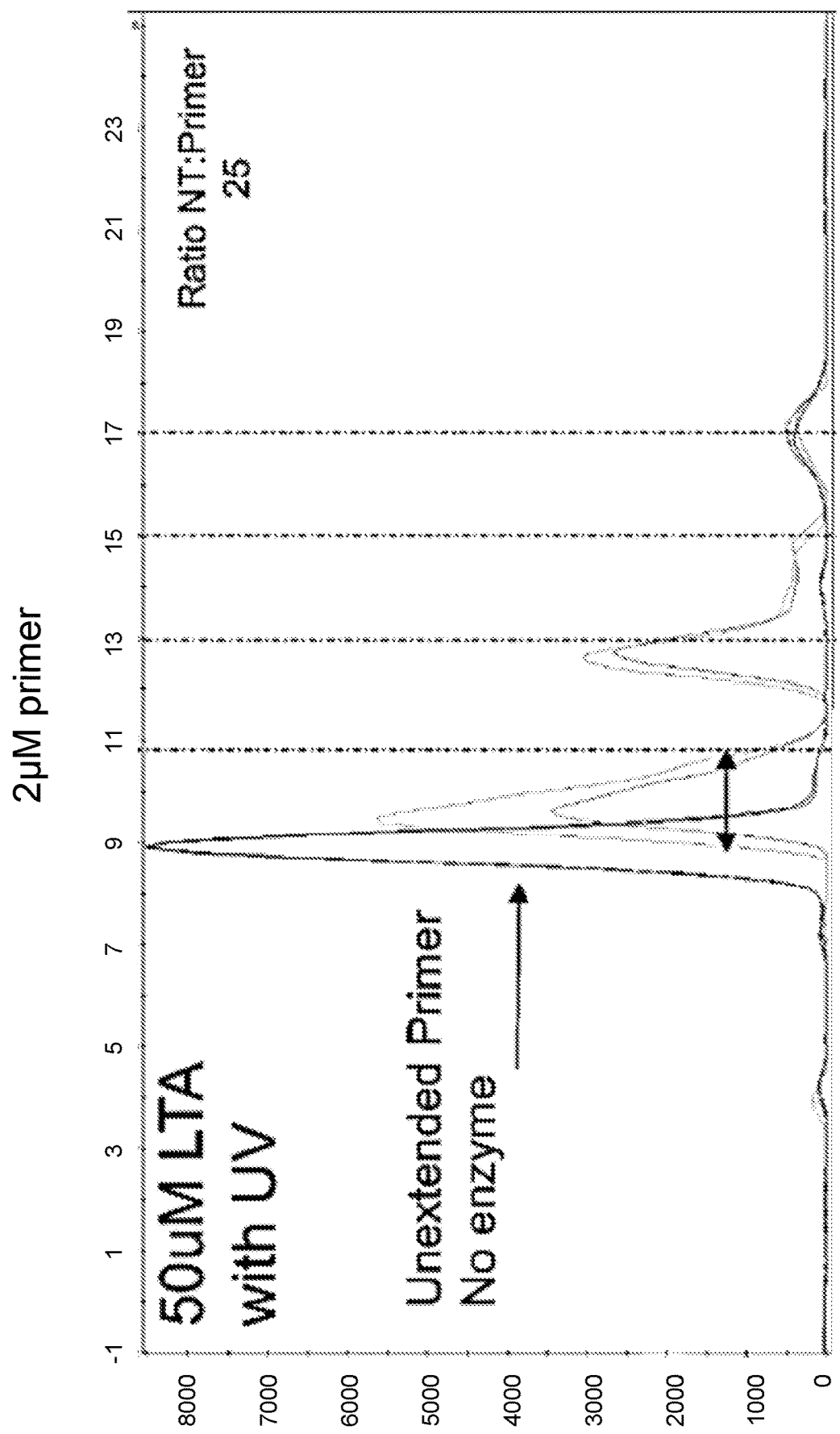
Figure 11A:
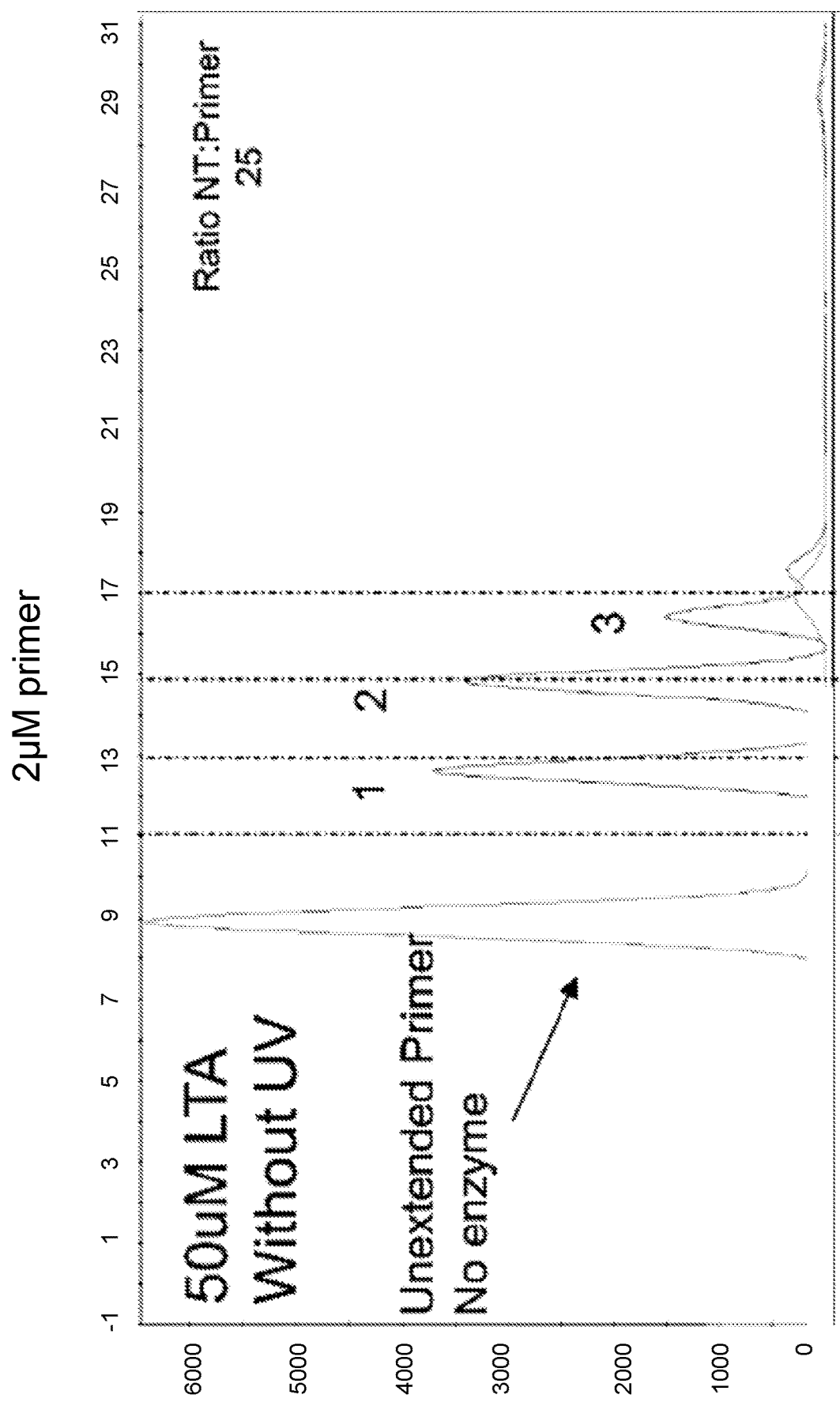
Figure 11B:
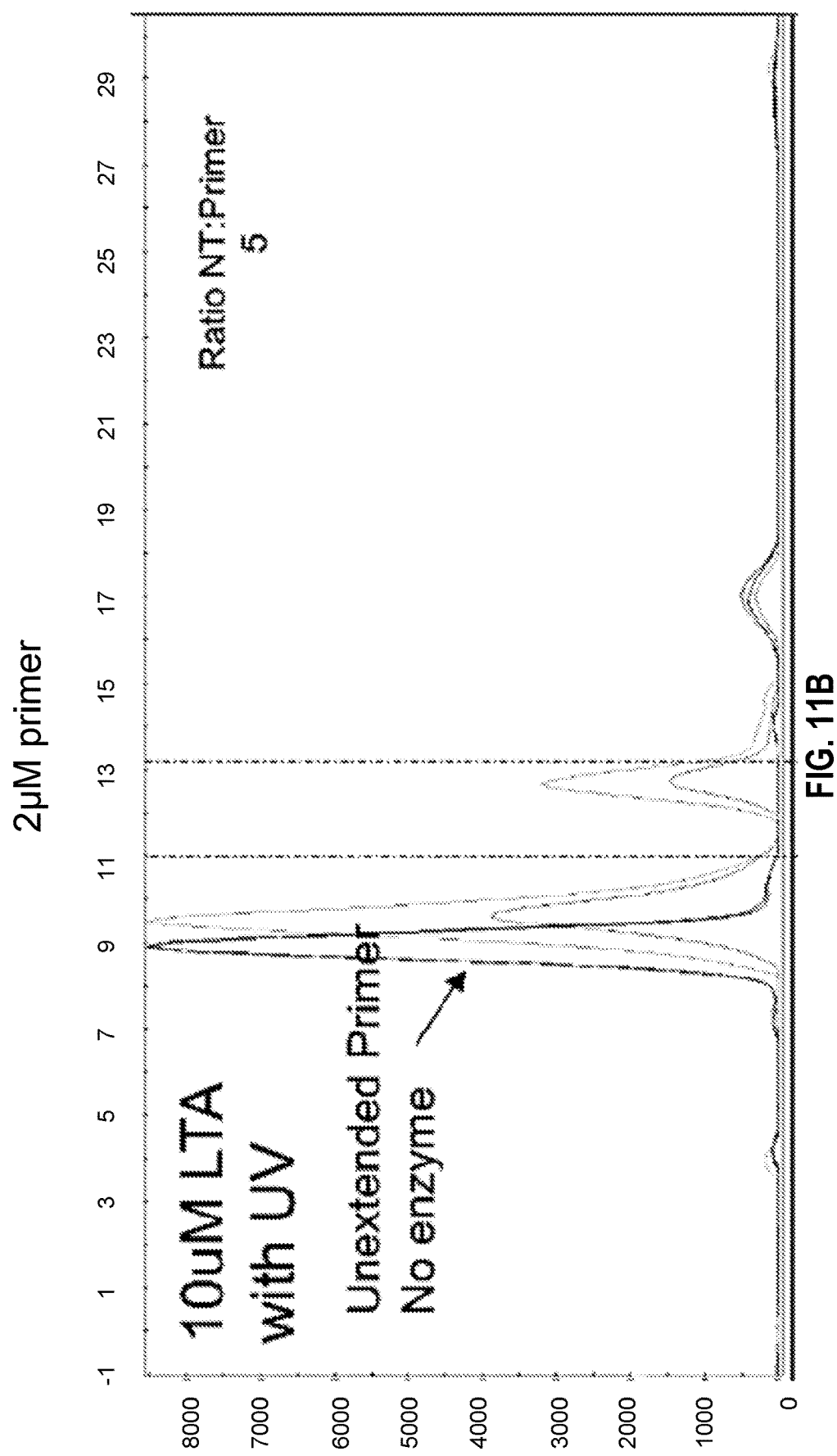
Figure 11B:
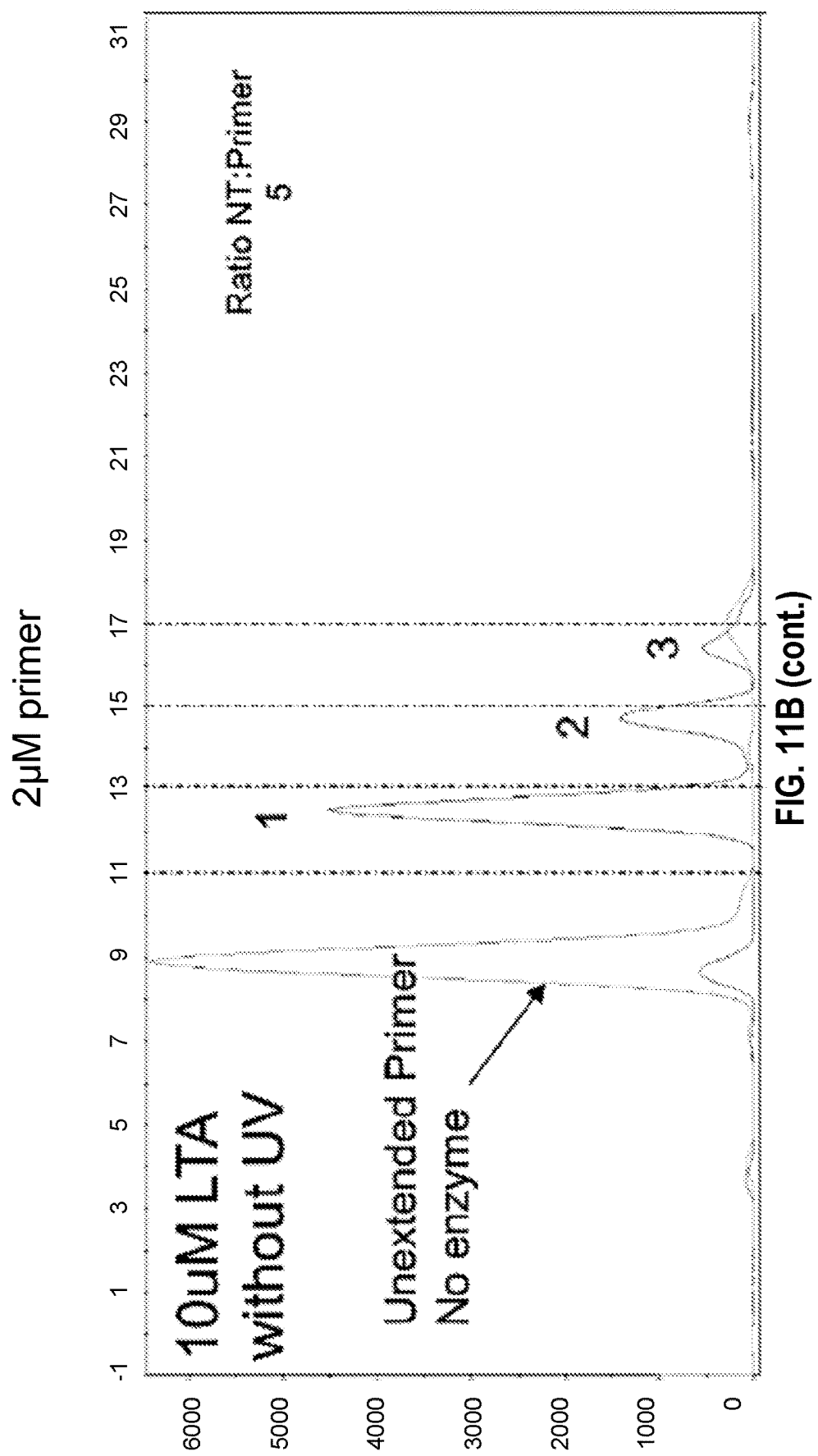
Figure 11B:
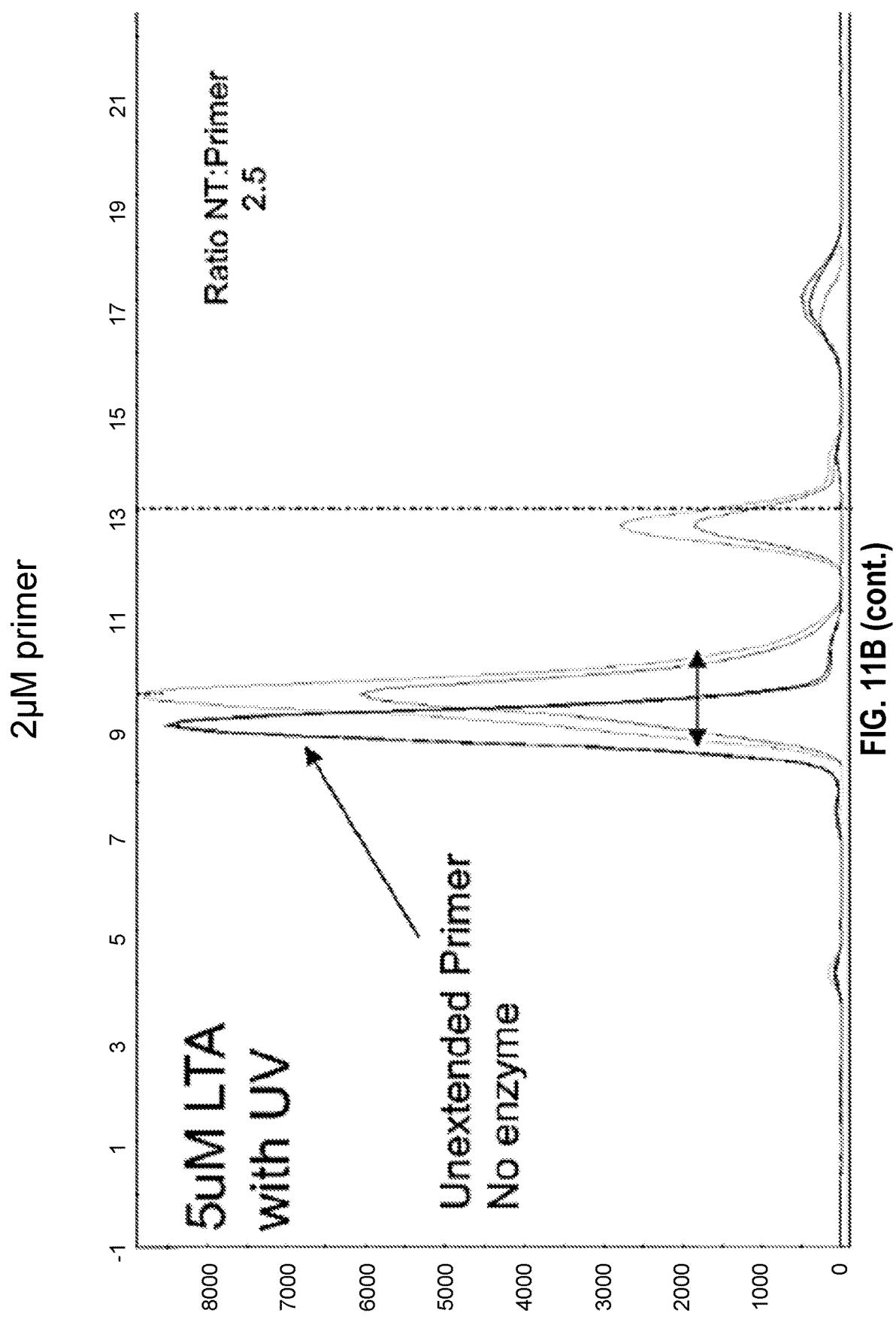
Figure 11B:
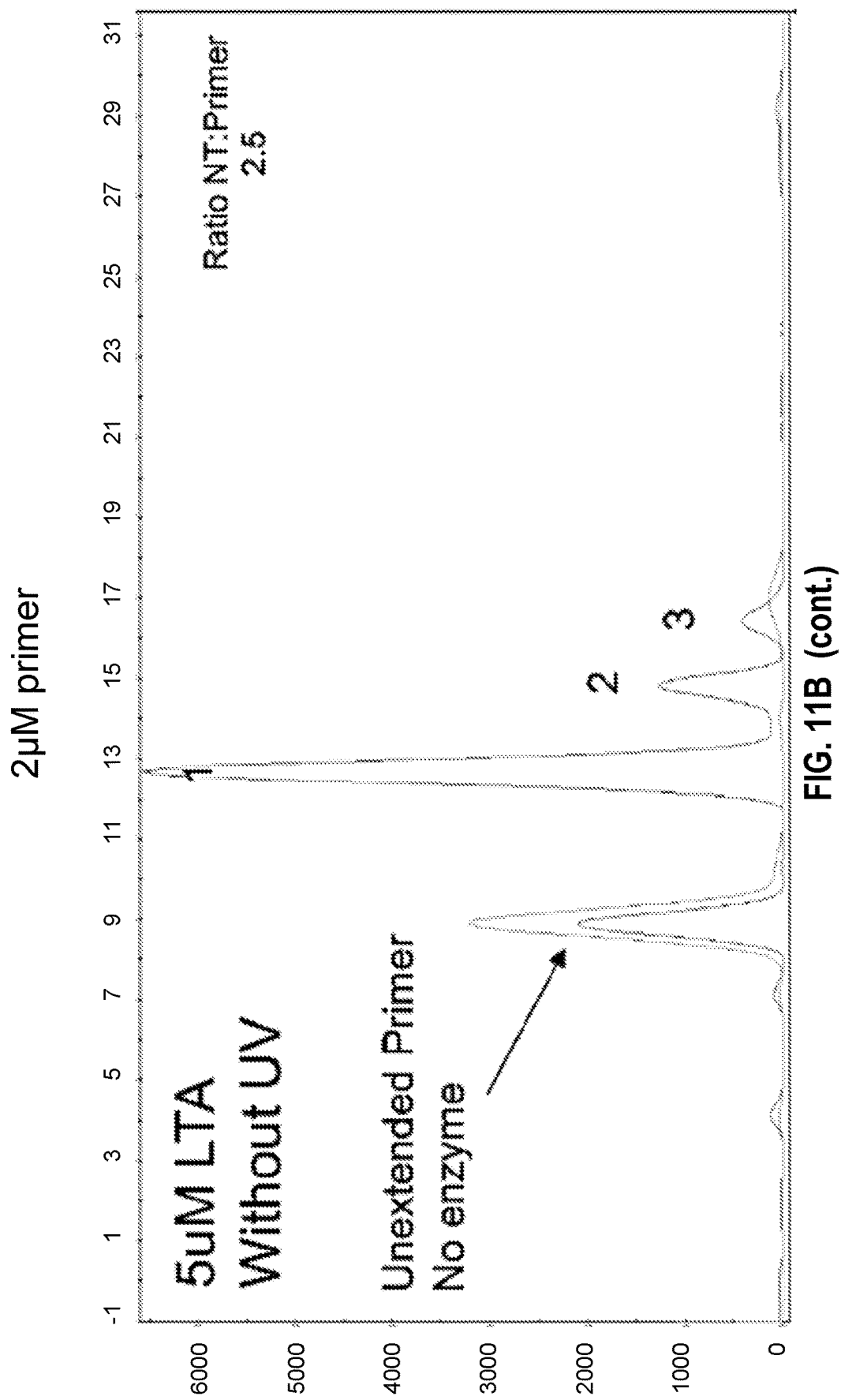
Figure 11C:
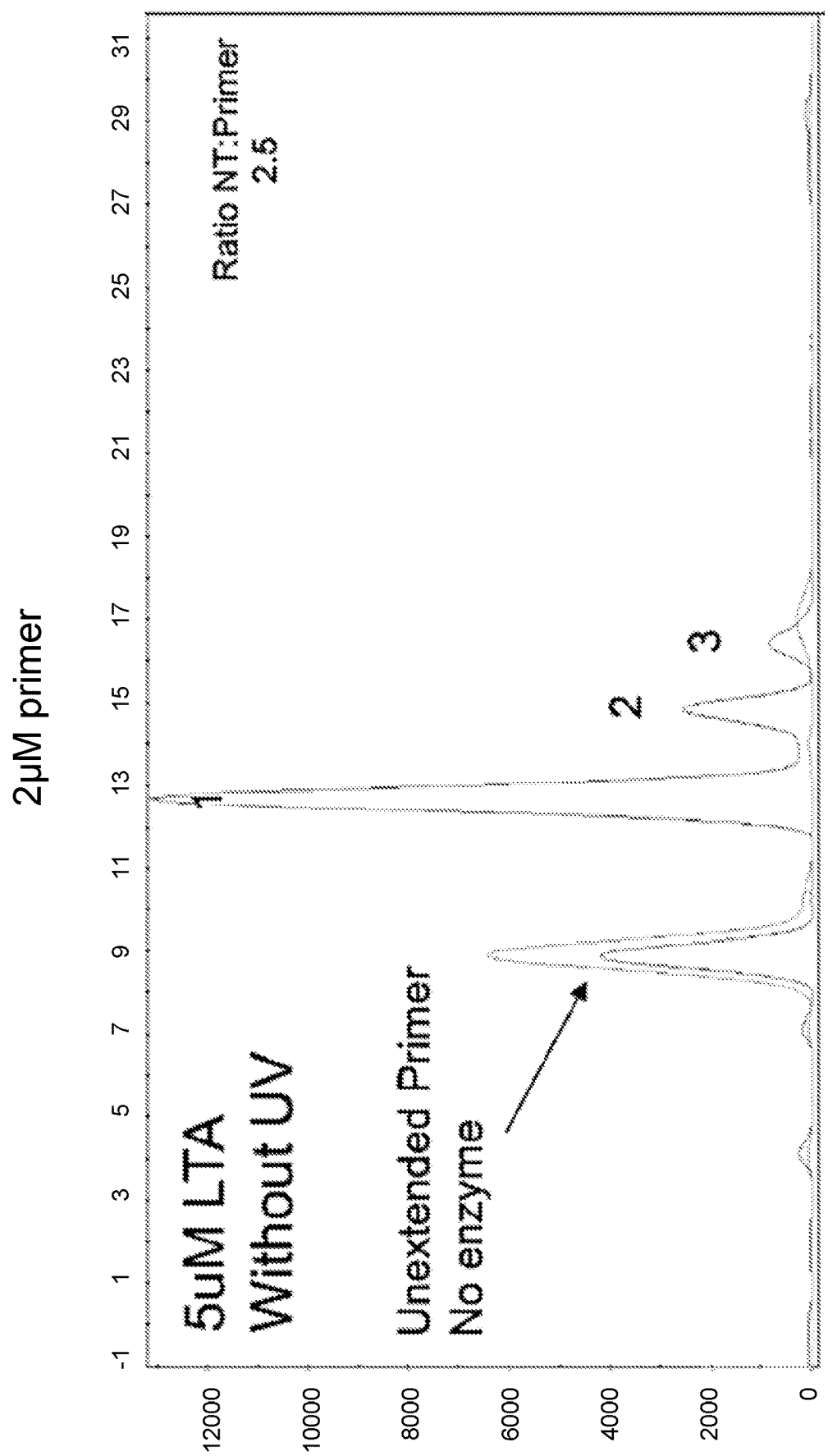
Figure 11C:
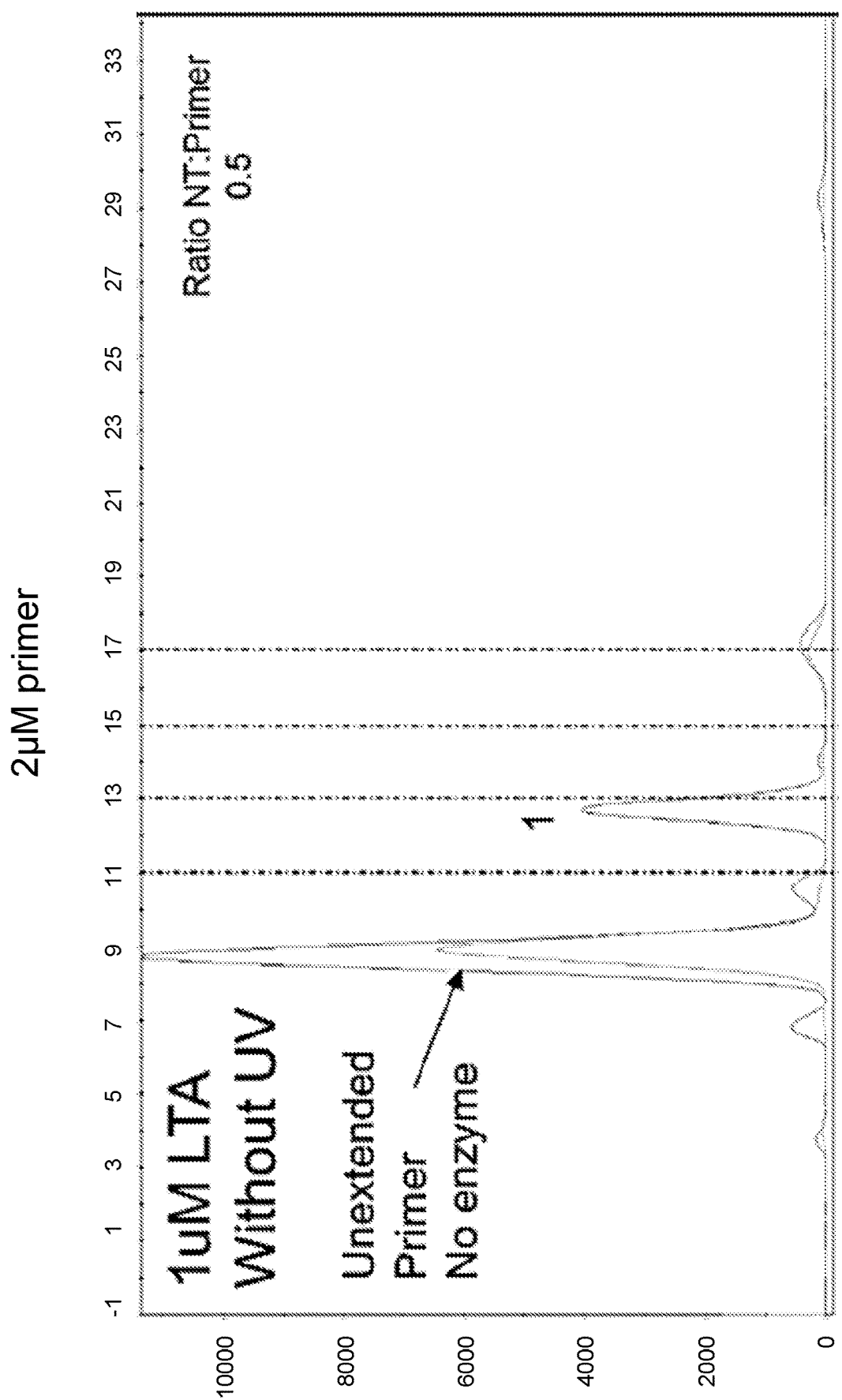

The potential of using "scarless" LTs for TiEOS was demonstrated using LTA-1, a prototype reversible terminator that lacks the α-thio-triphosphate and α-tert-butyl modifications on 2-nitrobenzyl moiety utilized in NGS to eliminate "chewback activity" and improve cleavage/termination efficiencies, respectively. As shown in FIGS. 11A to 11C, TdT incorporates LTA-1 much more efficiently than the more highly substituted LTA-2 (FIG. 10A). However, termination efficiency is poor, and 3 bases (@2 uM primer) or more (@80 nM primer) are incorporated in a single synthesis cycle.

Compared to TdT, Pfu26 appears to incorporate LTA-1 less efficiently based on the number of bases added at 1, 5, and 10 uM concentrations (FIGS. 11D to 11F 2 vs. FIG. 12A). However, unlike TdT, which failed to incorporate LTA-2, Pfu26 provided efficient incorporation and termination in a single incubation step (See FIG. 12B). This result demonstrates the feasibility of using specialized Pfu mutants in combination with both "scarless" and modified reversible terminators, to achieve enzyme-mediated synthesis of natural and non-cognate nucleic acid polymers, respectively.

Example 10

This example tested the multi-cycle addition of a 3'-OH unblocked reversible terminator (LTA-2, shown in FIG. 1F) to the 3' end of a single-stranded priming strand using the Pfu26 mutant polymerase. Single-base extension assays were performed as described in Example 7 using Pfu26 with modified LTA-2 that has α-tert-butyl substituted 2-nitrobenyl terminating group attached to 7-deaza-C7hydroxymethyl group. The modified LTA-2 optionally contains the αS triphosphate modification and HPLC-purified to isolate the Sp isomer (FIGS. 13A and 13C). At each incorporation cycle (3 cycles—FIGS. 13A&13B; 6 cycles—FIG. 13C), 1 ul was removed and saved on ice for ABI 3500 analysis. At each cycle, the remaining reaction volume was purified using MyOne T1 biotinylated beads as follows (for the 3-cycle experiment). 127.5 ul of beads were washed 2× in 1 ml wash solution and resuspended in the original volume with the wash solution. A biotinylated, antisense T7 (underlined) primer with spacer (5'-CCCTATAGTGAGTCGTAT ACG GAG CAT A-biotin) was added at a final concentration of 180 nM. The beads and capture oligo were mixed at 300 rpm for 30 min. at room temperature, washed 2× in 500 ul wash solution, and resuspended in 150 ul of the same. 10 ul of beads/capture oligo mix was added to 9 ul of each incorporation reaction (cycles 2-6) and incubated for 30 min. at 300 rpm at room temperature. The mix was then washed 2× with 500 ul wash solution at room temperature and resuspended in 10 ul Thermopol buffer. To release the Fam-T7 oligo, reactions were incubated at 95° C. for 5 min. and quickly applied to a magnet before removing 8 ul of each eluate for the next round of incorporation. After purification (cycles 2-6), 2 ul of fresh enzyme/LTA mix was added, and the primer extensions were performed and analyzed as described above.

The results (shown in FIGS. 13A to 13C) indicated that Pfu26, in combination with 7-deaza-7-hydroxymethyl-α-tert-butyl-2-nitrobezyl modified LTA, did not generate an individual product with 100% efficiency after 2-3 rounds of TiEOS. Removing the αS modification (FIG. 13B) or incorporating chirally-pure αS (Sp isomer) of 7-deaza-7-hydroxymethyl-α-tert-butyl-2-nitrobenzyl modified LTA (FIGS. 13A, 13C) did not overcome issues with secondary products. However, the results demonstrate proof-of-concept for designing "scarless", non-isomeric reversible terminators that can be used in combination with embodiments of the present mutant polymerase to achieve enzymatic synthesis of long natural and modified nucleic polymers.

Exemplary Embodiments

Although various embodiments are described, it is to be understood that the teachings of this disclosure are not limited to the particular embodiments described, and as such can, of course, vary.

Embodiment 1. A composition comprising a 3'-OH unblocked reversible terminator and a mutant polymerase, wherein the mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

Embodiment 2. The composition of embodiment 1, wherein the mutant polymerase comprises a A486X mutation at a position functionally equivalent to position 486 in Pfu polymerase, wherein X is any amino acid except alanine.

Embodiment 3. The composition of embodiment 2, wherein the A486X mutation is A486F, A486Y, A486N, A486R, or A486H.

Embodiment 4. The composition of any of embodiments 1 to 3, wherein the mutant polymerase further comprises a Y546H mutation at a position functionally equivalent to position 546 in Pfu polymerase.

Embodiment 5. The composition of any of embodiments 1 to 4, wherein the mutant polymerase further comprises a K477W mutation at a position functionally equivalent to position 477 in Pfu polymerase.

Embodiment 6. The composition of any of embodiments 1 to 5, wherein the mutant polymerase further comprises a mutation at a position functionally equivalent to position F494 in Pfu polymerase.

Embodiment 7. The composition of embodiment 6, wherein the F494 mutation is F494C, F494I, F494N, or F494T.

Embodiment 8. The composition of any of the foregoing embodiments, wherein the mutant polymerase is a derivative of *Pyrococcus* polymerase.

Embodiment 9. The composition of embodiment 8, wherein the mutant polymerase comprises the amino acid sequence of SEQ ID NO:2.

Embodiment 10. The composition of any of embodiments 1 to 7, wherein the mutant polymerase is a derivative of a *Thermococcus* polymerase.

Embodiment 11. A method of incorporating a nucleotide to a priming strand comprising a nucleic acid, the method comprising:
  contacting the priming strand with a nucleotide and a mutant polymerase under conditions sufficient for an incorporation reaction,
  wherein said mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

Embodiment 12. The method of embodiment 11, wherein the nucleotide is a 3'-OH unblocked reversible terminator.

Embodiment 13. A method of polynucleotide sequencing comprising:
  (a) forming a duplex comprising a template and a priming strand, wherein the template comprises a target nucleic acid to be sequenced and a primer binding site complementary to at least a portion of the priming strand;
  (b) combining the priming strand with a reversible terminator nucleotide and a mutant polymerase, wherein said mutant polymerase comprises an amino acid sequence that is at least 96% identical to SEQ ID NO:2 and comprises amino acid mutations at positions functionally equivalent to amino acid positions at K477, A486 and Y546 in Pfu polymerase;
  (c) incorporating the reversible terminator at a 3'-end of the priming strand in a template-dependent reaction; and
  (d) identifying the incorporated reversible terminator nucleotide, thereby determining the sequence of the template.

Embodiment 14. The method of embodiment 13, wherein the 3'-OHmethod further comprises repeating steps (c) and (d) at least 80 times.

Embodiment 15. A composition comprising a priming strand, a 3'-OH unblocked reversible terminator 3'-OH, and a mutant polymerase, wherein:
  said mutant polymerase comprises an amino acid sequence that is at least 80% identical to SEQ ID NO:1,
  said mutant polymerase further comprises one or more mutations at positions functionally equivalent to positions L270, E330, Q332, L333, L409, P451, L453, L457, E476, L489, L490, N492, F494, Y497, and E581 in Pfu polymerase; and
  said mutant polymerase has an incorporation activity for the 3'-OH unblocked reversible terminator of at least 4-fold higher than an incorporation activity of the DNA polymerase of SEQ ID NO:11.

Embodiment 16. The composition of embodiment 15, wherein the amino acid sequence is at least 85% identical to SEQ ID NO:1.

Embodiment 17. The composition of embodiment 15, wherein the amino acid sequence is at least 90% identical to SEQ ID NO:1.

Embodiment 18. The composition of embodiment 15, wherein the amino acid sequence is at least 95% identical to SEQ ID NO:1.

Embodiment 19. The composition of any of embodiments 15 to 18, wherein the mutant polymerase does not comprise a mutation at any position functionally equivalent to positions 266, 267, 268, 269, 329, 336, 399, 400, 403, 404, 407, 408, 410, 411, 450, 452, 455, 456, 458, 459, 460, 461, 462, 463, 464, 465, 466, 475, 477, 478, 479, 480, 481, 482, 483, 485, 487, 488, 491, 493, 495, 496, 498, 499, 500, 515, 522, 545, 546, 577, 579, 580, 582, 584, 591, 595, 603, 606, 607, 608, 612, 613, 614, 664, 665, 666, 668, 669, 674, 675, and 676 in Pfu polymerase.

Embodiment 20. The composition of any of embodiments 15 to 19, wherein the mutant polymerase is a derivative of *Pyrococcus* polymerase.

Embodiment 21. The composition of any of embodiments 15 to 19, wherein the mutant polymerase is a derivative of a *Thermococcus* polymerase.

Embodiment 22. The composition of any of embodiments 15 to 21, wherein the composition further comprises a template comprising a primer binding site complementary to at least a portion of the priming strand.

Embodiment 23. The composition of any of embodiments 15 to 22, wherein the composition further comprises 546H and 486X mutations.

Embodiment 24. The composition of any of embodiments 15 to 23, wherein the composition does not contain a template complementary to the priming strand.

Embodiment 25. A method of incorporating 3'-OH-unmodified reversible terminators into a priming strand, the method comprising:
  contacting a priming strand with a 3'-OH-unmodified reversible terminator and a mutant polymerase under conditions sufficient for an incorporation reaction, wherein the mutant polymerase comprises an amino acid sequence that is at least 80% identical to SEQ ID NO:1 and one or more mutations at positions functionally equivalent to positions L270, E330, Q332, L333, L409, P451, L453, L457, E476, L489, L490, N492, F494, Y497, and E581 in Pfu polymerase; and
  incorporating the 3'-OH-unmodified reversible terminator at a 3'-end of the priming strand.

Embodiment 26. The method of embodiment 25, wherein the 3'-OH-unmodified reversible terminator is a 2-nitrobenzyl-modified nucleotide.

Embodiment 27. The method of embodiment 25, wherein the 3'-OH unmodified reversible terminator is a C7- or C5-hydroxymethyl-α-tert-butyl-2-nitrobenzyl modified nucleotide and its α-thio derivative.

Embodiment 28. The method of any of embodiments 25 to 27, wherein said mutant polymerase comprises at least one amino acid mutation at a position functionally equivalent to position 492 in Pfu polymerase, and the method comprises selectively incorporating the terminators.

Embodiment 29. The method of embodiment 28, wherein the mutation is selected from N492I, N492V, or N492P.

Embodiment 30. The method of embodiment 28, wherein a 3'-OH unblocked reversible-terminator comprising a cytosine base is selectively incorporated by the mutant polymerase.

Embodiment 31. A composition comprising a priming strand, an 3'-OH-unmodified reversible terminator, and a mutant polymerase that is at least 96% identical to SEQ ID NO:2 and comprises:

a Y546H mutation at a position functionally equivalent to position 546 in Pfu polymerase;
  a L409Y, L409H or L409F mutation at a position functionally equivalent to position 409 in Pfu polymerase; and
  a A486X mutation at a position functionally equivalent to position 486 in Pfu polymerase, wherein X is any amino acid except alanine.

Embodiment 32. The composition of embodiment 31, wherein the composition does not contain a template complementary to the priming strand.

Embodiment 33. The composition of embodiment 31 or 32, wherein the mutant polymerase further comprises one or more mutations at positions functionally equivalent to positions L270, E330, Q332, L333, P451, L453, L457, E476, L489, L490, N492, F494, Y497, and E581 in Pfu polymerase.

Embodiment 34. The composition of embodiment 31 or 32, wherein the mutant polymerase comprises the amino acid sequence of SEQ ID NO: 4 or SEQ ID NO: 5.

Embodiment 35. The composition of any of embodiments 31 to 34, wherein the mutant polymerase has an incorporation activity at least 2-fold higher than an incorporation activity of a DNA polymerase of SEQ ID NO:11.

Embodiment 36. The composition of any of embodiments 31 to 35, wherein the mutant polymerase is a derivative of *Pyrococcus* polymerase.

Embodiment 37. The composition of any of embodiments 31 to 36, wherein the mutant polymerase comprises the amino acid sequence of SEQ ID NO:2.

Embodiment 38. The composition of any of embodiments 31 to 35, wherein the mutant polymerase is a derivative of a *Thermococcus* polymerase.

Embodiment 39. A method for incorporating a single nucleotide into a priming strand in a template-independent reaction, the method comprising:
  combining a priming strand with a 3'-OH-unmodified reversible terminator and a mutant polymerase, wherein the mutant polymerase is at least 96% identical to SEQ ID NO:2 and comprises:
    a Y546H mutation at a position functionally equivalent to position 546 in Pfu polymerase;
    a L409Y, L409H or L409F mutation at a position functionally equivalent to position 409 in Pfu polymerase; and
    a A486X mutation at a position functionally equivalent to position 486 in Pfu polymerase, wherein X is any amino acid except alanine;
  wherein incorporation of the terminator is at least 2-fold higher than for the mutant DNA polymerase of SEQ ID NO:11.

Embodiment 40. A method of template-independent oligonucleotide synthesis comprising:
  combining a priming strand, an 3'-OH-unmodified reversible terminator, and a mutant DNA polymerase, wherein mutant DNA polymerase comprises:
    an amino acid sequences that is at least 96% identical to SEQ ID NO:2;
    a Y546H mutation to histidine at a position functionally equivalent to position 546 in Pfu polymerase;
    a L409Y, L409H, or L409F mutation at a position functionally equivalent to position 409 in Pfu polymerase; and
    a A486X mutation at a position functionally equivalent to position 486 in Pfu polymerase, wherein X is any amino acid except alanine;

incorporating the 3'-OH-unmodified reversible terminator to the priming strand.

Embodiment 41. The method of embodiment 39 or 40, wherein the polymerase further comprises one or more mutations at positions functionally equivalent to positions L270, E330, Q332, L333, P451, L453, L457, E476, L489, L490, N492, F494, Y497, and E581 in Pfu polymerase.

Embodiment 42. The method of any of embodiments 39 to 41, wherein the 3'-OH-unmodified reversible terminator is a 2-nitrobenzyl-modified nucleotide.

Embodiment 43. The method of any of embodiments 39 to 41, wherein the 3'-OH unmodified reversible terminator is a a C7- or C5-hydroxymethyl-α-tertbutyl-2-nitrobenzyl modified nucleotide and its α-thio derivative.

CITATIONS AND REFERENCES

Jensen, et al., "Template-Independent Enzymatic Oligonucleotide Synthesis (TiEOS): Its History, Prospects, and Challenges." Biochemistry. 2018 Mar. 27; 57(12):1821-1832. doi: 10.1021/acs.biochem.7b00937. Epub 2018 Mar. 13. PMID: 29533604.

Ramsay, et al., "CyDNA: synthesis and replication of highly Cy-dye substituted DNA by an evolved polymerase." J Am Chem Soc. 2010 Apr. 14; 132(14):5096-104. doi: 10.1021/ja909180c. PMID: 20235594; PMCID: PMC2850551.

Cozens, et al., "A short adaptive path from DNA to RNA polymerases." Proc Natl Acad Sci USA. 2012 May 22;109(21):8067-72. doi: 10.1073/pnas.1120964109. Epub 2012 May 7. PMID: 22566643; PMCID: PMC3361454.

Hansen, et al., "Engineered split in Pfu DNA polymerase fingers domain improves incorporation of nucleotide gamma-phosphate derivative." Nucleic Acids Res. 2011 March;39(5):1801-10. doi: 10.1093/nar/gkq1053. Epub 2010 Nov. 9. PMID: 21062827; PMCID: PMC3061061.

Palluk, et al., "De novo DNA synthesis using polymerase-nucleotide conjugates." Nat Biotechnol. 2018 August; 36(7):645-650. doi: 10.1038/nbt.4173. Epub 2018 Jun. 18. PMID: 29912208.

Eisenstein, "Enzymatic DNA synthesis enters new phase." Nat Biotechnol. 2020 October;38(10):1113-1115. doi: 10.1038/s41587-020-0695-9. PMID: 33020638.

Hoff, et al. "Enzymatic Synthesis of Designer DNA Using Cyclic Reversible Termination and a Universal Template." ACS Synth Biol. 2020 Feb. 21; 9(2):283-293. doi: 10.1021/acssynbio.9b00315. Epub 2020 Jan. 14. PMID: 31895546.

Mathews, et al., "3'-O-Caged 2'-Deoxynucleoside Triphosphates for Light-Mediated, Enzyme-Catalyzed, Template-Independent DNA Synthesis." Curr Protoc Nucleic Acid Chem. 2017 Dec. 24; 71:13.17.1-13.17.38. doi: 10.1002/cpnc.41. PMID: 29275537.

Pinheiro, et al., "Synthetic genetic polymers capable of heredity and evolution." (2012) Science 336:341-4. doi: 10.1126/science.1217622. PMID: 22517858.

Kennedy, et al., "The Mechanistic Architecture of the Thermostable *Pyrococcus Furiosus* Family B DNA Polymerase Motif A and its Interaction with dNTP Substrate." (2009) Biochemistry 48(47):11161-11168. doi: 10.1021/bi9010122. PMCID: PMC3097049

Wu, et al., "Termination of DNA synthesis by N6-alkylated, not 3'-O-alkylated, photocleavable 2'-deoxyadenosine triphosphates," Nucleic Acids Research, Volume 35, Issue 19, 1 Oct. 2007, Pages 6339-6349

Litosh, et al., "Improved nucleotide selectivity and termination of 3'-OH unblocked reversible terminators by molecular tuning of 2-nitrobenzyl alkylated HOMedU triphosphates," Nucleic Acids Research, Volume 39, Issue 6, 1 Mar. 2011, Page e39

Stupi, et al., "Stereochemistry of Benzylic Carbon Substitution Coupled with Ring Modification of 2-Nitrobenzyl Groups as Key Determinants for Fast-Cleaving Reversible Terminators", Angew. Chem. Int. Ed. 2012, 51, 1724-1727;

Gardner, et al., "Rapid incorporation kinetics and improved fidelity of a novel class of 3'-OH unblocked reversible terminators", Nucleic Acids Research, 40(15):7404-7415 (2012)

Gardner, et al., "Determinants of nucleotide sugar recognition in an archaeon DNA polymerase", Nucleic Acids Research, 27(12):2545-53 (1999)

Evans, et al., "Improving dideoxynucleotide-triphosphate utilisation by the hyperthermophilic DNA polymerase from the archaeon *Pyrococcus furiosus*", Nucleic Acids Research, 28(5):1059-66 (2000)

Ramsay, et al., "CyDNA: Synthesis and Replication of Highly Cy-Dye Substituted DNA by an Evolved Polymerase" JACS 132:5096-5104 (2010)

Hertzog, et al., "A high-performance, low-cost approach to next-generation sequencing", BioOptics World. 2011 Issue November/December 2011

Smith, et al., U.S. Pat. No. 9,273,352
Bomati, et al., U.S. Pat. No. 9,677,057
Reisinger, et al., U.S. Pat. No. 9,677,059
Chen, et al., U.S. Pat. No. 9,765,309
Chen, et al., US Pat. App. Publication No. 20160032377
Arezi, et al., US Pat. App. Publication No. 20030228616
Wu, et al., U.S. Pat. No. 8,969,535
Litosh, et al., U.S. Pat. No. 9,200,319
Stupi, et al., U.S. Pat. No. 10,041,115
Eberwine, et al., US Pat. App. Publication No. 20200216841

What is claimed is:

1. A composition comprising a 3'-OH unblocked reversible terminator and a mutant polymerase, wherein the mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

2. The composition of claim 1, wherein the mutant polymerase comprises a A486X mutation at a position functionally equivalent to position 486 in Pfu polymerase, wherein X is any amino acid except alanine.

3. The composition of claim 2, wherein the A486X mutation is A486F, A486Y, A486N, A486R, or A486H.

4. The composition of claim 1, wherein the mutant polymerase comprises a Y546H mutation at a position functionally equivalent to position 546 in Pfu polymerase.

5. The composition of claim 1, wherein the mutant polymerase further comprises a K477W mutation at a position functionally equivalent to position 477 in Pfu polymerase.

6. The composition of claim 1, wherein the mutant polymerase further comprises a mutation at a position functionally equivalent to position F494 in Pfu polymerase.

7. The composition of claim 6, wherein the F494 mutation is F494C, F494I, F494N, or F494T.

8. The composition of claim 1, wherein the mutant polymerase is a derivative of *Pyrococcus* polymerase.

9. The composition of claim 8, wherein the mutant polymerase comprises the amino acid sequence of SEQ ID NO:2.

10. The composition of claim 1, wherein the mutant polymerase is a derivative of a *Thermococcus* polymerase.

11. A method of incorporating a nucleotide to a priming strand comprising a nucleic acid, the method comprising:

contacting the priming strand with a nucleotide and a mutant polymerase under conditions sufficient for an incorporation reaction, wherein said mutant polymerase comprises an amino acid sequence that is at least 96% identical to SEQ ID NO:2 and comprises amino acid mutations at positions functionally equivalent to amino acid positions at K477, A486 and Y546 in Pfu polymerase.

12. The method of claim 11, wherein the nucleotide is a 3'-OH unblocked reversible terminator.

13. A method of polynucleotide sequencing comprising:

(a) forming a duplex comprising a template and a priming strand, wherein the template comprises a target nucleic acid to be sequenced and a primer binding site complementary to at least a portion of the priming strand;

(b) combining the priming strand with a reversible terminator nucleotide and a mutant polymerase, wherein said mutant polymerase comprises an amino acid sequence that is at least 96% identical to SEQ ID NO:2 and comprises amino acid mutations at positions functionally equivalent to amino acid positions at K477, A486 and Y546 in Pfu polymerase;

(c) incorporating the reversible terminator at a 3'-end of the priming strand in a template-dependent reaction; and (d) identifying the incorporated reversible terminator nucleotide, thereby determining the sequence of the template.

14. The method of claim 13, wherein the method further comprises repeating steps (c) and (d) at least 80 times.

15. A composition comprising a priming strand, an 3'-OH-unmodified reversible terminator, and a mutant polymerase that is at least 96% identical to SEQ ID NO:2 and comprises:

a Y546H mutation at a position functionally equivalent to position 546 in Pfu polymerase;

a L409Y, L409H or L409F mutation at a position functionally equivalent to position 409 in Pfu polymerase; and a A486X mutation at a position functionally equivalent to position 486 in Pfu polymerase, wherein X is any amino acid except alanine.

16. The composition of claim 15, wherein the composition does not contain a template complementary to the priming strand.

17. The composition of claim 15, wherein the mutant polymerase further comprises one or more mutations at positions functionally equivalent to positions L270, E330, Q332, L333, P451, L453, L457, E476, L489, L490, N492, F494, Y497, and E581 in Pfu polymerase.

18. The composition of claim 15, wherein the mutant polymerase comprises the amino acid sequence of SEQ ID NO: 4 or SEQ ID NO: 5.

19. The composition of claim 15, wherein the mutant polymerase has an incorporation activity at least 2-fold higher than an incorporation activity of a DNA polymerase of SEQ ID NO:11.

20. The composition of claim 15, wherein the mutant polymerase is a derivative of *Pyrococcus* polymerase.

21. The composition of claim 15, wherein the mutant polymerase comprises the amino acid sequence of SEQ ID NO:2.

22. The composition of claim 15, wherein the mutant polymerase is a derivative of a *Thermococcus* polymerase.

* * * * *

UNITED STATES PATENT AND TRADEMARK OFFICE
CERTIFICATE OF CORRECTION

| | |
|---|---|
| PATENT NO. | : 11,773,380 B1 |
| APPLICATION NO. | : 17/894854 |
| DATED | : October 3, 2023 |
| INVENTOR(S) | : Michelle Cayouette et al. |

It is certified that error appears in the above-identified patent and that said Letters Patent is hereby corrected as shown below:

In the Specification

In Column 4, Line 51, delete "5-hydroxylmethyluracil" and insert -- 5-hydroxymethyluracil --.

In Column 4, Line 60, delete "nitrobenzul" and insert -- nitrobenzyl --.

In Column 4, Line 60, delete "7-hydroxylmethyl" and insert -- 7-hydroxymethyl --.

In Column 7, Line 58, delete "archael" and insert -- archaeal --.

In Column 7, Line 59, delete "archea," and insert -- archaea, --.

In Column 10, Line 27, delete "piming" and insert -- priming --.

In Column 14, Line 25, delete "polynucleatide" and insert -- polynucleotide --.

In Column 14, Line 61, delete "efficiencies" and insert -- efficiencies. --.

In Column 17, Line 53, delete "furisosus)" and insert -- furiosus) --.

In Column 21, Line 8, delete "1475," and insert -- I475, --.

In Column 22, Line 53, delete "204" and insert -- 2 µM --.

In Column 23, Line 16, delete "5004, and 10004)." and insert -- 50 µM, and 100 µM). --.

In Column 23, Line 50, delete "10E" and insert -- FIG. 10E --.

In Column 24, Line 11, delete "(FIG." and insert -- (FIGS. --.

Signed and Sealed this
Thirteenth Day of February, 2024

*Katherine Kelly Vidal*

Katherine Kelly Vidal
*Director of the United States Patent and Trademark Office*

CERTIFICATE OF CORRECTION (continued)
U.S. Pat. No. 11,773,380 B1

Figure 11D:
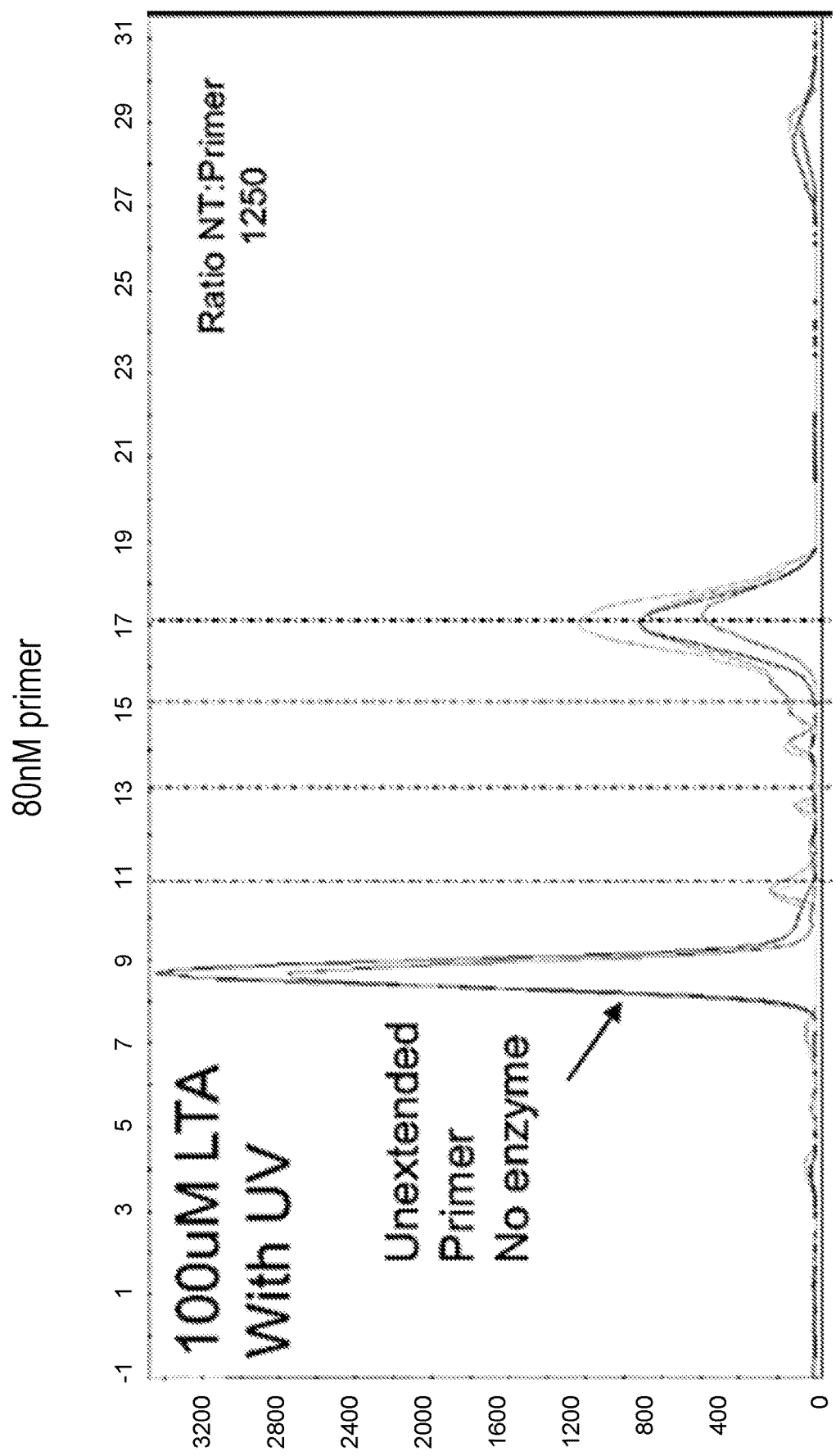
Figure 11D:
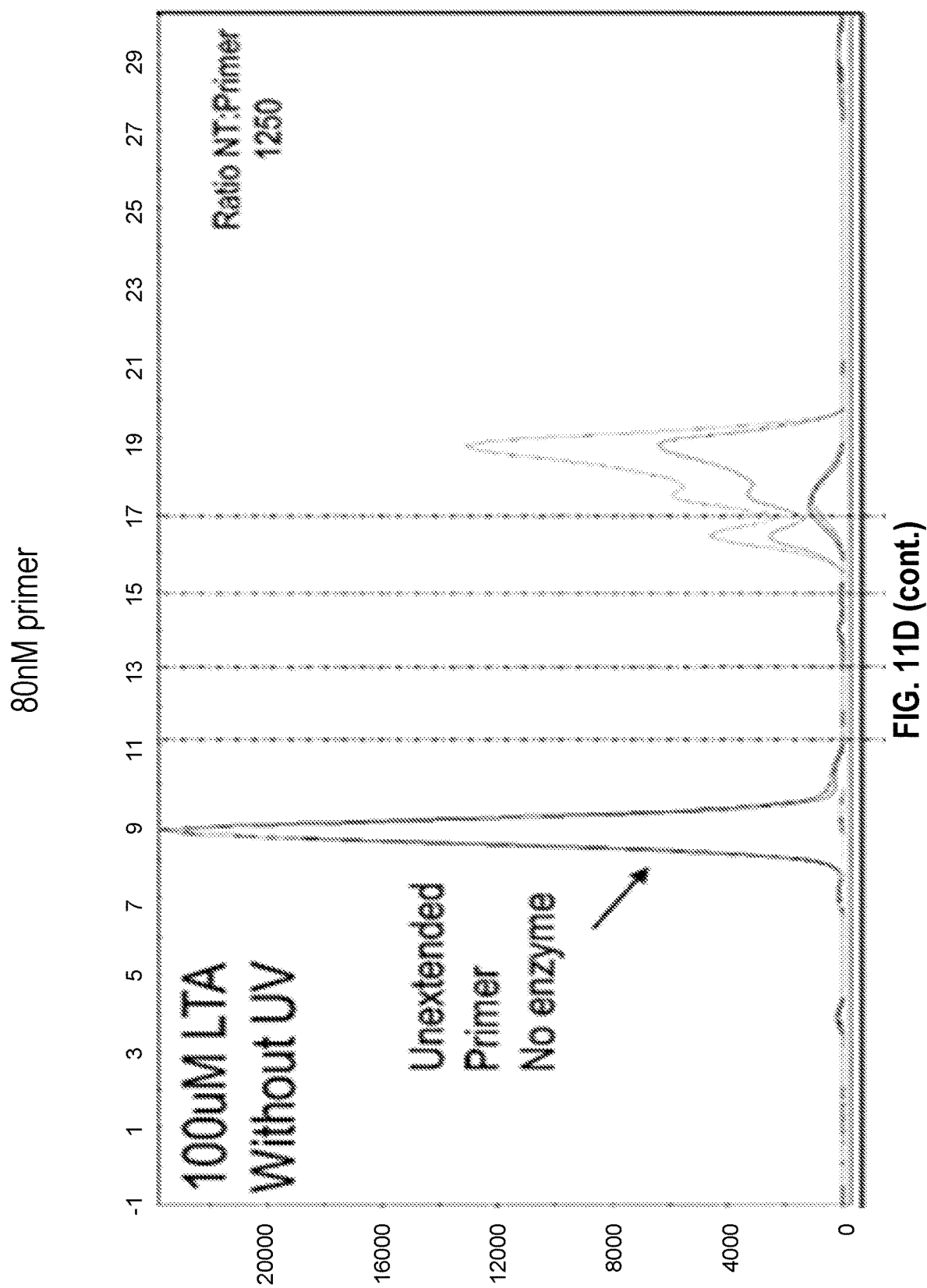
Figure 11D:
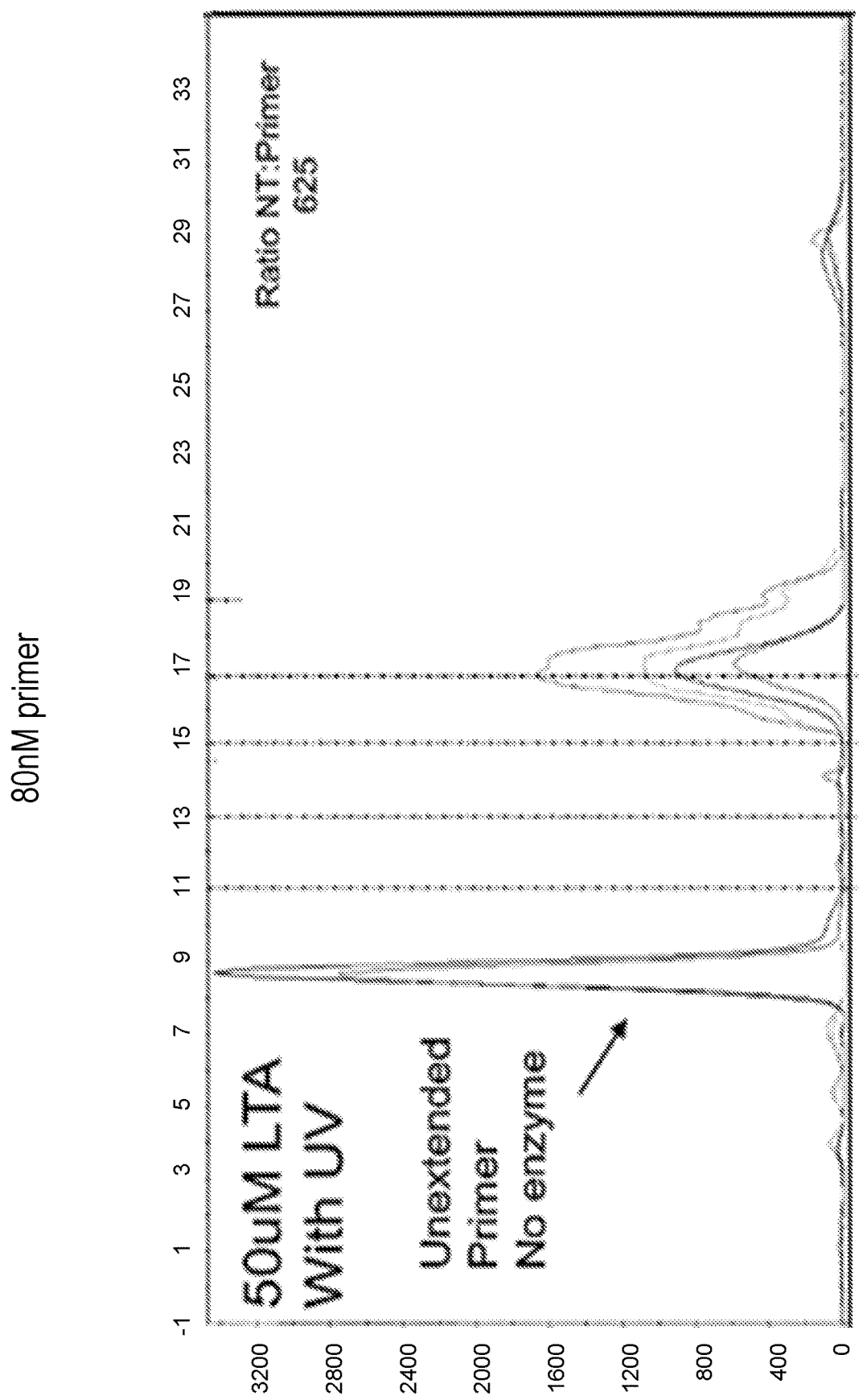
Figure 11D:
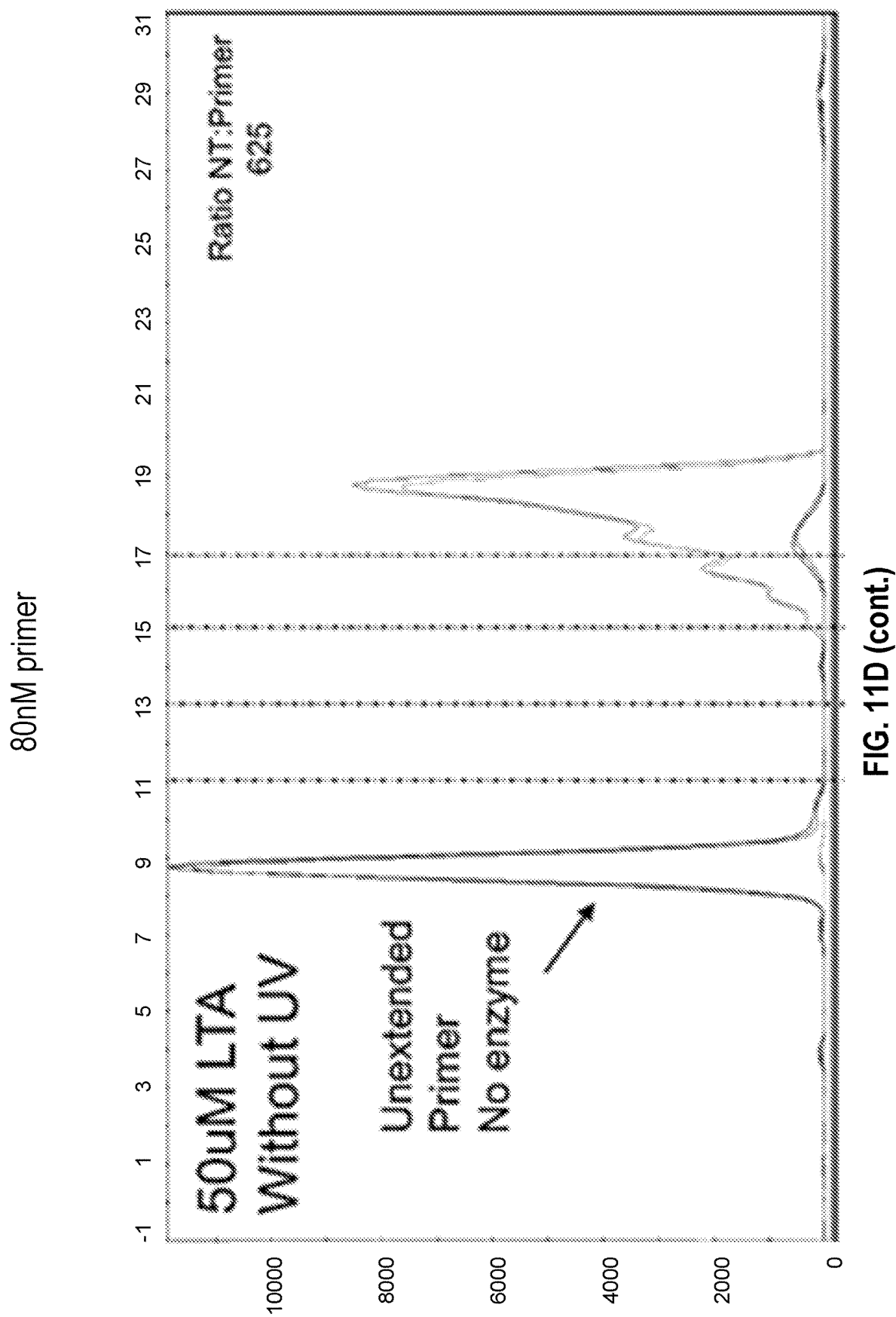
Figure 11E:
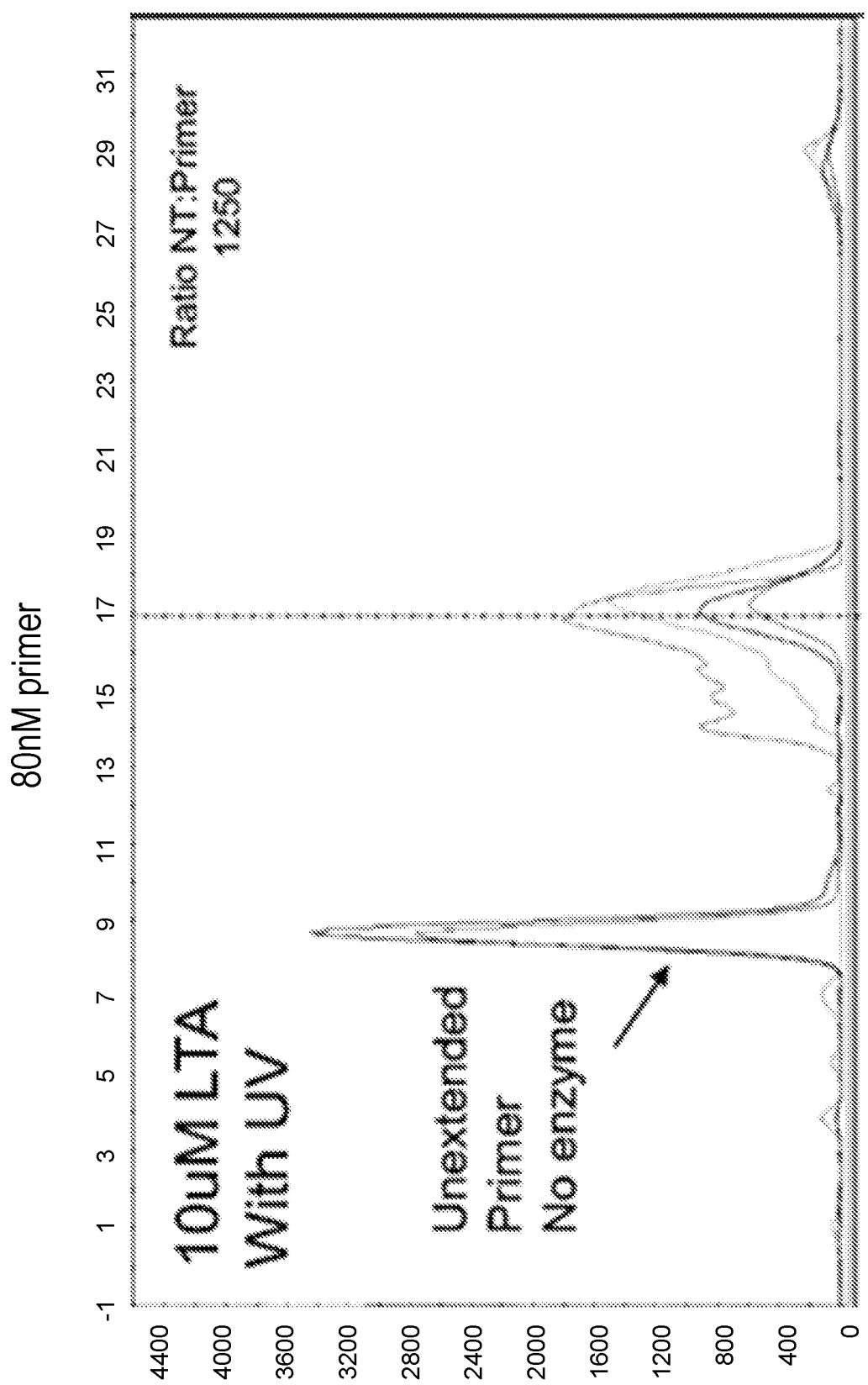
Figure 11E:
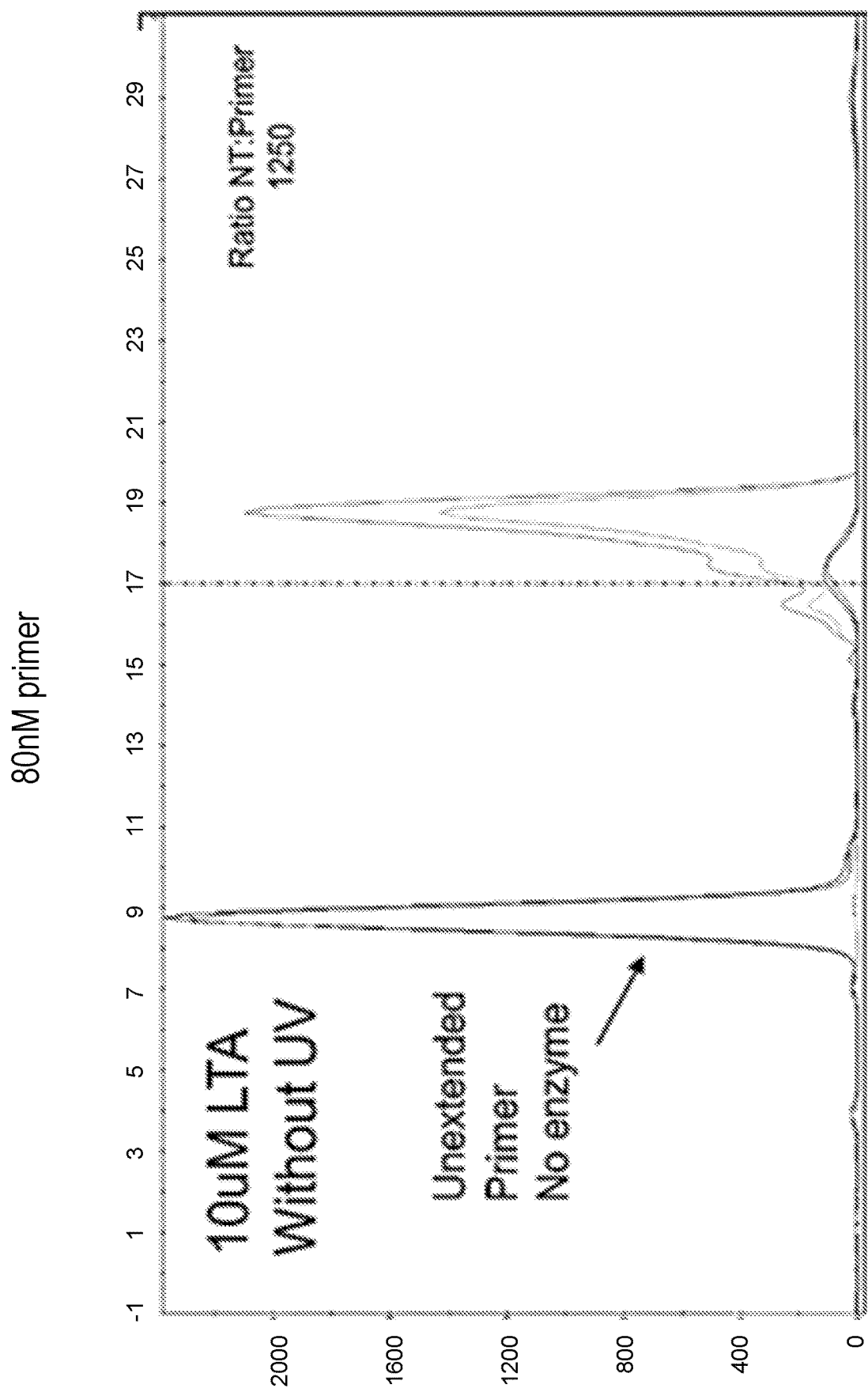
Figure 11E:
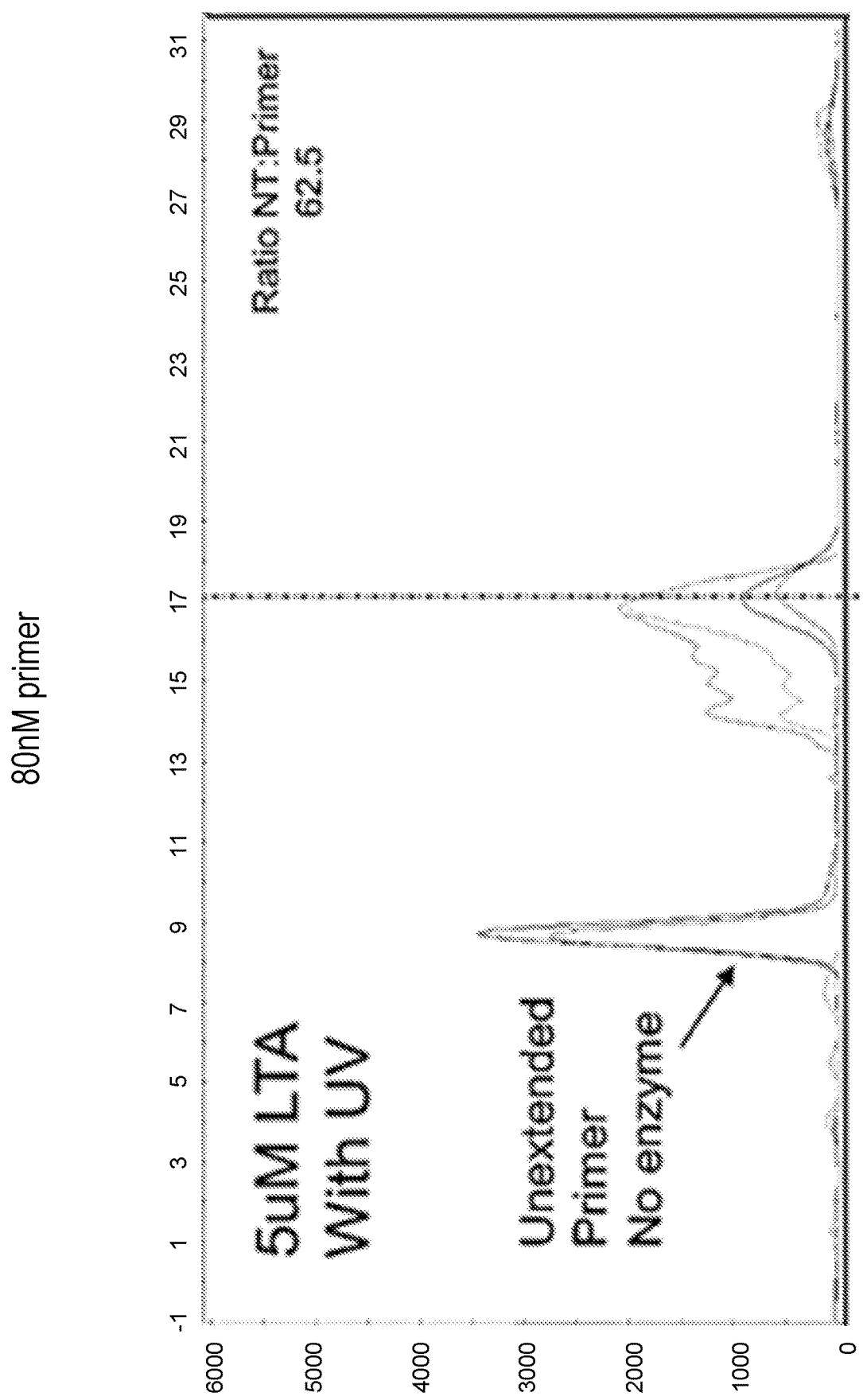
Figure 11E:
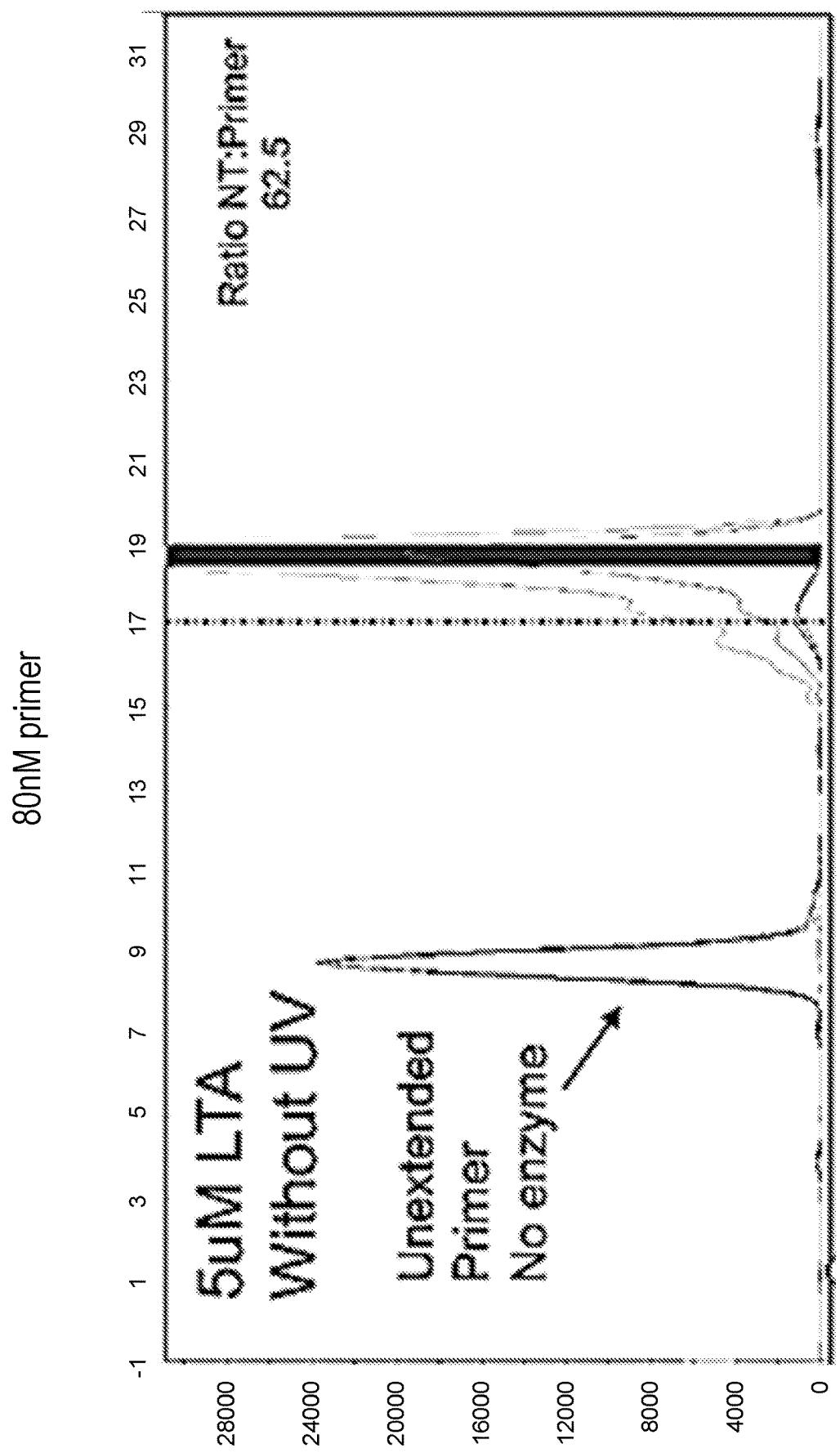
Figure 11F:
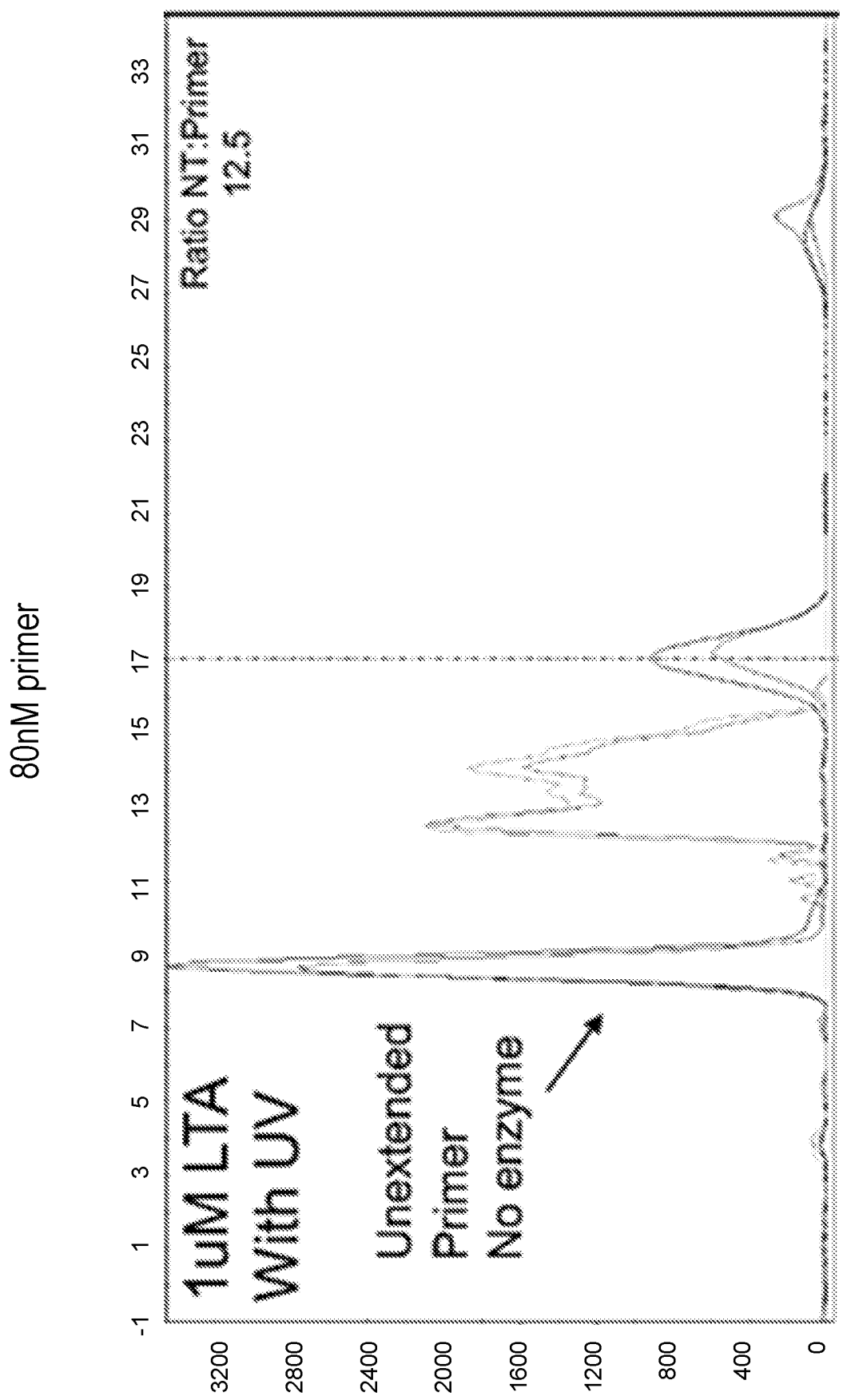
Figure 11F:
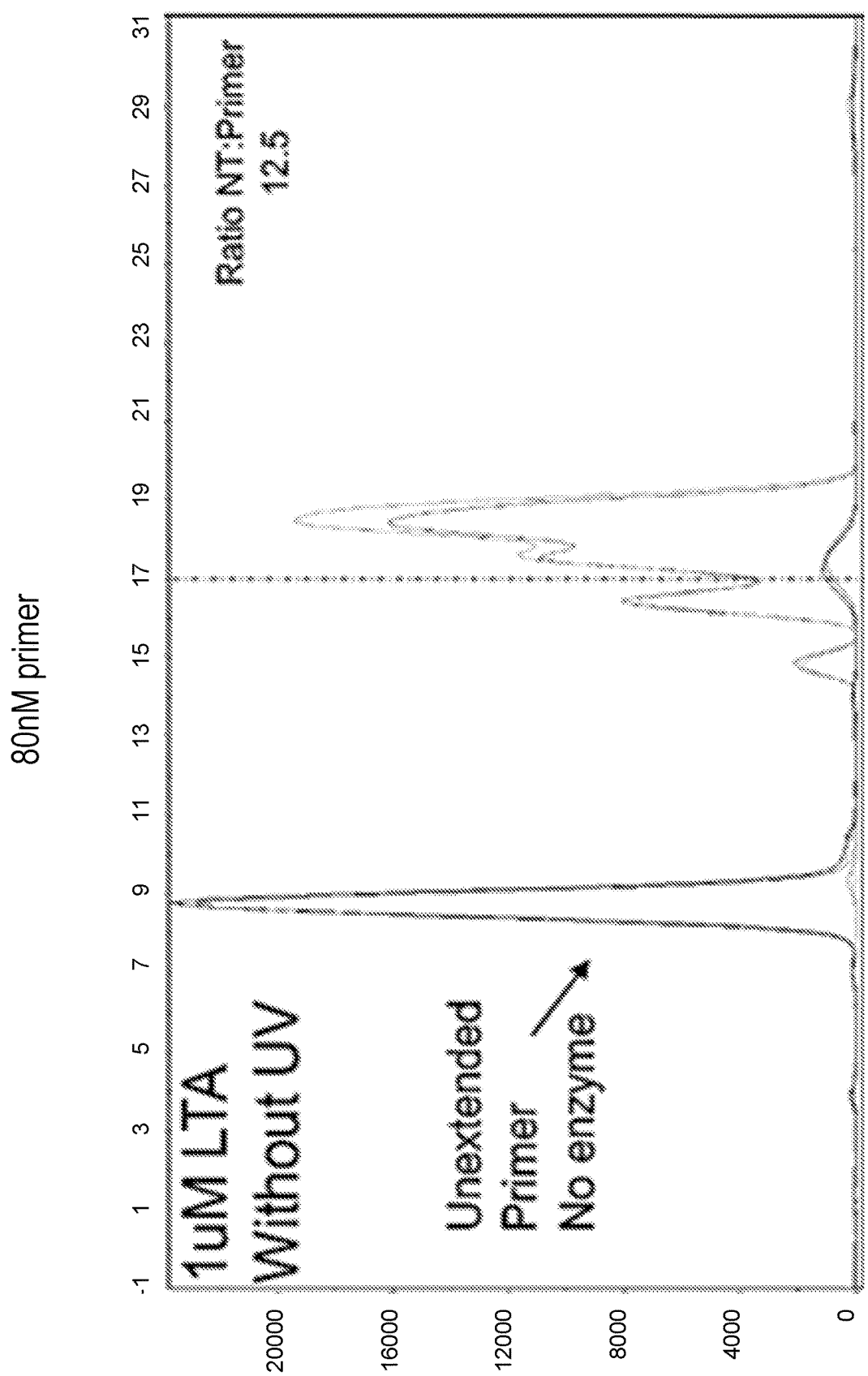

In Column 24, Line 11, delete "(FIG. 11D" and insert -- (FIGS. 11D --.

In Column 24, Lines 58-59, delete "2-nitrobenyl" and insert -- 2-nitrobenzyl --.

In Column 25, Line 22, delete "2-nitrobezyl" and insert -- 2-nitrobenzyl --.

In Column 26, Line 46, delete "3'-OHmethod" and insert -- 3'-OH method --.

In Column 29, Line 14, delete "a a" and insert -- a --.

SEQUENCE LISTING

```
Sequence total quantity: 12
SEQ ID NO: 1            moltype = AA  length = 775
FEATURE                 Location/Qualifiers
source                  1..775
                        mol_type = protein
                        organism = Pyrococcus furiosus
SEQUENCE: 1
MILDVDYITE EGKPVIRLFK KENGKFKIEH DRTFRPYIYA LLRDDSKIEE VKKITGERHG   60
KIVRIVDVEK VEKKFLGKPI TVWKLYLEHP QDVPTIREKV REHPAVVDIF EYDIPFAKRY  120
LIDKGLIPME GEEELKILAF DIETLYHEGE EFGKGPIIMI SYADENEAKV ITWKNIDLPY  180
VEVVSSEREM IKRFLRIIRE KDPDIIVTYN GDSFDFPYLA KRAEKLGIKL TIGRDGSEPK  240
MQRIGDMTAV EVKGRIHFDL YHVITRTINL PTYTLEAVYE AIFGKPKEKV YADEIAKAWE  300
SGENLERVAK YSMEDAKATY ELGKEFLPME IQLSRLVGQP LWDVSRSSTG NLVEWFLLRK  360
```

```
AYERNEVAPN KPSEEEYQRR LRESYTGGFV KEPEKGLWEN IVYLDFRALY PSIIITHNVS    420
PDTLNLEGCK NYDIAPQVGH KFCKDIPGFI PSLLGHLLEE RQKIKTKMKE TQDPIEKILL    480
DYRQKAIKLL ANSFYGYYGY AKARWYCKEC AESVTAWGRK YIELVWKELE EKFGFKVLYI    540
DTDGLYATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS         775

SEQ ID NO: 2               moltype = AA   length = 775
FEATURE                    Location/Qualifiers
REGION                     1..775
                           note = Mutant of Pyrococcus furiosus Polymerase
source                     1..775
                           mol_type = protein
                           organism = synthetic construct
SEQUENCE: 2
MILDVDYITE EGKPVIRLFK KENGKFKIEH DRTFRPYIYA LLRDDSKIEE VKKITGERHG     60
KIVRIVDVEK VEKKFLGKPI TVWKLYLEHP QDVPTIREKV REHPAVVDIF EYDIPFAKRY    120
LIDKGLIPME GEEELKILAF AIATLYHEGE EFGKGPIIMI SYADENEAKV ITWKNIDLPY    180
VEVVSSEREM IKRFLRIIRE KDPDIIVTYN GDSFDFPYLA KRAEKLGIKL TIGRDGSEPK    240
MQRIGDMTAV EVKGRIHFDL YHVITRTINL PTYTLEAVYE AIFGKPKEKV YADEIAKAWE    300
SGENLERVAK YSMEDAKATY ELGKEFLPME IQLSRLVGQP LWDVSRSSTG NLVEWFLLRK    360
AYERNEVAPN KPSEEEYQRR LRESYTGGFV KEPEKGLWEN IVYLDFRALY PSIIITHNVS    420
PDTLNLEGCK NYDIAPQVGH KFCKDIPGFI PSLLGHLLEE RQKIKTKMKE TQDPIEWILL    480
DYRQKLIKLL ANSFYGYYGY AKARWYCKEC AESVTAWGRK YIELVWKELE EKFGFKVLYI    540
DTDGLHATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS         775

SEQ ID NO: 3               moltype = AA   length = 775
FEATURE                    Location/Qualifiers
REGION                     1..775
                           note = Mutant of Pyrococcus furiosus Polymerase
source                     1..775
                           mol_type = protein
                           organism = synthetic construct
SEQUENCE: 3
MILDVDYITE EGKPIIRLFK KENGKFRIEH DRTFRPYIYA LLRDDSKIEE IKKITGERHG     60
KIVRIVDVEK VEKKFLGKPV TVWRLYLEHP QDVPTIREKV KEHPAVIDIF EYDIPFAKRY    120
LIDKGLVPAE GEEELKILAF AIATLYHEGE EFGKGPIIMI SYADENEAKV ITWKNIDLPY    180
VEVVSSEREM IKRFVKIIKE KDPDIIVTYN GDSFDFPYLA KRAEKLGVKL TIGRDGSEPK    240
MQRIGDMTAV EVKGRIHFDL YHVITRTINL PTYTLEAVYE AIFGKPKEKV YADEIAKAWE    300
SGENLERVAK YSMEDAKATY ELGKEFLPME IQLSRLVGQP LWDVSRSSTG NLVEWFLLRK    360
AYERNEVAPN KPSEEEYQRR LRESYTGGFV KEPEKGLWEN IVYLDFRALY PSIIITHNVS    420
PDTLNLEGCK NYDIAPQVGH KFCKDIPGFI PSLLGHLLEE RQKIKTKMKE TQDPIEWILL    480
DYRQKLIKLL ANSFYGYYGY ARARWYCREC AESVTAWGRK YIELTWKELE EKFGFKVLYI    540
DTDGLHATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS         775

SEQ ID NO: 4               moltype = AA   length = 775
FEATURE                    Location/Qualifiers
REGION                     1..775
                           note = Mutant of Pyrococcus furiosus Polymerase
source                     1..775
                           mol_type = protein
                           organism = synthetic construct
SEQUENCE: 4
MILDVDYITE EGKPVIRLFK KENGKFKIEH DRTFRPYIYA LLRDDSKIEE VKKITGERHG     60
KIVRIVDVEK VEKKFLGKPI TVWKLYLEHP QDVPTIREKV REHPAVVDIF EYDIPFAKRY    120
LIDKGLIPME GEEELKILAF AIATLYHEGE EFGKGPIIMI SYADENEAKV ITWKNIDLPY    180
VEVVSSEREM IKRFLRIIRE KDPDIIVTYN GDSFDFPYLA KRAEKLGIKL TIGRDGSEPK    240
MQRIGDMTAV EVKGRIHFDL YHVITRTINL PTYTLEAVYE AIFGKPKEKV YADEIAKAWE    300
SGENLERVAK YSMEDAKATY ELGKEFLPME IQLSRLVGQP LWDVSRSSTG NLVEWFLLRK    360
AYERNEVAPN KPSEEEYQRR LRESYTGGFV KEPEKGLWEN IVYLDFRAYY PSIIITHNVS    420
PDTLNLEGCK NYDIAPQVGH KFCKDIPGFI PSLLGHLLEE RQKIKTKMKE TQDPIEWILL    480
DYRQKLIKLL ANSFYGYYGY AKARWYCKEC AESVTAWGRK YIELVWKELE EKFGFKVLYI    540
DTDGLHATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS         775

SEQ ID NO: 5               moltype = AA   length = 775
FEATURE                    Location/Qualifiers
REGION                     1..775
                           note = Mutant of Pyrococcus furiosus Polymerase
source                     1..775
```

```
                        mol_type = protein
                        organism = synthetic construct
SEQUENCE: 5
MILDVDYITE EGKPVIRLFK KENGKFKIEH DRTFRPYIYA LLRDDSKIEE VKKITGERHG    60
KIVRIVDVEK VEKKFLGKPI TVWKLYLEHP QDVPTIREKV REHPAVVDIF EYDIPFAKRY   120
LIDKGLIPME GEEELKILAF AIATLYHEGE EFGKGPIIMI SYADENEAKV ITWKNIDLPY   180
VEVVSSEREM IKRFLRIIRE KDPDIIVTYN GDSFDFPYLA KRAEKLGIKL TIGRDGSEPK   240
MQRIGDMTAV EVKGRIHFDL YHVITRTINL PTYTLEAVYE AIFGKPKEKV YADEIAKAWE   300
SGENLERVAK YSMEDAKATY ELGKEFLPME IQLSRLVGQP LWDVSRSSTG NLVEWFLLRK   360
AYERNEVAPN KPSEEEYQRR LRESYTGGFV KEPEKGLWEN IVYLDFRAYY PSIIITHNVS   420
PDTLNLEGCK NYDIAPQVGH KFCKDIPGFI PSLLGHLLEE RQKIKTKMKE TQDPIEWILL   480
DYRQKRIKLL ANSFYGYYGY AKARWYCKEC AESVTAWGRK YIELVWKELE EKFGFKVLYI   540
DTDGLHATIP GGESEEIKKK ALEFVKYINS KLPGLLELEY EGFYKRGFFV TKKRYAVIDE   600
EGKVITRGLE IVRRDWSEIA KETQARVLET ILKHGDVEEA VRIVKEVIQK LANYEIPPEK   660
LAIYEQITRP LHEYKAIGPH VAVAKKLAAK GVKIKPGMVI GYIVLRGDGP ISNRAILAEE   720
YDPKKHKYDA EYYIENQVLP AVLRILEGFG YRKEDLRYQK TRQVGLTSWL NIKKS        775

SEQ ID NO: 6             moltype = DNA  length = 20
FEATURE                  Location/Qualifiers
misc_feature             1..20
                        note = Primer for single-base extension reaction
source                   1..20
                        mol_type = other DNA
                        organism = synthetic construct
SEQUENCE: 6
taatacgact cactataggg                                                20

SEQ ID NO: 7             moltype = DNA  length = 49
FEATURE                  Location/Qualifiers
misc_feature             1..49
                        note = Primer for single-base extension reaction
source                   1..49
                        mol_type = other DNA
                        organism = synthetic construct
SEQUENCE: 7
taatacgact cactataggg caggaaacag ctatgaccag gggatcagc                49

SEQ ID NO: 8             moltype = DNA  length = 20
FEATURE                  Location/Qualifiers
misc_feature             1..20
                        note = Primer for single-base extension reaction
source                   1..20
                        mol_type = other DNA
                        organism = synthetic construct
SEQUENCE: 8
taatacgact cactataggg                                                20

SEQ ID NO: 9             moltype = AA  length = 775
FEATURE                  Location/Qualifiers
REGION                   1..775
                        note = Mutant of Pyrococcus furiosus Polymerase
source                   1..775
                        mol_type = protein
                        organism = synthetic construct
SEQUENCE: 9
MILDVDYITE EGKPVIRLFK KENGKFKIEH DRTFRPYIYA LLRDDSKIEE VKKITGERHG    60
KIVRIVDVEK VEKKFLGKPI TVWKLYLEHP QDVPTIREKV REHPAVVDIF EYDIPFAKRY   120
LIDKGLIPME GEEELKILAF AIATLYHEGE EFGKGPIIMI SYADENEAKV ITWKNIDLPY   180
VEVVSSEREM IKRFLRIIRE KDPDIIVTYN GDSFDFPYLA KRAEKLGIKL TIGRDGSEPK   240
MQRIGDMTAV EVKGRIHFDL YHVITRTINL PTYTLEAVYE AIFGKPKEKV YADEIAKAWE   300
SGENLERVAK YSMEDAKATY ELGKEFLPME IQLSRLVGQP LWDVSRSSTG NLVEWFLLRK   360
AYERNEVAPN KPSEEEYQRR LRESYTGGFV KEPEKGLWEN IVYLDFRALY PSIIITHNVS   420
PDTLNLEGCK NYDIAPQVGH KFCKDIPGFI PSLLGHLLEE RQKIKTKMKE TQDPIEKILL   480
DYRQKLIKLL ANSFYGYYGY AKARWYCKEC AESVTAWGRK YIELVWKELE EKFGFKVLYI   540
DTDGLYATIP GGESEEIKKK ALEFVKYINS KLPGLLELEY EGFYKRGFFV TKKRYAVIDE   600
EGKVITRGLE IVRRDWSEIA KETQARVLET ILKHGDVEEA VRIVKEVIQK LANYEIPPEK   660
LAIYEQITRP LHEYKAIGPH VAVAKKLAAK GVKIKPGMVI GYIVLRGDGP ISNRAILAEE   720
YDPKKHKYDA EYYIENQVLP AVLRILEGFG YRKEDLRYQK TRQVGLTSWL NIKKS        775

SEQ ID NO: 10            moltype = AA  length = 775
FEATURE                  Location/Qualifiers
REGION                   1..775
                        note = Artificial Sequence
source                   1..775
                        mol_type = protein
                        organism = synthetic construct
SEQUENCE: 10
MILDVDYITE EGKPVIRLFK KENGKFKIEH DRTFRPYIYA LLRDDSKIEE VKKITGERHG    60
KIVRIVDVEK VEKKFLGKPI TVWKLYLEHP QDVPTIREKV REHPAVVDIF EYDIPFAKRY   120
```

```
LIDKGLIPME GEEELKILAF AIATLYHEGE EFGKGPIIMI SYADENEAKV ITWKNIDLPY    180
VEVVSSEREM IKRFLRIIRE KDPDIIVTYN GDSFDFPYLA KRAEKLGIKL TIGRDGSEPK    240
MQRIGDMTAV EVKGRIHFDL YHVITRTINL PTYTLEAVYE AIFGKPKEKV YADEIAKAWE    300
SGENLERVAK YSMEDAKATY ELGKEFLPME IQLSRLVGQP LWDVSRSSTG NLVEWFLLRK    360
AYERNEVAPN KPSEEEYQRR LRESYTGGFV KEPEKGLWEN IVYLDFRALY PSIIITHNVS    420
PDTLNLEGCK NYDIAPQVGH KFCKDIPGFI PSLLGHLLEE RQKIKTKMKE TQDPIEKILL    480
DYRQKLIKLL ANSFYGYYGY AKARWYCKEC AESVTAWGRK YIELVWKELE EKFGFKVLYI    540
DTDGLHATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS        775

SEQ ID NO: 11           moltype = AA  length = 775
FEATURE                 Location/Qualifiers
REGION                  1..775
                        note = Artificial Sequence
source                  1..775
                        mol_type = protein
                        organism = synthetic construct
SEQUENCE: 11
MILDVDYITE EGKPVIRLFK KENGKFKIEH DRTFRPYIYA LLRDDSKIEE VKKITGERHG     60
KIVRIVDVEK VEKKFLGKPI TVWKLYLEHP QDVPTIREKV REHPAVVDIF EYDIPFAKRY    120
LIDKGLIPME GEEELKILAF AIATLYHEGE EFGKGPIIMI SYADENEAKV ITWKNIDLPY    180
VEVVSSEREM IKRFLRIIRE KDPDIIVTYN GDSFDFPYLA KRAEKLGIKL TIGRDGSEPK    240
MQRIGDMTAV EVKGRIHFDL YHVITRTINL PTYTLEAVYE AIFGKPKEKV YADEIAKAWE    300
SGENLERVAK YSMEDAKATY ELGKEFLPME IQLSRLVGQP LWDVSRSSTG NLVEWFLLRK    360
AYERNEVAPN KPSEEEYQRR LRESYTGGFV KEPEKGLWEN IVYLDFRALY PSIIITHNVS    420
PDTLNLEGCK NYDIAPQVGH KFCKDIPGFI PSLLGHLLEE RQKIKTKMKE TQDPIEKILL    480
DYRQKAIKLL ANSFYGYYGY AKARWYCKEC AESVTAWGRK YIELVWKELE EKFGFKVLYI    540
DTDGLYATIP GGESEEIKKK ALEFVKYINS KLPGLLELEY EGFYKRGFFV TKKRYAVIDE    600
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS        775

SEQ ID NO: 12           moltype = AA  length = 775
FEATURE                 Location/Qualifiers
REGION                  1..775
                        note = Artificial Sequence
source                  1..775
                        mol_type = protein
                        organism = synthetic construct
SEQUENCE: 12
MILDTDYITE NGKPVIRVFK KENGEFKIEY DRTFEPYFYA LLKDDSAIED VKKVTAKRHG     60
TVVKVKRAEK VQKKFLGRPI EVWKLYFNHP QDVPAIRDRI RAHPAVVDIY EYDIPFAKRY    120
LIDKGLIPME GDEELTMLAF AIATLYHEGE EFGTGPILMI SYADGSEARV ITWKKIDLPY    180
VDVVSTEKEM IKRFLRVVRE KDPDVLITYN GDNFDFAYLK KRCEELGIKF TLGRDGSEPK    240
IQRMGDRFAV EVKGRIHFDL YPVIRRTINL PTYTLEAVYE AVFGKPKEKV YAEEIAQAWE    300
SGEGLERVAR YSMEDAKVTY ELGREFFPME AQLSRLIGQS LWDVSRSSTG NLVEWFLLRK    360
AYKRNELAPN KPDERELARR RGGYAGGYVK EPERGLWDNI VYLDFRSLYP SIIITHNVSP    420
DTLNREGCKE YDVAPEVGHK FCKDFPGFIP SLLGDLLEER QKIKRKMKAT VDPLEKKLLD    480
YRQRLIKILA NSFYGYYGYA KARWYCKECA ESVTAWGREY IEMVIRELEE KFGFKVLYAD    540
TDGLHATIPG ADAETVKKKA KEFLKYINPK LPGLLELEYE GFYVRGFFVT KKKYAVIDEE    600
GKITTRGLEI VRRDWSEIAK ETQARVLEAI LKHGDVEEAV RIVKEVTEKL SKYEVPPEKL    660
VIHEQITRDL RDYKATGPHV AVAKRLAARG VKIRPGTVIS YIVLKGSGRI GDRAIPADEF    720
DPTKHRYDAE YYIENQVLPA VERILKAFGY RKEDLRYQKT KQVGLGAWLK VKGKK        775
```